United States Patent [19]
Pamukcu et al.

[11] Patent Number: 6,046,206
[45] Date of Patent: Apr. 4, 2000

[54] METHOD OF TREATING A PATIENT HAVING A PRECANCEROUS LESIONS WITH AMIDE QUINAZOLINE DERIVATIVES

[75] Inventors: Rifat Pamukcu, Spring House, Pa.; Gary Piazza, Highlands Ranch, Colo.

[73] Assignee: Cell Pathways, Inc., Horsham, Pa.

[21] Appl. No.: 08/846,593

[22] Filed: Apr. 30, 1997

Related U.S. Application Data

[63] Continuation of application No. 08/475,197, Jun. 7, 1995, abandoned.

[51] Int. Cl.$^7$ .................................................. A61K 31/505
[52] U.S. Cl. .......................... 514/259; 514/260; 514/267
[58] Field of Search .................................. 514/259, 260, 514/267

[56] References Cited

U.S. PATENT DOCUMENTS

| | | |
|---|---|---|
| 3,031,450 | 4/1962 | Fischer et al. . |
| 3,161,654 | 12/1964 | Shen . |
| 3,322,755 | 5/1967 | Roch et al. . |
| 3,517,005 | 6/1970 | Cronin et al. . |
| 3,594,480 | 7/1971 | Cronin et al. . |
| 3,647,858 | 3/1972 | Hinkley et al. . |
| 3,654,349 | 4/1972 | Shen et al. . |
| 3,780,040 | 12/1973 | Schnettler et al. . |
| 3,812,127 | 5/1974 | Cronin et al. . |
| 3,819,631 | 6/1974 | Broughton et al. . |
| 3,920,636 | 11/1975 | Takahasi et al. . |
| 4,001,237 | 1/1977 | Partyka et al. . |
| 4,001,238 | 1/1977 | Partyka et al. . |
| 4,039,544 | 8/1977 | Broughton et al. . |
| 4,060,615 | 11/1977 | Matier et al. . |
| 4,079,057 | 3/1978 | Juby et al. . |
| 4,098,788 | 7/1978 | Crenshaw et al. . |
| 4,101,548 | 7/1978 | Crenshaw et al. . |
| 4,102,885 | 7/1978 | Crenshaw et al. . |
| 4,138,561 | 2/1979 | Crenshaw et al. . |
| 4,146,718 | 3/1979 | Jenks et al. . |
| 4,161,595 | 7/1979 | Kaplan et al. . |
| 4,171,363 | 10/1979 | Crenshaw et al. . |
| 4,208,521 | 6/1980 | Crenshaw et al. . |
| 4,209,623 | 6/1980 | Juby . |
| 4,423,075 | 12/1983 | Dvornik et al. . |
| 4,460,590 | 7/1984 | Möller . |
| 4,460,591 | 7/1984 | DeGraw et al. . |
| 4,880,810 | 11/1989 | Lowe, III et al. .............. 514/258 |
| 4,885,301 | 12/1989 | Coates . |
| 4,923,874 | 5/1990 | McMahon et al. .............. 514/258 |
| 5,073,559 | 12/1991 | Coates ...................... 514/262 |
| 5,147,875 | 9/1992 | Coates et al. . |
| 5,223,501 | 6/1993 | Chakravarty et al. .......... 514/258 |
| 5,250,535 | 10/1993 | Verheyden et al. ............ 514/262 |
| 5,254,571 | 10/1993 | Coates et al. . |
| 5,358,952 | 10/1994 | Moschel et al. ............... 514/262 |
| 5,401,774 | 3/1995 | Pamukcu et al. . |
| 5,439,895 | 8/1995 | Lee et al. ................... 514/259 |
| 5,614,530 | 3/1997 | Kumar et al. ................. 514/293 |
| 5,614,627 | 3/1997 | Takase et al. ................ 544/293 |

FOREIGN PATENT DOCUMENTS

| | | |
|---|---|---|
| 0 347 146 A2 | 12/1989 | European Pat. Off. . |
| 0 349 239 A2 | 1/1990 | European Pat. Off. . |
| 0 351058 | 1/1990 | European Pat. Off. . |
| 0 352960 A2 | 1/1990 | European Pat. Off. . |
| 0 395328 A2 | 10/1990 | European Pat. Off. . |
| 0 428268 A2 | 5/1991 | European Pat. Off. . |
| 0 463756 A1 | 1/1992 | European Pat. Off. . |
| 0 485157 A2 | 5/1992 | European Pat. Off. . |
| 0 485158 A2 | 5/1992 | European Pat. Off. . |
| 0 485171 A2 | 5/1992 | European Pat. Off. . |
| 0 485172 A2 | 5/1992 | European Pat. Off. . |
| 0 485173 A2 | 5/1992 | European Pat. Off. . |
| 0 508586 A1 | 10/1992 | European Pat. Off. . |
| 0 526004 A1 | 2/1993 | European Pat. Off. . |
| 0 607439 A1 | 7/1994 | European Pat. Off. . |
| 3038166 | of 1981 | Germany . |
| 274218 | 12/1989 | Germany . |
| 56-53659 | 5/1981 | Japan . |
| 57-167974 | 10/1982 | Japan . |
| 807826 | 1/1959 | United Kingdom . |
| 2063249 | 6/1981 | United Kingdom . |
| WO 92/03419 | 3/1992 | WIPO . |
| WO 93/07149 | 4/1993 | WIPO . |
| WO 93/12095 | 6/1993 | WIPO . |
| WO 94/05661 | 3/1994 | WIPO . |
| WO 97/03985 | 2/1997 | WIPO . |

OTHER PUBLICATIONS

Carter et al., Chemotherapy of Cancer, 2$^{nd}$ Ed., John Wiley & Sons, NY, NY, pp. 362–365 (1981).

Biddle, William et al., Antineoplastic Effect of the Pyrimido–Pyrimidine Derivative: RA 233, Pathologie Biologie, pp. 9–13 (Jan., 1984).

Mehta, Rajendra et al. Structure–Activity Relationships of Brassinin in Preventing the Development of Carcinogen–Induced Mammary lesions in Organ Culture, Anticancer Research 14: 1209–1214 (1994).

Waddell, W.R. et al., Am. J. Surgery, vol. 157, pp. 175–179 (1989).

Gonzaga, R.A.F. et al., The Lancet, Mar. 30, 1985, p. 751.

Waddell, W.R. et al., J. Surg. Oncology, vol. 24, pp. 83–87 (1983).

Federation Proceedings (1972) of the Federation of American Societies for Experimental Biology abstract Nos. 2044 and 2045.

Gilman, S.C. et al., Nonsteroidal Anti–inflammatory Drugs in Cancer Therapy, (circa 1985).

Brogden, R.N. et al., Drugs, vol. 16, pp. 97–114 (1978).

Hucker, H.B. et al., Drug Metabolism & Disposition, vol. 1, No. 6, pp. 721–736 (1973).

Shen, T.Y. et al., Chemical and Biological Studies on Indomethacin, Sulindac and Their Analogs, pp. 107–178 (circa 1975).

Duggan, D.E. et al., Clin. Pharm. & Therapeutics, vol. 21, No. 3, pp. 326–335 (1976).

Duggan, D.E. et al., J. Pharm. & Exper. Therap., vol. 201, No. 1, pp. 8–13 (1977).

(List continued on next page.)

Primary Examiner—Jerome D. Goldberg
Attorney, Agent, or Firm—Robert W. Stevenson

[57] ABSTRACT

Derivatives of quinazoline are useful for the treatment of patients having precancerous lesions. These compounds are also useful to inhibit the growth of neoplastic cells.

10 Claims, No Drawings

OTHER PUBLICATIONS

Glavin, G.B. et al., Toxicology and Applied Pharmacology, vol. 83, pp. 386–389 (1986).

Moorghen, M. et al., Journal of Pathology, vol. 156, pp. 341–347 (1988).

Moorghen, M. et al., Acta Histochemica, Suppl.–Band XXIX, S. 195–199 (1990).

Bjarnason et al., Gastroenterology, vol. 94, No. 4, pp. 1070–1074 (1988).

Badrieh, Y., et al., Chem. Ber., vol. 125, pp. 667–674 (1992).

Silvola, J. et al., Effects of nonsteroidal anti–inflammatory drugs on rat gastric mucosal phosphodiesterase activity, Agents and Actions, vol. 12.4, pp. 516–520 (1982).

Curtis–Prior, P.B. et al., Cyclic Nucleotide Phosphodiesterase Activity of Human Normal and Carcinomatous Lung Tissue, The Lancet, pp. 1225–1225 Dec. 4, 1976.

Pepin, P. et al., Effects of Sulindac and Oltipraz on the tumorigenicity of 4–(methylnitrosamino)1–(3–pyridyl)–1–Butanone in A/J mouse lung, Carcinogenesis, vol. 13, No. 3, pp. 341–348 (1992).

Nicholson, C.D. et al. Differential modulation of tissue function and therapeutic potential of selective inhibitors of cyclic nucleotide phosphodiesterase isoenzymes, Trends Pharmacol. Sci. (TiPS), vol. 12, pp. 19–27 (1991).

Ahn, H.S. et al., Effects of Selective Inhibitors on Cyclic Nucleotide Phosphodiesterases of Rabbit Aorta, Biochemical Pharmacology, vol. 38, No. 19, pp. 3331–3339 (1989).

Luginer, C. et al., Selective Inhibition of Cyclic Nucleotide Phosphodiesterases of Human, Bovine and Rat Aorta, Biochem. Pharmacology, vol. 35, No. 10, pp. 1743–1751 (1986).

Turner, N.C. et al., Relaxation of guinea–pig trachea by cyclic AMP phosphodiesterase inhibitors and their enhancement by sodium mitroprusside, Br. J. Pharmacol. vol. III, pp. 1047–1052 (1994).

Weishaar, R.E. et al., Multiple Molecular Forms of Cyclic Nucleotide Phosphodiesterase in Cardiac and Smooth Muscle and In Platelets, Biochem. Pharmacology, vol. 35, No. 5, pp. 787–800 (1986).

Murray, K.J. et al., Potential Use of Selective Phosphodiesterase Inhibitors in the Treatment of Asthma, New Drugs for Asthma Therapy, Birkhauser Verlag Basel, pp. 27–46 (1991).

Saeki, T. et al., Isolation of Cyclic Nucleotide Phosphodiesterase Isozymes From Pig Aorta, Biochem. Pharmacology, vol. 46, No. 5, pp. 833–839 (1993).

Turner, N.C. et al., Pulmonary effects of type V cyclic GMP specific phosphodiesterase inhibition in anaesthetized guinea–pig, Br. J. Pharmacol., vol. 111, 1198–1204 (1994).

Ferreira, S.H. et al., The molecular mechanism of action of peripheral morphone analgesia: stimulation of the cGMP system via nitric oxide release, European Journal of Pharmacology, 201 pp. 121–122 (1991).

Hidaka, H. et al., Selective Inhibitors of Three Forms of Cyclic Nucleotide Phosphodiesterase—Basic and Potential Clinical Applications, vol. 16, Advances in Cyclic Nucleotide and Protein Phosphorylation Research, pp. 245–259 (1984).

Tulshian, D. et al., Synthesis and Phosphodiesterase Activity of Carboxylic Acid Mimetics of Cyclic Guanosine 3',5'–Monophosphate, J. Med. Chem, vol. 36, 1210–1220 (1993).

Yasumoto, T. et al., Properties of Base–Substituted and Carboxyl–Esterified Analogues of Griseolic Acid, a Potent cAMP Phosphodiesterase Inhibitor, Biochemical Pharmacology, vol. 43, No. 10, pp. 2073, 2081 (1992).

Broughton, B.J. et al., Antiallergic Activity of 2–Phenyl–8–azapruin–6–ones, Journal of Medicinal Chemistry, vol. 18, No. 11, pp. 1117–1118 (1975).

Kodama, K. et al., Effects of a novel, selective and potent phosphodiesterase type V inhibitor, E4021, on myocardial ischemia in guinea pigs, Euro. J. of Pharma. 263, pp. 93–99 (1994).

Zacharski, L. R. et al., Effect of Mopidamol on Survival in Carcinoma of the Lung and Colon: Final Report of Veterans Administration Cooperative Study No. 188, J. of the Nat'l Cancer Inst., vol. 80, No. 2, pp. 90–96 (1988).

Lichtner, R. B. et al., The Pyrimido–pyrimidine Derivatives RA 233 adn RNA RA 85 affect Growth and Cytoskeletal Organization of Rat Mammary Adenocarcinoma Cells, Eur. J. Cancer Clin. Oncol., vol. 23, No. 9, pp. 1269–1275 (1987).

Janik, P. et al., Inhibition of Growth of Primary and Metastatic Lewis Lung Carcinoma Cells by the Phosphodiesterase Inhibitor Isobutylmethylxanthine, Cancer Res. vol. 40, pp. 1950–1954, (Jun., 1980).

Bergstrand, Hakan et al., Effects of Antiallergic Agents, Compound 48/80, and Some Reference Inhibitors on the Activity of Partially Purified Human lung Tissue Adenosine Cyclic 3',5'–Monophosphate and Guanosine Cyclic 3',5'–Monophosphate Phosphodiesterases, Molecular Pharmacology, 13, pp. 38–43 (1976).

Drees, Markus et al., 3',5'–Cyclic Nucleotide Phosphodiesterase in Tumor Cells as Potential Target for Tumor Growth Inhibition, Cancer Research 53, pp. 3058–3061 (1993).

Semmler, J. et al., Xanthine derivatives: comparison between suppression of tumor necrosis factor–x production and inhibition of cAMP phosphodiesterase activity, Immunology 78, pp. 520–525 (1993).

Clarke, W.R. et al., The type III phosphodiesterase inhibitor milrinone and type V PDE inhibitor dipyridamole individually and synergistically reduce elevated pulmonary vascular resistance (Abstract Only), Pulm. Pharmacol., 7(2), pp. 81–89, (1994).

Raeburn, David et al., Effects of isoenzyme–selective inhibitors of cyclic nucleotide phosphodiesterase on microvascular leak in guinea pig airways in vivo (Abstract Only), J. Pharmacol. Exp. Ther., 267(3), pp. 1147–1151 (1993).

Marcoz, P. et al., Modulation of rat thymocyte proliferative response through the inhibition of different cyclic nucleotide phosphodiesterase isoforms by means of selective inhibitors and cGMP–elevating agents (Abstract Only), Mol. Pharmacol. 44(5) pp. 1027–1035 (1993).

Barnett, Mary S. et al., Initial biochemical and functional characterization of cyclic nucleotide phosphodiesterase isozymes in canine colonic smooth muscle (Abstract Only), J. Pharmacol. Exp. Ther., 264(2) pp. 801–812 (1993).

Molnar–Kimber, K. et al., Modulation of TNFa and IL–1B from indotoxin–stimulated monocytes by selective PDE isozyme inhibitors (Abstract Only), Agents Actions 39(Spec. Conf. Issue), C77–C79 (1993).

Giorgi, Mauro et al., Characterization of 3',5' cyclic nucleotide phosphodiesterase activities of mouse neuroblastoma N18TG2 cells (Abstract Only), FEBS Lett. 324(1) pp. 76–80 (1993).

Porter, Roderick et al., Preparation of 6-phenyl-3-(5-tetrazoly)pyridin-2(H)-one derivatives as cyclic AMP-dependent protein kinase agonists (Abstract Only), PCT Int. Appl. WO9206085 A1, (Sep. 26, 1991).

Molnar-Kimber, K. L. et al., Differential regulation of TNF-a and IL-1B production from endotoxin stimulated human monocytes by phosphodiestersae inhibitors (Abstract Only), Mediators Inflammation 1(6) pp. 411–417 (1992).

Radomski, Marek W. et al., human Colorectal adenocarcinoma cells; differential nitric oxide synthesis determines their ability of aggregate platelets (Abstract Only), Cancer Res. 51(22) pp. 6073–6078 (1991).

Anderson, Thomas L. G. et al., Interactions between isoprenaline, sodium nitroprusside, and isozyme-selective phosphodiesterase inhibitors on ADP-induced aggretation and cyclic Nucleotide levels in human platelets (Abstract Only), J. Cardiovasc. Pharmacol. 18(2) pp. 237–242 (1991).

Souness, John E. et al., Role of Selective cyclic GMP phosphodiestersae inhibition in the myorelaxant actions of M&B 22, 943, MY-5445, vinpocetine and 1-methyl-3-isobutyl-8-(methylamino)xanthine (Abstract Only), Br. J. Pharmacol. 98(3) pp. 725–734 (1989).

Lichtner, Rosemarie B., The pyrimidopyrimidine derivatives RA233 and RX-RA85 affect cell cycle distribution of two murine tumor cell lines (Abstract Only), Eur. J. Cancer Clin. Oncol. 25(6), pp. 945–951 (1989).

Mamytbekova, A., et al., Antimetastatic effect of flurbiprofen and other platelet aggregation inhibitors (Abstract Only), Neoplasma 33(4), pp. 417–421 (1986).

Hagiwara, Masatoshi et al., Effect of 1-(3-chloroantilino)-4-phenylpthalazine (MY-5445), a specific inhibitor of cyclic CMP Phosphodiesterase, on human platelet aggregation (Abstract Only), J. Pharmacol. Exp. Ther. 229(2) pp. 467–471 (1984).

Mehta, Rajendra et al., Structure-Activity Relationships of Brassinin in Preventing the Development of Carcinogen-Induced Mammary Lesions in Organ Culture, Anticancer Research 14: 1209–1214 (1994).

METHOD OF TREATING A PATIENT HAVING A PRECANCEROUS LESIONS WITH AMIDE QUINAZOLINE DERIVATIVES

This application is a continuation of application Ser. No. 08/475,197, filed Jun. 7, 1995, now abandoned.

TECHNICAL FIELD

This invention relates to methods for treatment or prevention of precancerous lesions.

BACKGROUND OF THE INVENTION

Each year in the United States alone, untold numbers of people develop precancerous lesions. These lesions exhibit a strong tendency to develop into malignant tumors, or cancer. Such lesions include lesions of the breast (that can develop into breast cancer), lesions of the skin (that can develop into malignant melanoma or basal cell carcinoma), colonic adenomatous polyps (that can develop into colon cancer), and other such neoplasms. Compounds which prevent or induce the remission of existing precancerous or cancerous lesions or carcinomas would greatly reduce illness and death from cancer.

Approximately 60,000 people die from colon cancer, and over 150,000 new cases of colon cancer are diagnosed each year. For the American population as a whole, individuals have a six percent lifetime risk of developing colon cancer, making it the second most prevalent form of cancer in the country. Colon cancer is also prevalent in Western Europe. It is believed that increased dietary fat consumption is increasing the risk of colon cancer in Japan.

In addition, the incidence of colon cancer reportedly increases with age, particularly after the age of 40. Since the mean ages of populations in America and Western Europe are increasing, the prevalence of colorectal cancer should increase in the future.

To date, little progress has been made in the prevention and treatment of colorectal cancer, as reflected by the lack of change in the five-year survival rate over the last few decades. The only cure for this cancer is surgery at an extremely early stage. Unfortunately, most of these cancers are discovered too late for surgical cure. In many cases, the patient does not experience symptoms until the cancer has progressed to a malignant stage.

In view of these grim statistics, efforts in recent years have concentrated on colon cancer prevention. Colon cancer usually arises from pre-existing benign neoplastic growths known as polyps. Prevention efforts have emphasized the identification and removal of colonic polyps. Polyps are identified by x-ray and/or colonoscopy, and usually removed by devices associated with the colonoscope. The increased use of colon x-rays and colonoscopies in recent years has detected clinically significant precancerous polyps in four to six times the number of individuals per year that acquire colon cancer. During the past five years alone, an estimated 3.5 to 5.5 million people in the United States have been diagnosed with adenomatous colonic polyps, and it is estimated that many more people have or are susceptible to developing this condition, but are as yet undiagnosed. In fact, there are estimates that 10–12 percent of people over the age of 40 will form clinically significant adenomatous polyps.

Removal of polyps has been accomplished either with surgery or fiber-optic endoscopic polypectomy—procedures that are uncomfortable, costly (the cost of a single polypectomy ranges between $1,000 and $1,500 for endoscopic treatment and more for surgery), and involve a small but significant risk of colon perforation. Overall, about $2.5 billion is spent annually in the United States in colon cancer treatment and prevention.

As indicated above, each polyp carries with it a chance that it will develop into a cancer. The likelihood of cancer is diminished if a polyp is removed. However, many of these patients demonstrate a propensity for developing additional polyps in the future. They must, therefore, be monitored periodically for the rest of their lives for polyp reoccurrence.

In most cases (i.e. the cases of so-called common sporadic polyps), polyp removal will be effective to reduce the risk of cancer. In a small percentage of cases (i.e. the cases of the so-called polyposis syndromes), removal of all or part of the colon is indicated. The difference between common sporadic polyps and polyposis syndromes is dramatic. Common sporadic polyp cases are characterized by relatively few polyps, each of which can usually be removed leaving the colon intact. By contrast, polyposis syndrome cases can be characterized by many (e.g. hundreds or more) of polyps— literally covering the colon in some cases—making safe removal of the polyps impossible short of surgical removal of the colon.

Because each polyp carriers with it the palpable risk of cancerous development, polyposis syndrome patients invariably develop cancer if left untreated. Surgical removal of the colon is the conventional treatment. Many of these patients have undergone a severe change in lifestyle as a result of the disfiguring surgery. Patients have strict dietary restrictions, and many must wear ostomy appliances to collect their intestinal wastes.

The search for drugs useful for treating and preventing cancer is intensive. Indeed, much of the focus of cancer research today is on the prevention of cancer because therapy is often not effective and has severe side effects. Cancer prevention is important for recovered cancer patients who retain a risk of cancer reoccurrence. Also, cancer prevention is important for people who have not yet had cancer, but have hereditary factors that place them at risk of developing cancer. With the development of new diagnostic screening technologies, it is possible to identify those with high risk factors, such as the potential for polyposis syndrome, who would greatly benefit from chemopreventive drugs. Therefore, finding such anti-cancer drugs that can be used for prolonged preventive use is of vital interest to many people.

One way to find such drugs is to screen thousands of compounds for the same biological activity found in known chemopreventive and chemotherapeutic drugs. Most such drugs are now believed to kill cancer cells by inducing apoptosis, or as sometimes referred to as "programmed cell death." Apoptosis naturally occurs in virtually all tissues of the body, and especially in self-renewing tissues such as bone marrow, gut, and skin. Apoptosis plays a critical role in tissue homeostasis, that is, it ensures that the number of new cells produced are correspondingly offset by an equal number of cells that die. For example, the cells in the intestinal lining divide so rapidly that the body must eliminate cells after only three days in order to prevent the overgrowth of the intestinal lining.

Recently, scientists have realized that abnormalities of apoptosis can lead to the formation of precancerous lesions and carcinomas. Also, recent research indicates that defects in apoptosis plays a major role in other diseases in addition to cancer. Consequently, compounds that modulate apoptosis could be used to prevent or control cancer, as well as used in the treatment of other diseases.

Unfortunately, even though known chemotherapeutic drugs may exhibit such desirable apoptotis effects, most chemotherapeutic drugs have serious side effects that prohibit their long term use, or use in otherwise healthy individuals with precancerous lesions. These side effects, which are a result of the high levels of cytotoxicity of the drugs, include hair loss, weight loss, vomiting and bone marrow immune suppression. Therefore, there is a need to identify new drug candidates for therapy that do not have such serious side effects in humans.

SUMMARY OF THE INVENTION

This invention is a method of treating patients with precancerous lesions or neoplasms by administering a pharmacologically effective amount of a compound of Formula I below to a patient in need of such treatment. Such compositions are effective in modulating apoptosis, and eliminating and inhibiting precancerous lesions, and neoplastic cells.

DETAILED DESCRIPTION OF THE PRESENTLY PREFERRED EMBODIMENTS

As discussed above, one embodiment of this invention is a method of treating a patient with precancerous lesions or neoplasms by administering a pharmacologically effective amount of a compound of formula I below:

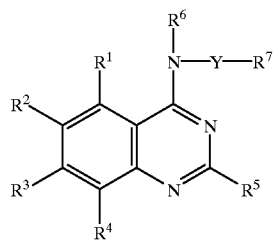

(I)

wherein R1, R2, R3 and R4, each of which may be the same or different, are selected from a hydrogen atom, a alkoxy group having 1 to 6 carbon atoms, a hydroxyalkyl group, a cyano group, an acylamino group, a carboxyl group which may be protected or two of R1, R2, R3 or R4 may together form methylenedioxy, ethylenedioxy, or a phenyl ring;

R5 is selected from a hydrogen atom, a halogen atom, a hydroxyl group, a hydrazino group, an alkyl group having 1 to 6 carbon atoms, an alkoxy group having 2 to 8 carbon atoms, an alkenyl group which may be protected having 2 to 8 carbon atoms, a carboxyalkenyl group which may be protected having 3 to 8 carbon atoms, a hydroxyalkyl group having 1 to 6 carbon atoms, or a carboxyl group which may be protected, R6 is selected from a hydrogen atom, a alkyl group having 1 to 6 carbon atoms, an acyl group, a lower alkoxyalkyl group having 2 to 8 carbon atoms, a carboxyalkyl group having 2 to 8 carbon atoms which may be protected or a hydroxyalkyl group having 2 to 8 carbon atoms;

R7 is selected from a hydrogen atom, a hydroxyl group, a carboxyl group which may be protected, a cyano group, an acyl group, a heteroaryl group which may be substituted or a benzyl group which may be substituted, said substitutions, which may be the same or different, are selected from a hydrogen atom, a halogen atom, a hydroxyl group, an amino group, a nitro group, a alkyl group having 1 to 6 carbon atoms, a alkoxy group having 1 to 6 carbon atoms, a alkoxyalkyl group having 2 to 8 carbon atoms, a alkenyl group having 2 to 8 carbon atoms, an acyl group an acylamino group, an alkylsulfonylamino group, a hydroiminoalkyl group, an alkyloxy-carbonylamino group, an alkyloxybarbonyloxy group or a heteroaryl group which may be substituted: or two of said substitutions may together form a saturated or unsaturated ring which may contain a nitrogen, a sulfur atom or an oxygen atom; and Y is a group represented by the formula —(CH2)q— wherein q is 0 or an integer of 1 to 8, when q is an integer of 1 to 8, each carbon atom may have from 1 to 2 substituents, or Y is a group represented by the formula:

Preferably, R1, R2, R3, and R4, each of which may be the same or different from one another, are selected from a hydrogen atom, a cyano group, a halogen atom, or a lower alkoxy group. More preferably, one of R1, R2, R3 and R4 is a cyano group, a chlorine atom or a methoxy atom. Still more preferably, R2 is a halogen atom. Most preferably, R2 is a chlorine atom and R1, R3 and R4 are hydrogen atoms. Also, it is preferred that R5 or R6 be a hydrogen atom.

When Y is a group represented by the formula —(CH2)q—, it is preferred that q is an integer of 1 to 8. In such compounds, preferably, R7 is a benzyl group which may be substituted, said substitutions, each of which may be the same or different, are each selected from a hydrogen atom, a halogen atom, a hydroxy group, an amino group, a nitro group, a lower alkyl group, a lower alkoxy group, a lower alkoxyalkyl group, a lower alkenyl group, an acyl group, an acylamino group, an alkylsulfonylamino group, a hydroxyiminoalkyl group, an alkyloxycarbonylamino group, an alkyloxycarbonyloxy group or a heteroaryl group which may be substituted, or two of the substitutions may together form a saturated or unsaturated ring which may contain nitrogen atoms, sulfur atoms or oxygen atoms; and q is an integer of 1 to 8. More preferably, R7 is a group represented by the formula:

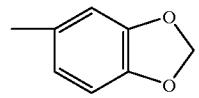

"Alkyl group" refers to straight or branched chain $C_1$–$C_{12}$ groups such as methyl, ethyl, propyl, iso-propyl, n-butyl, t-butyl and amyl. "Alkoxy group" refers to hydroxy-substituted alkyl groups such as methoxy, ethoxy, propoxy, butoxy and amyloxy. "Alkoxycarbonyl group" refers to carbonyl-substituted alkoxy groups such as methoxycarbonyl, ethoxycarbonyl, propoxycarbonyl, butoxycarbonyl, amyloxycarbonyl, etc. "Alkylcarbonyl group" refers to carbonyl-substituted alkyl groups such as acetyl, propionyl, butyryl or others. "Halogen" refers to fluorine, chlorine, bromine and iodine.

The compound represented by the formula [I] can also form a pharmaceutically acceptable salt through the reaction of the basic nitrogen thereof with an acid. For example, there may be mentioned salts with mineral acids such as hydrogen chloride, sulfuric acid, hydrobrobromic acid, phosphoric acid, etc. or methanesulfonic acid, toluenesulfonic acid, benzenesulfonic acid, acetic acid, glycolic acid, glucuronic acid, maleic acid, oxalic acid, ascorbic acid, citric acid, salicylic acid, and so on.

As used herein, the term "precancerous lesion" refers to lesions that exhibit histologic changes which are associated with an increased risk of cancer development. Examples include adenomatous polyps of the colon, dysplastic nevi of the skin and atypical hyperplasia of the breasts. Certain syndromes that commonly display precancerous lesions are also referred to by the term "precancerous" including dysplastic nevus syndrome and the colonic polyposis syndromes. "Precancerous" refers to these lesions or syndromes of various tissues whether or not the lesions are clinically identifiable.

As used herein, the term "carcinomas" refers to lesions which are cancerous. Examples include malignant melanomas, breast cancer, and colon cancer.

As used herein, the term, "neoplasm" refers to both precancerous and cancerous lesions.

As used herein, the term "halo" or "halogen" refers to chloro, bromo, fluoro and iodo groups, and the term "alkyl" refers to straight, branched or cyclic alkyl groups.

In another form, the present invention is also a method of treating individuals with precancerous lesions by administering a pharmaceutically effective amount of an enterically coated compounds of formula I above where $R^1$–$R^7$ are as defined above.

Compounds of formula I may be formulated into compositions together with pharmaceutically acceptable carriers for oral administration in solid or liquid form, or for rectal administration, although carriers for oral administration are most preferred.

Pharmaceutically acceptable carriers for oral administration include capsules, tablets, pills, powders, troches and granules. In such solid dosage forms, the carrier can comprise at least one inert diluent such as sucrose, lactose or starch. Such carriers can also comprise, as is normal practice, additional substances other than diluents, e.g., lubricating agents such as magnesium stearate. In the case of capsules, tablets, troches and pills, the carriers may also comprise buffering agents. Carriers such as tablets, pills and granules can be prepared with enteric coatings on the surfaces of the tablets, pills or granules. Alternatively, the enterically coated compound can be pressed into a tablet, pill, or granule, and the tablet, pill or granules for administration to the patient. Preferred enteric coatings include those that dissolve or disintegrate at colonic pH such as shellac or Eudraget S.

Pharmaceutically acceptable carriers include liquid dosage forms for oral administration, e.g. pharmaceutically acceptable emulsions, solutions, suspensions, syrups and elixirs containing inert diluents commonly used in the art, such as water. Besides such inert diluents, compositions can also include adjuvants such as wetting agents, emulsifying and suspending agents, and sweetening, flavoring and perfuming agents.

Pharmaceutically acceptable carriers for rectal administration are preferably suppositories which may contain, in addition to the compounds of Formula I, excipients such as cocoa butter or a suppository wax.

The pharmaceutically acceptable carrier and compounds of Formula I are formulated into unit dosage forms for administration to a patient. The dosage levels of active ingredient (i.e. compounds of Formula I) in the unit dosage may be varied so as to obtain an amount of active ingredient effective to achieve polyp-eliminating activity in accordance with the desired method of administration (i.e. oral or rectal). The selected dosage level therefore depends upon the nature of the active compound administered, the route of administration, the desired duration of treatment, and other factors. If desired, the unit dosage may be such that the daily requirement for active compound is in one dose, or divided among multiple doses for administration, e.g. two to four times per day.

In still another form, the invention is a method of inhibiting the growth of neoplastic cells by exposing them to an effective amount of the compound of formula [I] above.

In yet another form, the invention is a method of inducing apoptosis in human cells by exposing those cells to an effective amount of the compound of formula [I] above where such cells are sensitive to this compound.

Additionally, in yet another form, the invention is a method of treating a patient having a disease which would benefit from regulation of apoptosis by treating the patient with an effective amount of the compound of formula [I] above. The regulation of apoptosis is believed to play an important role in diseases associated with abnormalities of cellular growth patterns such as benign prostatic hyperplasia, neurodegenerative diseases such as Parkinson's disease, autoimmune diseases including multiple sclerosis and rheumatoid arthritis, and infectious diseases such as AIDS.

The foregoing may be better understood from the following examples, which are presented for purposes of illustration and are not intended to limit the scope of the invention. As used in the following examples, the references to substituents such as R, $R^1$, $R^2$ etc., refer to the corresponding compounds and substituents in the Formula above.

The pharmacologically acceptable salt includes inorganic acid salts such as hydrochloride, hydrobromide, sulfate and phosphate; organic acid salts such as acetate, maleate, tartrate, methanesulfonate, benzenesulfonate and toluenesulfonate; and amino acid salts such as argininate, aspartate and glutamate. Further, some of the compounds may form metal salts such as Na, K, Ca or Mg, and the pharmacologically acceptable salt of the present invention also includes these metal salts.

Although the compound of the present invention may be present as various isomers including geometrical isomers, i.e., cis-isomer and trans-isomer. and optical isomers, i.e., d-isomer and l-isomer depending upon the kinds and combination of the substituents, it is needless to say that the compounds of the present invention include all of the isomers.

Preferable specific examples of the compound of the present invention will now be described in order to facilitate the understanding of the present invention, though it is needless to say that the compounds of the present invention are not limited to these examples.

PREPARATION PROCESS

Representative processes for the preparation of the compound according to the present invention will now be described below. A representative quinazoline skeleton as shown below is useful for the purpose of describing these processes.

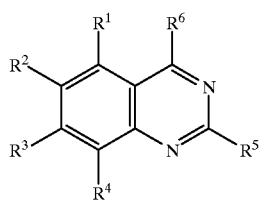

Though compounds having a quinazoline skeleton are mainly described in the following explanation, the following explanation can be applied for compounds having a skeleton other than the quinazoline skeleton.

Preparation Process 1

When $R^5$ is a hydrogen atom, a halogen atom or a group selected from among those which are directly bonded to the quinazoline skeleton through a carbon atom in the general formula (I), a compound represented by the general formula (I) can also be prepared by the following process:

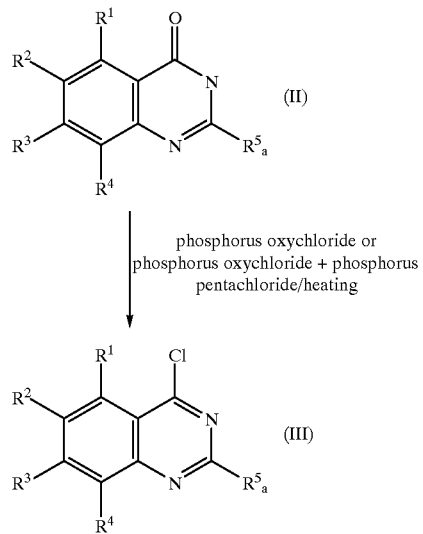

(in a series of formulas, $R^5_a$ is a hydrogen atom, a halogen atom or a group selected from among those which are directly bonded to the quinazoline skeleton through a carbon atom in $R^5$ described above; and $R^1$, $R^2$, $R^3$ and $R^4$ are each as defined above.

That is, this process is one for preparing a quinazoline derivative represented by the general formula (III) by reacting a quinazoline derivative represented by the general formula (II) with phosphorus oxychloride or by reacting it with phosphorus oxychloride in the presence of phosphorus pentachloride under heating.

Preparation Process 2

When $R^5$ is a group selected from among a hydrogen atom, a halogen atom, a group represented by the formula:

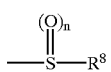

(wherein $R^8$ and m are each as defined above), a group represented by the formula —O—$R^9$ (wherein $R^9$ is as defined above), a heteroaryl group which may be substituted and a group which is directly bonded to the ring through a carbon atom (for example, a lower alkyl group, a carboxyl group which may be protected, a 1,3-benzodioxolyl group which may be substituted, a 1,4-benzodioxyl group which may be substituted, a 1,3-benzodioxolylalkyl group which may be substituted and a 1,4-benzodioxylalkyl group which may be substituted); and $R^6$ is a group selected from among those defined above with respect to $R^6$ except a hydrogen atom, halogen atoms and lower alkyl groups in the general formula (I), a compound represented by the general formula (I) can be prepared by the following process:

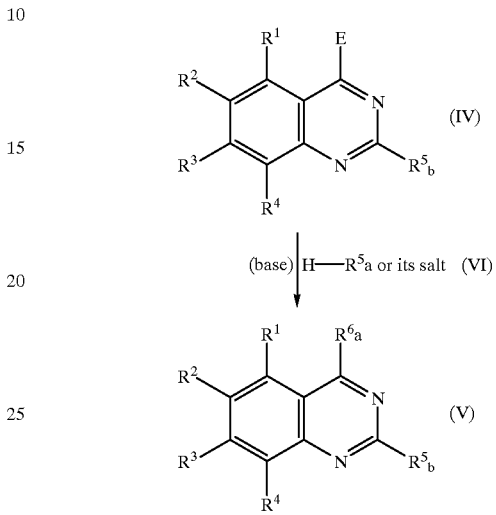

[in a series of formulas $R^1$, $R^2$, $R^3$ and $R^4$, are each as defined above; $R^5_b$ represents a group selected from among a hydrogen atom, a halogen atom, a group represented by the formula $$\overset{(O)_n}{\underset{\|}{S}}-R^8$$

(wherein $R^8$ and m are each as defined above), a group represented by the formula —O—$R^9$ (wherein $R^9$ is as defined above), a heteroaryl group which may be substituted and a group which is directly bonded to the ring through a carbon atom (for example, a lower alkyl group, a carboxyl group which may be protected, a 1,3-benzodioxolyl group which may be substituted, a 1,4-benzodioxyl group which may be substituted, a 1,3-benzodioxylalkyl group which may be substituted and 1,4-benzodioxylalkyl group which may be substituted); $R^6_a$ represents a group selected from among those defined above with respect to $R^6$ except hydrogen atom, halogen atoms and lower alkyl groups; and E represents an eliminable group].

That is, this process is one for preparing an objective compound (V) by condensing a quinazoline derivative represented by the general formula (IV) with a compound represented by the general formula (VI).

The eliminable group represented by E in the formula includes halogen atoms and alkoxy groups.

This process may be conducted in the presence of a base at need.

The base includes organic bases such as triethylamine, pyridine and diisopropylethylamine; inorganic bases such as sodium carbonate, potassium carbonate, sodium hydrogencarbonate, sodium hydroxide and sodium hydride; and alkoxides such as sodium methoxide and potassium t-butoxide.

As the reaction solvent, every solvent which is inert to the reaction can be used and examples thereof include ethanol, isopropyl alcohol, tetrahydrofuran, dimethylformamide and dimethyl sulfoxide. This process can be conducted even in the absence of any solvent in some cases.

The reaction temperature preferably ranges from −20 to 300° C.

Preparation Process 3

When $R^5$ is a group selected from among those defined above with respect to $R^5$ except a hydrogen atom, halogen atoms and groups which are directly bonded to the quinazoline skeleton through a carbon atom; and $R^6$ is a group selected from among those defined above with respect to $R^6$ except halogen atoms in the general formula (I), a compound represented by the general formula (I) can be prepared by the following process:

$$\text{(VII)}$$

$$H\text{—}R^5c \text{ or its salt } \quad (IX)$$

$$\text{(VIII)}$$

(in a series of formulas, $R^1$, $R^2$, $R^3$ and $R^4$ are each as defined above; $R^5_c$ is a group selected from among those defined above with respect to $R^5$ except a hydrogen atom, halogen atoms and groups which are directly bonded to the quinazoline skeleton through a carbon atom;

$R^6_b$ is a group selected from among those defined above with respect to $R^6$, except halogen atoms; and F represents an eliminable group).

That is, this process is one for preparing an objective compound (VIII) by condensing a compound represented by the general formula (VII) with a compound represented by the general formula (IX).

The eliminable group represented by F in the formula includes, for example, halogen atoms, alkylthio groups and so forth.

This process may be conducted in the presence of a base at need.

The base includes organic bases such as triethylamine, pyridine and diisopropylethylamine; inorganic bases such as sodium carbonate, potassium carbonate, sodium hydrogencarbonate, sodium hydroxide and sodium hydride; and alkoxides such as sodium methoxide and potassium t-butoxide.

As the reaction solvent, every solvent which is inert to the reaction can be used and examples thereof include ethanol, isopropanol, tetrahydrofuran, dimethylformamide and dimethyl sulfoxide.

The reaction temperature preferably ranges from 0 to 300° C.

Preparation Process 4

When $R^5$ is a group represented by the formula $$-\overset{\overset{\displaystyle O}{\|}}{C}-R^{24}$$

(wherein $R^{24}$ is a hydrogen atom or a lower alkyl group in the general formula (I), a compound represented by the general formula (I) can also be prepared by the following process:

$$\text{(X)}$$

reducing agent $$\text{(XII)}$$

reducing agent or nucleophilic reagent oxidizing agent $$\text{(XI)}$$

(in a series of formulas, $R^1$, $R^2$, $R^3$ and $R^4$ and $R^6$ are each as defined above; and $R^{24}$ and $R^{25}$, each of which may be the same or different from each other, represent each a hydrogen atom or a lower alkyl group).

That is, this process is one for preparing an objective compound (XI) by reacting a compound represented by the general formula (X) with an ordinary reducing agent or an ordinary nucleophilic reagent, either directly or through the oxidation of an alcohol (XII).

The reducing agent includes lithium aluminum hydride, sodium borohydride, diisobutylaluminum hydride and so forth.

The nucleophilic reagent includes lower alkyl metals such as methyllithium, methylmagnesium bromide and so forth.

The oxidizing agent to be used when the reaction is conducted through the alcohol (XII) includes potassium bichromate/sulfuric acid, dimethyl sulfoxide/oxalyl chloride and so forth.

As the reaction solvent, every solvent which is inert to the reaction can be used.

The reaction temperature ranges from 0° C. to the refluxing temperature of the solvent.

Preparation Process 5

When $R^5$ is a group represented by the formula $$-\underset{\underset{\displaystyle R^{24}}{|}}{C}=N-OR^{10}$$

(wherein $R^{10}$ and $R^{24}$ are each as defined above) in the general formula (I), a compound represented by the general formula (I) can also be prepared by the following process:

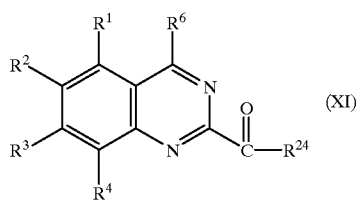

(XI)

↓ NH₂OH

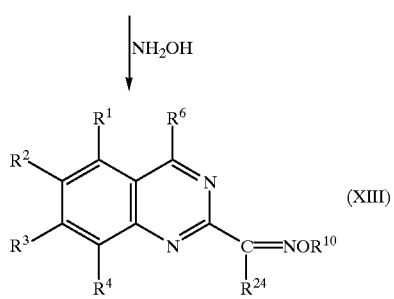

(XIII)

(in a series of formulas, $R^1$, $R^2$, $R^3$, $R^4$, $R^6$, $R^{10}$ and $R^{24}$ are each as defined above).

That is, this process is one for preparing a compound represented by the formula (XIII) by reacting a compound represented by the general formula (XI) with hydroxyamine.

As the reaction solvent, every solvent which is inert to the reaction can be used.

The reaction temperature ranges from 0° C. to the refluxing temperature of the solvent.

Preparation Process 6

When $R^5$ is a group represented by the formula

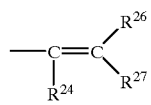

(wherein $R^{24}$ is as defined above; $R^{26}$ represents a hydrogen atom or a lower alkyl group; and $R^{27}$ represents a hydrogen atom, a lower alkyl group, a carboxyl group which may be protected or a carboxyalkyl group which may be protected) in the general formula (I), a compound represented by the formula (I) can also be prepared by the following process:

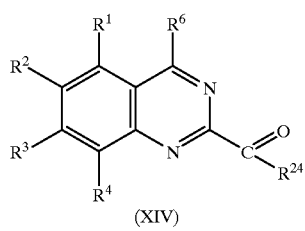

(XIV)

↓

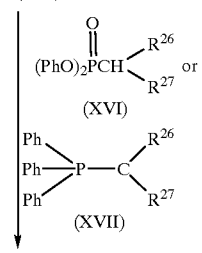

(XVI)

or (XVII)

↓

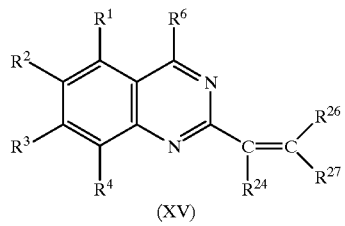

(XV)

(in a series of formulas, $R^1$, $R^2$, $R^3$, $R^4$, $R^6$, $R^{24}$, $R^{26}$ and $R^{27}$ are each as defined above; and Ph represents a phenyl group).

That is, this process is one for preparing a compound represented by the general formula (XV) by reacting a compound represented by the general formula (XIV) with a compound represented by the general formula (XVI) or the general formula (XVII) through the Wittig reaction.

As the reaction solvent, every solvent which is inert to the reaction can be used.

The reaction temperature ranges from 0° C. to the refluxing temperature of the solvent.

Preparation Process 7

When $R^5$ is a group represented by the formula

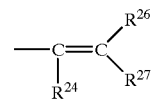

(wherein $R^{24}$, $R^{26}$, and $R^{27}$ are each as defined above) in the general formula (I), a compound represented by the formula (I) can also be prepared by the following process:

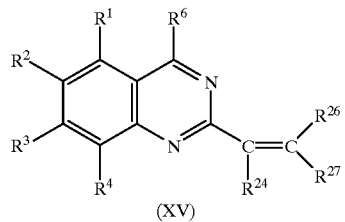

(XV)

↓ Pd—C or Pt

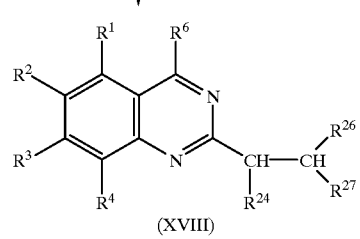

(XVIII)

(in a series of formulas, $R^1$, $R^2$, $R^3$, $R^4$, $R^6$, $R^{24}$, $R^{26}$ and $R^{27}$ are each as defined above).

That is, this process is one for preparing an objective compound (XVIII) by reducing the compound represented by the general formula (XV) prepared in the Preparation process 6.

The reduction can be conducted by conventional means, for example, catalytic reduction using palladium/carbon or platinum catalyst.

As the reaction solvent, every solvent which is inert to the reaction is used.

Preparation Process 8

When $R^6$ is a group represented by the formula

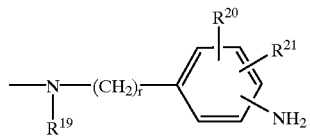

(wherein $R^{19}$, $R^{20}$, $R^{21}$ and r are each as defined above) in the general formula (I), a compound represented by the general formula (I) can also be prepared by the following process:

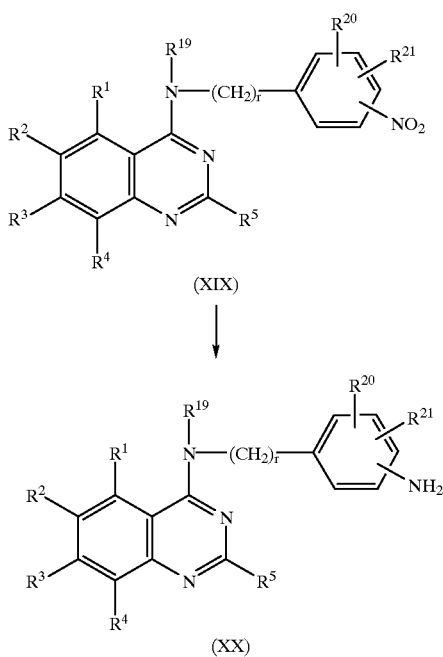

(in a series of formulas, $R^1$, $R^2$, $R^3$, $R^4$, $R^5$, $R^{19}$, $R^{20}$, $R^{21}$ and r are each as defined above).

That is, this process is one for preparing an objective compound (XX) by reducing a compound represented by the general formula (XIX).

The reduction is conducted by conventional means, e.g., catalytic reduction using palladium/carbon or platinum catalyst or reduction with iron or tin.

As the reaction solvent, every solvent which is inert to the reaction can be used.

Preparation Process 9

When $R^5$ is a group represented by the formula —O—$R^9$ (wherein $R^9$ is a carboxyl group which may be protected) in the general formula (I), a compound represented by the formula (I) can be prepared by the following process:

(The first step)

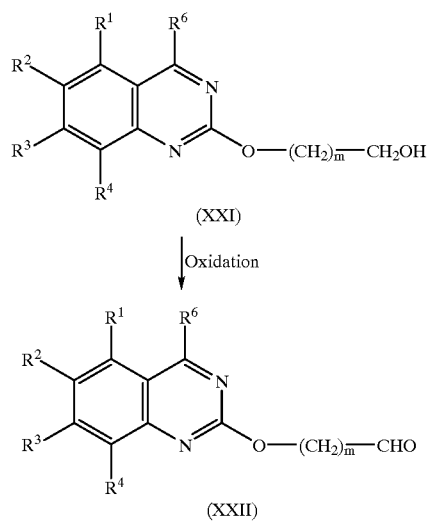

(in a series of formulas, $R^1$, $R^2$, $R^3$, $R^4$ and $R^6$ are each as defined above; and m represented 0 or an integer of 1 to 2).

That is, this process is one for preparing a compound represented by the general formula (XXII) by oxidizing a compound represented by the general formula (XXI) by conventional means.

As the oxidizing agent, everyone can be used so far as it is conventionally used and examples thereof include chromium (VI), dimethyl sulfoxide and oxalyl chloride.

As the reaction solvent, every solvent which is inert to the reaction can be used.

The reaction temperature ranges from 0° C. to the refluxing temperature of the solvent.

(The second step)

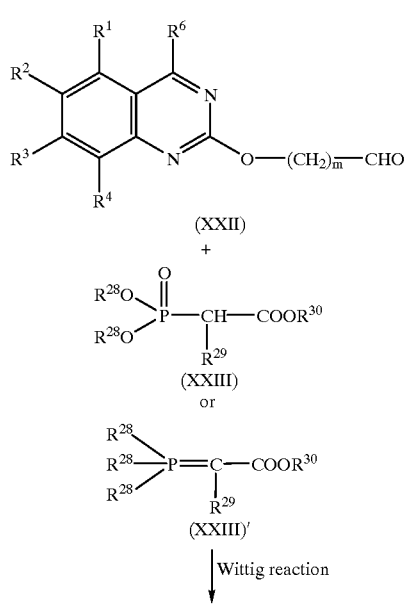

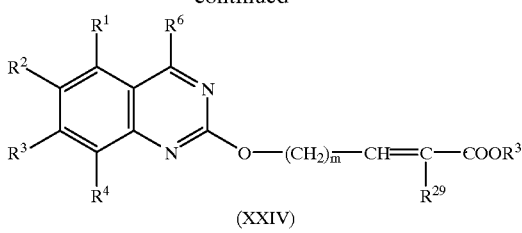

(XXIV)

(in a series of formulas, $R^1$, $R^2$, $R^3$, $R^4$, $R^6$ and m are each as defined above; and $R^{28}$, $R^{29}$ and $R^{30}$, each of which may be the same or different from one another, represent each a hydrogen atom or a lower alkyl group).

That is, this process is one for preparing a compound represented by the general formula (XXIV) by reacting the compound (XXII) prepared in the first step with the Wittig reagents (XXIII) or (XXIII)'.

As the reaction solvent, everyone which is inert to the reaction can be used.

The reaction temperature ranges from 0° C. to the refluxing temperature of the solvent.

(The third step)

(XXIV)

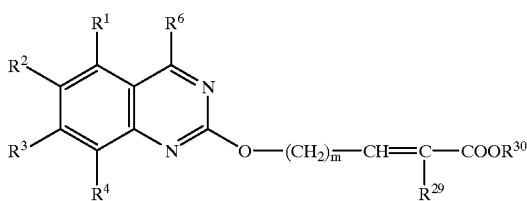

↓ reduction (XXV)

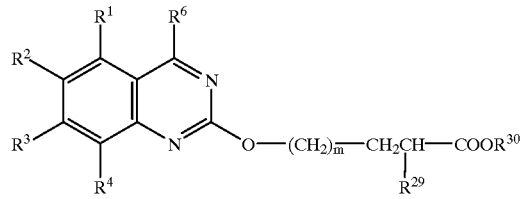

(in a series of formulas, $R^1$, $R^2$, $R^3$, $R^4$, $R^6$, $R^{29}$, $R^{30}$ and m are each as defined above).

That is, this process is one for preparing the objective compound (XXV) by reducing the compound (XXIV) prepared in the second step.

The reduction may be conducted by conventional means, and examples thereof include catalytic reduction using palladium/carbon or platinum catalyst.

Preparation Process 10

When $R^6$ is a group represented by the formula

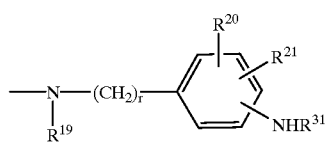

(wherein $R^{19}$, $R^{20}$, $R^{21}$ and r are each as defined above; and $R^{31}$ represents an acyl group, a lower alkylsulfonyl group or a lower alkyloxycarbonyl group) in the general formula (I), a compound represented by the general formula (I) can also be prepared by the following process:

(XX)

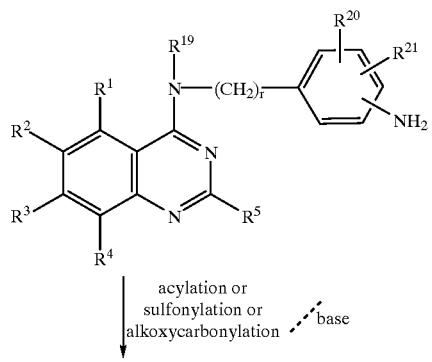

↓ acylation or sulfonylation or alkoxycarbonylation / base (XXVI)

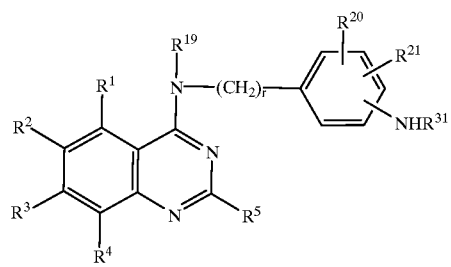

(in a series of formulas, $R^1$, $R^2$, $R^3$, $R^4$, $R^5$ $R^{19}$, $R^{20}$, $R^{21}$ and $R^{31}$, and r are each as defined above).

That is, this process is one for preparing an objective compound (XXVI) by subjecting the compound represented by the general formula (XX) prepared in the Preparative process 8 to the conventional acylation, sulfonylation or alkoxycarbonylation in the presence of a base.

As the acylating agent, every acylating agent which is conventionally used, for example, activated derivatives of carboxylic acids such as acid chloride, acid anhydride and mixed acid anhydride; and condensing agents such as dicyclohexylcarbodiimide is used.

As the sulfonylating agent, every sulfonylating agent which is conventionally used can be used and examples thereof include a lower alkylsulfonyl chloride and a lower alkylsulfonic anhydride.

The alkoxycarbonylating agent includes every alkoxycarbonylating agent which is conventionally used, for example, a lower alkyloxycarbonyl chloride and a lower alkyl pyrocarbonate.

At the base, every base can be used and examples thereof include organic bases such as pyridine and triethylamine; and inorganic bases such as sodium carbonate, potassium carbonate, sodium hydroxide and sodium hydride.

Preparation Process 11

When the ring A is selected from any of a benzene ring, a pyridine ring and a cyclohexane ring, the ring B is selected from among a pyridine ring, a pyrimidine ring and an imidazole ring, $R^5$ represents a group selected from among those defined above with respect to $R^5$ except groups which are directly bonded to the ring portion through a carbon atom; and $R^6$ represents a group selected from among those defined above with respect to $R^5$ except groups which are directly bonded to the ring portion through a carbon atom in the general formula (I), the compound represented by the general formula (I) can also be prepared by the following process. The case in which the ring portion forms a quinazoline skeleton is shown below as the representative of the above:

(The first step)

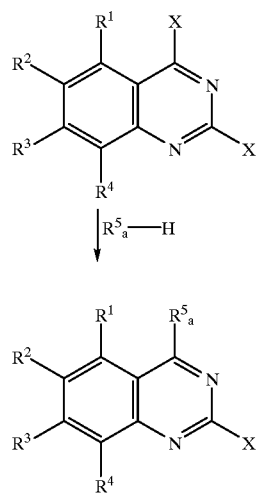

(XXVII)

(XXVIII)

(in a series of formulas, $R^1$, $R^2$, $R^3$ and $R^4$ are each as defined above; $R^5_a$ represents a group selected from among those defined above with respect to $R^5$ except groups which are directly bonded to the ring portion through a carbon atom; and X represents a halogen atom).

That is, the first step is a condensation reaction according to a conventional process.

Alcohol solvents such as isopropyl alcohol, ether solvents such as tetrahydrofuran and dimethylformamide are preferably used as the reaction solvent. However, every solvent which is inert to the reaction can be used.

In the case where $R^5_a$ is bonded to the ring portion through a nitrogen atom, it is preferred that the reaction is proceeded by heating under reflux in the presence of a tertiary amine such as triethylamine while removing HCl generated. While in the case where $R^5_a$ is bonded to the ring portion through an oxygen atom or a sulfur atom, it is preferred that the reaction is proceeded by heating under reflux in the presence of an alkali such as sodium hydroxide and sodium carbonate.

(The second step)

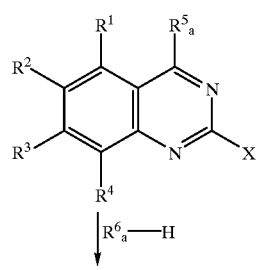

(XXVIII)

(XXIX)

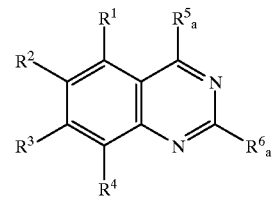

(in a series of formulas, $R^1$, $R^2$, $R^3$, $R^4$, $R^5_a$ and X are each as defined above: $R^6_a$ represents a group selected from among those defined above with respect to $R^6$ except groups which are directly bonded to the ring portion through a carbon atom).

The second step is a reaction wherein the compound (XXVIII) obtained in the first step is condensed with a compound represented by the formula $R^6_a$-H according to a conventional process.

Alcohol solvents such as isopropyl alcohol, ether solvents such as tetrahydrofuran and dimethylformamide are preferably used as the reaction solvent. However, every solvent which is inert to the reaction can be used.

In the case where $R^6_a$ is bonded to the ring portion through a nitrogen atom, it is preferred that the reaction is proceeded by heating under reflux in the presence of an organic base such as triethylamine, pyridine and ethyldiisopropylamine, an inorganic base such as sodium carbonate, potassium carbonate, sodium hydrogencarbonate, sodium hydride and sodium hydroxide or an alkoxide such as sodium methoxide and potassium t-butoxide. While in the case where $R^6_a$ is bonded to the ring portion through an oxygen atom or a sulfur atom, it is preferred that the reaction is proceeded by heating under reflux in the presence of an alkali such as sodium hydroxide and sodium carbonate.

Preparation Process 12

When the compound represented by the general formula (1) is a compound represented by the following general formula (XXXII):

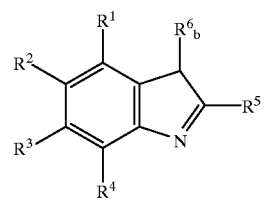

the compound can also be prepared by the following process.

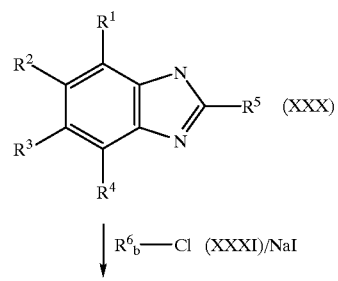

(XXX)

-continued

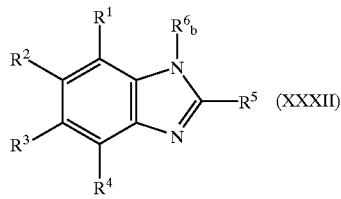

(in a series of formulas $R^1$, $R^2$, $R^3$, $R^4$, and $R^5$ are each as defined above; and $R^6_b$ represents a group selected from among groups which are directly bonded to the ring portion through a carbon atom in those defined above with respect to $R^6$).

That is, this process is one for preparing an objective compound by reacting, for example, piperonyl chloride (XXXI) with a benzimidazole derivative represented by the general formula (XXX) in the presence of an alkali by a conventional process.

Sodium iodide is preferred as alkali.

Although every solvent which is inert to the reaction can be used as the reaction solvent, polar solvents such as dimethylforamide can be cited as preferable ones.

The reaction temperature is preferably about 60 to 100° C., particularly preferably about 70 to 80° C.

Preparation Process 13

The compound of the present invention can also be prepared by the following process:

(The first step)

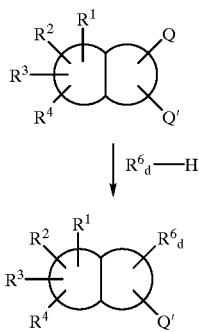

(in a series of formulas, $R^1$, $R^2$, $R^3$ and $R^4$ are each as defined above; $R^6_d$ represents a group selected from among those defined above with respect to $R^6$ except groups which are directly bonded to the ring portion through a carbon atom; and Q and Q' represent halogen atoms).

The first step is a condensation reaction according to a conventional process.

In the case where $R^6_d$ is bonded to the ring portion through a nitrogen atom, it is preferred that the reaction is proceeded by heating under reflux in the presence of an organic base such as triethylamine, pyridine and diisopropylethylamine, an inorganic base such as sodium carbonate, potassium carbonate, sodium hydrogencarbonate, sodium hydroxide and sodium hydride or an alkoxide such as sodium methoxide and potassium t-butoxide. While in the case where $R^6_d$ is bonded to the ring portion through an oxygen atom or a sulfur atom, it is preferred that the reaction is proceeded by heating under reflux in the presence of an inorganic base such as sodium hydroxide and sodium carbonate.

Every solvent which is inert to the reaction can be used as the reaction solvent, and examples thereof include alcohol solvents such as ethanol and isopropyl alcohol, ether solvents such as tetrahydrofuran, dimethylformamide and dimethylsulfoxide. Further, in the present process, the reaction can be proceeded in the absence of a reaction solvent in some cases.

(The second step)

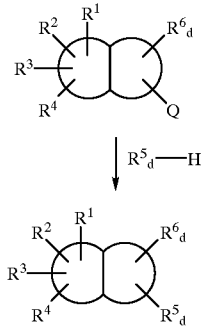

(in a series of formulas, $R^1$, $R^2$, $R^3$, $R^4$, $R^6_d$ and Q are each as defined above; and $R^5_d$ represents a group selected from among those defined above with respect to $R^5$ except groups which are directly bonded to the ring portion through a carbon atom).

That is, the second step is a process for preparing an objective compound in which the compound obtained in the first step is condensed with a compound represented by the general formula $R^5_d$-H.

In the present process, the reaction can be processed in the presence of a base at need.

As the base, organic bases such as triethylamine, pyridine and diisopropylethylamine, inorganic bases such as sodium carbonate, potassium carbonate, sodium hydrogencarbonate, sodium hydroxide and sodium hydride and alkoxides such as sodium methoxide and potassium t-butoxide can be cited.

Every solvent which inert to the reaction can be used as the reaction solvent, and examples thereof include alcohol solvents such as ethanol and isopropanol, ether solvents such as tetrahydrofuran, dimethylformamide and dimethylsulfoxide.

The reaction temperature is preferably 0° C. to 300° C.

In the case where $R^5_d$ is a group which is bonded to the ring portion through a nitrogen atom, it is preferred that the reaction is proceeded by heating under reflux in the presence of a tertiary amine such as triethylamine. While in the case where $R^5_d$ is a group which is bonded to the ring portion through a oxygen atom or a sulfur atom, it is preferred that the reaction is proceeded by heating under reflux in the presence of an alkali such as sodium hydroxide and sodium carbonate.

The compounds thus obtained in the preparation processes 1 to 13 described above can form salts thereof by a conventional process, for example, by adding sodium hydroxide, potassium hydroxide or methanesulfonic chloride.

Next, the preparation processes for the raw compounds used in the preparation processes will be shown.

Preparation Process A

Among the starting materials used in the preparation process 13, the compound in which the ring portion is a quinazoline ring and Q and Q' are chlorine atoms can also be prepared by the following process:

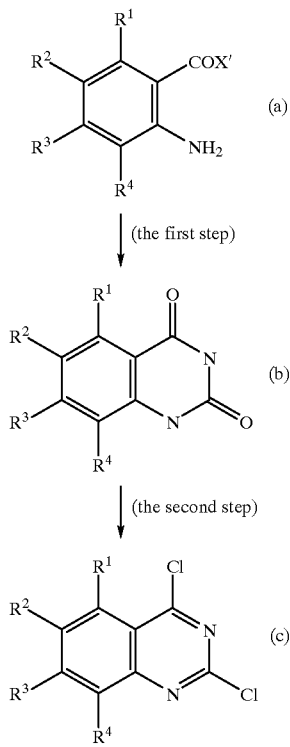

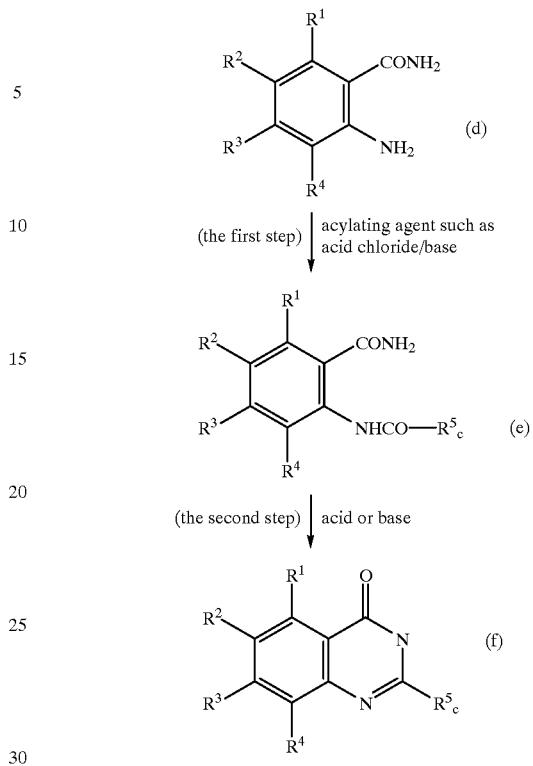

(in a series of formulas, $R^1$, $R^2$, $R^3$ and $R^4$ are each as defined above; and X' represents any group among a hydroxyl group, an alkoxy group and an amino group).

That is, this process is one for preparing the objective compound (c) by cyclizing the compound (a) by a conventional process to obtain the compound (b) and then chlorinating it by a conventional process.

The first step is a cyclization reaction. It is a step in which urea is reacted with the compound (a) to obtain the compound (b). In this case, the reaction temperature is preferably about 170 to 190° C., and although every solvent can be used as long as it is inert to the reaction, preferable examples thereof include N-methylpyrrolidone and the like. In this step, the reaction can also be proceeded in the absence of the solvent.

Further, the compound (b) can also be obtained by cyclizing with carbonyldiimidazole or by cyclizing under an acidic or basic condition after converting to urethane with a chloroformic ester when X' is an amino group.

The second step is a chlorination reaction. This step can be carried out by a conventional manner, and examples thereof include a process in which the compound (b) is heated under reflux with phosphorus pentachloride and phosphorus oxychloride, or phosphorus oxychloride while stirring to chlorinate.

Preparation Process B

The starting material (II) used in the preparation process 1 can be prepared by the following process:

(in a series of formulas, $R^1$, $R^2$, $R^3$ and $R^4$ are each as defined above; and $R^5_c$ represents a halogen atom or a group selected from among groups which are directly bonded to the ring portion through a carbon atom in those defined with respect to above $R^5$).

That is, the above process is a reaction in which an amide product is obtained by a conventional process in the first step and a cyclization is carried out in the presence of an acid or a base in the second step.

The amide produce (e) can be obtained by a conventional process, and it can be obtained, for example, by reacting the compound (d) with an acylating agent such as an acid chloride represented by $R^5_c$-COCl in the presence of a base.

Tertiary amines such as triethylamine and organic bases such as pyridine are preferably cited as the base.

Specific examples of the acylating agent include acid chlorides such as benzoyl chloride, acetyl chloride, ethyloxalyl chloride and benzyloxyacetyl chloride.

The reaction temperature is preferably about 0° C. to 30° C.

In the second step, the compound (e) obtained in the first step is heated under reflux in the presence of an acid or a base to obtain the compound (f).

The acid includes acetic anhydride and the like.
The base includes sodium hydroxide and the like.

Preparation Process C

The starting material (II) can also be prepared by the following process when $R^5_a$ is a hydrogen atom in the preparation process 1:

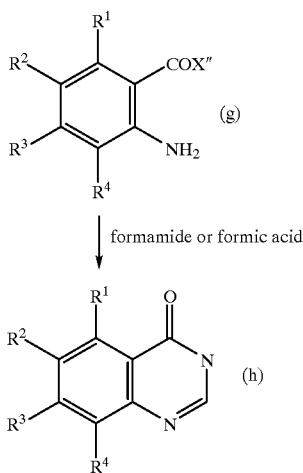

(in a series of formulas, $R^1$, $R^2$, $R^3$ and $R^4$ are each as defined above; and X" represents a hydroxyl group or a lower alkoxy group).

That is, the above process is a cyclization reaction by a conventional process.

The objective compound (h) can be synthesized, for example, by condensing the raw compound (g) with formamide by heating under reflux, or by heating it together with formic acid.

Examples of the present invention will now be described, though it is needless to say that the present invention is not limited to them. In advance of Examples, preparative examples of the raw compound for compounds according to the present invention will be described. In the Examples, Me represents a methyl group, Et an ethyl group, Bzl a benzyl group and Ac an acetyl group.

PREPARATIVE EXAMPLE 1

2-Ethoxycarbonyl-6-chloroquinazolin-4(3H)-one

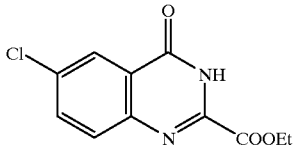

2.50 g (0.0147 mol) of 2-amino-5-chlorobenzamide was dissolved in 15 ml of pyridine. 2.0 ml of ethyloxalyl chloride was dropped into the obtained solution under stirring at room temperature. The obtained mixture was stirred for several hours and distilled under a reduced pressure to remove the solvent. The obtained residue was used as such in the subsequent reaction.

The residue was dissolved in 50 ml of acetic acid, followed by the addition of 5 ml of acetic anhydride. The obtained mixture was heated under reflux for 24 hours. The solvent was distilled away under a reduced pressure and ethanol was added to the obtained crystalline residue. The obtained mixture was filtered to recover the crystal. The crystal was washed with ethanol and ether and air-dried to give 2.78 g of the title compound as a pale-yellow crystal.

yield(%); 75; m.p.(° C.); 239~240; Mass; 253 (M +H)$^+$; NMR δ (DMSO-d$_6$); 1.36 (3H, t, J=7.2 Hz), 4.39 (2H, q, J=7.2 Hz), 7.86 (1H, d, J=8.8 Hz), 7.92 (1H, dd, J=8.8 Hz, 2.4 Hz), 8.11(1H,d,J=2.4 Hz), 12.85(1H,brs).

EXAMPLE 1

4-Chloro-6-cyanoquinazoline

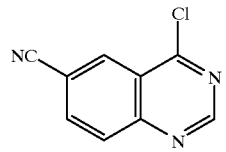

A mixture comprising 2 g of 4-hydroxy-6-carbamoylquinazoline, 30 ml of thionyl chloride and 60 ml of phosphorus oxychloride was heated under reflux for 20 hours. The reaction mixture was concentrated under a reduced pressure and the obtained residue was dissolved in 100 ml of ethyl acetate. The obtained solution was washed with water (150 ml), dried over magnesium sulfate and concentrated under a reduced pressure. The obtained residue was introduced into a silica gel column, followed by eluting with ethyl acetate and acetone to give 800 mg of the title compound.

molecular formula C$_3$H$_4$N$_3$Cl(189.5); yield(%); 40; m.p.(° C.);>290; Mass; 190(M+1)$^+$; NMR δ (DMSO-d$_6$); 7.79(1H,d, J=8.8 Hz), 8.16 (1H, dd, J=8.8 Hz, 2.0 Hz), 8.26 (1H, s), 8.49 (1H, d, J=2.0 Hz).

EXAMPLE 2

2,4-Dichloro-6-cyanoquinazoline

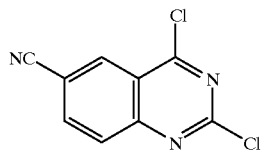

12 g of 2,4-dihydroxy-6-carbamoylquinazoline and 48.8 g of phosphorus pentachloride were suspended in a mixture comprising 200 ml of phosphorus oxychloride and 70 ml of thionyl chloride and the obtained suspension was heated under reflux for 24 hours. The reaction mixture was concentrated under a reduced pressure and the obtained crystalline residue was washed with 100 ml of ethyl acetate and 100 ml of n-hexane to give 6.8 g of the title compound.

molecular formula; C$_3$H$_3$Cl$_2$N$_3$; yield(%); 52; m.p.(° C.); 161~163; Mass; 224 (M +1)$^+$; NMR δ (CDCl$_3$); 7.94 (1H, d, J=8.0 Hz), 8.00 (1H, dd, J=8.0 Hz, 2.0 Hz), 8.49 ((1H, d,J=2.0 Hz).

EXAMPLE 3

2-Ethoxycarbonyl-4.6-dichloroquinazoline

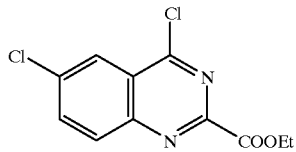

2.68 g (0.0106 mol) of 2-ethoxycarbonyl-6-chloroquinazolin-4(3H)-one obtained in Preparative Example 1 was suspended in 40 ml of phosphorus oxychloride. The suspension was heated under reflux for one hour and distilled under a reduced pressure to remove the solvent. The residue was dissolved in ethyl acetate and the obtained solution was washed with a saturated aqueous solution of sodium hydrogencarbonate. The organic layer was recovered, dried over anhydrous magnesium sulfate and filtered. The filtrate was distilled under a reduced pressure to remove the solvent, giving 2.82 g of the title compound as a pale-yellow crystal.

yield(%); 98; m.p.(° C.); 129~130; Mass; 271 (M+1M)$^+$; NMR δ (CDCl$_3$); 1.50 (3H, t, J=7.2 Hz), 4.60 (2H, q, J=7.2 Hz), 7.99 (1H, dd, J=8.8 Hz, 2.4 Hz), 8.25 (1H, d, J=8.8 Hz), 8.34(1H, d, J=2.4 Hz).

EXAMPLE 4

4-(3,4-Methylenedioxybenzyl)amino-6,7,8-trimethoxyquinazoline

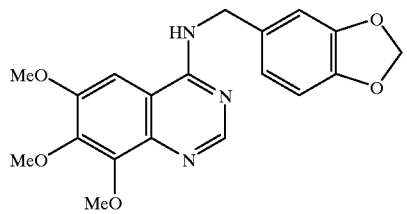

21.2 g (0.083 mol) of 4-chloro-6,7,8-trimethoxyquinazoline, 17.0 g (0.112 mol) of piperonylamine and 13.5 g (0.127 mol) of sodium carbonate were mixed with 400 ml of isopropyl alcohol. The obtained mixture was heated under reflux for 24 hours and distilled under a reduced pressure to remove the solvent. The residue was purified by silica gel column chromatography (ethyl acetate) and recrystallized from ethyl acetate to give 21.3 g of the title compound as a pale-yellow needle.

molecular formula; C$_{19}$H$_{19}$N$_3$O$_5$; yield(%); 69; m.p.(° C.); 197~198; Mass; 370 (M+H)$^+$; NMR δ (CDCl$_3$); 3.94 (3H, s), 4.03 (3H, s), 4.12 (3H, s), 4.76 (2H, d, J=8.0 Hz), 5.55 (1H, brs), 5.97 (2H, s), 6.64 (1H, s), 6.80 (1H, d, J=8.0 Hz), 6.87 (1H, d, J=8.0 Hz), 6.91 (1H, s), 8.66 (1H, s).

EXAMPLES 5 TO 48

The following compounds were prepared in a similar manner to that of Example 4.

EXAMPLE 5

4-(3.4-Methylenedioxyphenyl)amino-6,7,8-trimethoxyquinazoline

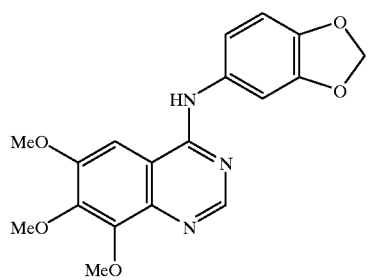

molecular formula; C$_{18}$H$_{17}$N$_3$O$_5$; yield(%); 58; m.p.(° C.); 254~255 (dec.); Mass; 356 (M+H)$^+$; NMR δ (CDCl$_3$); 4.02 (3H, s), 4.05 (3H, s), 4.13 (3H, s), 5.99 (2H, s), 6.83 (1H, d, J=7.6 Hz), 7.02 (1H, d, J=7.6 Hz), 7.32 (1H, s), 7.33 (1H, s), 8.49 (1H, brs), 8.63 (1H, s).

EXAMPLE 6

4-Benzylamino-6,7,8-trimethoxyquinazoline

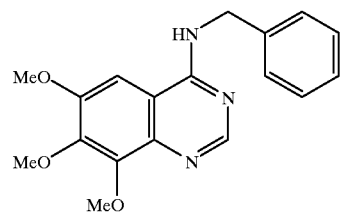

molecular formula; C$_{18}$H$_{19}$N$_3$O$_3$; yield(%); 91; m.p.(° C.); 180~181; Mass; 326 (M+H)$^+$; NMR δ (CDCl$_3$); 3.94 (3H, s), 4.03 (3H, s), 4.13 (3H, s), 4.87 (2H, d, J=5.2 Hz), 5.62 (1H, brs), 6.65 (1H, s), 7.4 (5H, m), 8.67 (1H, s).

EXAMPLE 7

4-(4-Methoxybenzyl)amino-6,7,8-trimethoxyquinazoline

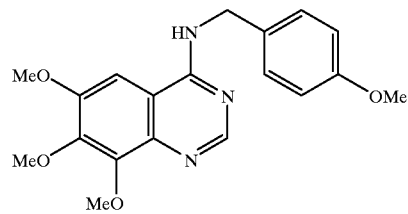

molecular formula; C$_{19}$H$_{21}$N$_3$O$_4$; yield(%); 97; m.p.(° C.); 174~175; Mass; 356 (M+H)$^+$; NMR δ (CDCl$_3$); 3.82 (3H, s), 3.93 (3H, s), 4.03 (3H, s), 4.13 (3H, s), 4.79 (2H, d, J=4.8 Hz), 5.53 (1H, brs), 6.63 (1H, s), 6.92 (2H, d, J=8.4 Hz), 7.35 (2H, d, J=8.4 Hz), 8.67 (1H, s).

EXAMPLE 8

4-(3-Methoxybenzyl)amino-6,7,8-trimethoxyquinazoline

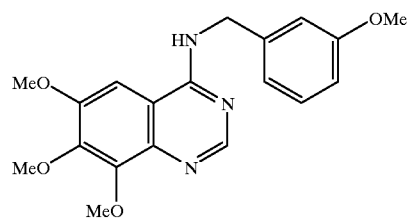

molecular formula; C$_{19}$H$_{21}$N$_3$O$_4$; yield(%); 89; m.p.(° C.); 142~143; Mass; 356 (M+H)$^+$; NMR δ (CDCl$_3$); 3.80 (3H, s), 3.96 (3H, s), 4.03 (3H, s), 4.12 (3H, s), 4.85 (2H, d, J=4.8 Hz), 5.96 (1H, brs), 6.76 (1H, s), 6.86 (1H, d, J=8.0 Hz), 6.99 (1H, d, J=8.0 Hz), 7.02 (1H, s), 7.29 (1H, t J=8.0 Hz), 8.65 (1H,s).

EXAMPLE 9

4-(4-Nitrobenzyl)amino-6,7,8-trimethoxyquinazoline

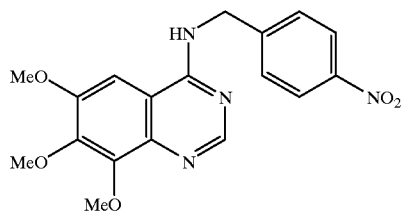

molecular formula; $C_{18}H_{18}N_4O_5$; yield(%); 28; m.p.(° C.); 210~212; Mass; 371 (M+H)$^+$; NMR δ (CDCl$_3$); 3.97 (3H, s), 4.05 (3H, s), 4.13 (3H, s), 5.01 (2H, d, J=5.6 Hz), 5.96 (1H, brs), 6.76 (1H, s), 7.54 (2H, d, J=8.8 Hz), 8.17 (2H, d, J=8.8 Hz), 8.62 (1H, s).

EXAMPLE 10

4-(3-Nitrobenzyl)amino-6,7,8-trimethoxyquinazoline

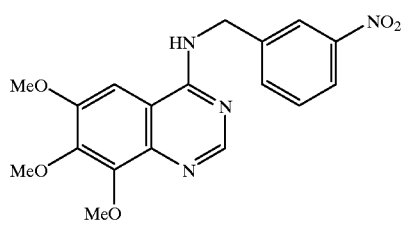

molecular formula; $C_{18}H_{18}N_4O_5$; yield(%); 30; m.p.(° C.); 159~160; Mass; 371 (M+H)$^+$; NMR δ (CDCl$_3$); 3.97 (3H, s), 4.04 (3H, s), 4.12 (3H, s), 4.99 (2H, d, J=5.6 Hz), 6.06 (1H, brs), 6.79 (1H, s), 7.51 (1H, t, J=8.0 Hz), 7.76 (1H, d, J=8.0 Hz), 8.12 (1H, d, J=8.0 Hz), 8.22 (1H, s), 8.63 (1H,s).

EXAMPLE 11

4-(4-Chlorobenzyl)amino-6,7,8-trimethoxyquinazoline

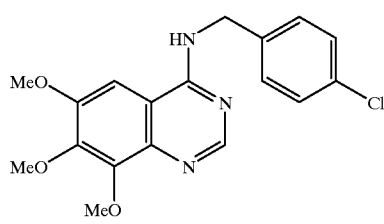

molecular formula; $C_{18}H_{18}N_3O_3Cl$; yield(%); 61; m.p.(° C.); 181~182; Mass; 360 (M+H)$^+$; NMR δ (CDCl$_3$); 3.94 (3H, s), 4.03 (3H, s), 4.12 (3H, s), 4.85 (2H, d, J=5.6 Hz), 5.76 (1H, brs), 6.70 (1H, s), 7.32 (4H, brs), 8.64 (1H, s).

EXAMPLE 12

4-(3-Chlorobenzyl)amino-6,7,8-trimethoxyquinazoline

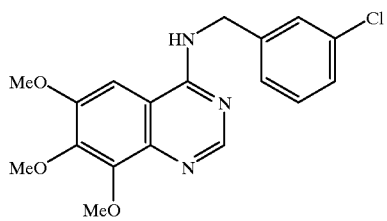

molecular formula; $C_{18}H_{18}N_3O_3Cl$; yield(%); 85; m.p.(° C.); 161~162; Mass; 360 (M+H)$^+$; NMR δ (CDCl$_3$); 3.97 (3H, s), 4.04 (3H, s), 4.13 (3H, s), 4.87 (2H, d, J=5.2 Hz), 5.66 (1H, brs), 6.68 (1H, s), 7.29 (3H, s), 7.39 (1H, s), 8.65 (1H, s).

EXAMPLE 13

4-Furfurylamino-6,7,8-trimethoxyquinazoline

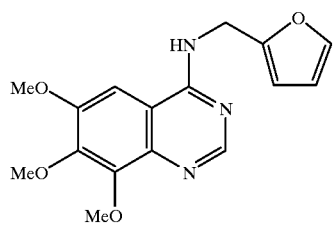

molecular formula; $C_{16}H_{17}N_3O_4$; yield(%); 81; m.p.(° C.); 198~199; Mass; 316 (M+H)$^+$; NMR δ (CDCl$_3$); 3.97 (3H, s), 4.03 (3H, s), 4.12 (3H, s), 4.87 (2H, d, J=5.2 Hz), 5.67 (1H, brs), 6.37 (2H,. m), 6.68 (1H, s), 7.42 (1H, s), 8.67 (1H, s).

EXAMPLE 14

4-(4-Picolyl)amino-6,7,8-trimethoxyquinazoline

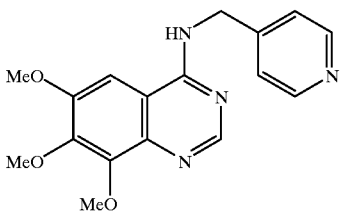

molecular formula; $C_{17}H_{18}N_4O_3$; yield(%); 76; m.p.(° C.); 166~168; Mass; 327 (M+H)$^+$; NMR δ (CDCl$_3$); 3.97 (3H, s), 4.05 (3H, s), 4.12 (3H, s), 4.92 (2H, d, J=6.0 Hz), 6.06 (1H, brs), 6.80 (1H, s), 7.28 (2H, d, J=6.0 Hz), 8.55 (2H, d, J=6.0 Hz), 8.62 (1H, s).

EXAMPLE 15

4-(4-Ethylbenzyl)amino-6,7,8-trimethoxyquinazoline

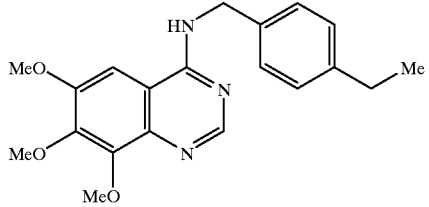

molecular formula; $C_{20}H_{23}N_3O_3$; yield(%); 88; m.p.(° C.); 195~196; Mass; 354 (M+H)$^+$; NMR δ (CDCl$_3$); 1.25 (3H, t, J=7.6 Hz), 2.67 (2H, q, J=7.6 Hz), 3.94 (3H, s), 4.03 (3H, s), 4.13 (3H, s), 4.83 (2H, d, J=4.8 Hz), 5.56 (1H, brs), 6.63 (1H,s), 7.23 (2H, d, J=8.0 Hz), 7.35 (2H, d, J=8.0 Hz), 8.67 (1H, s).

EXAMPLE 16

4-(Indan-5-ylmethyl)amino-6,7,8-trimethoxyquinazoline

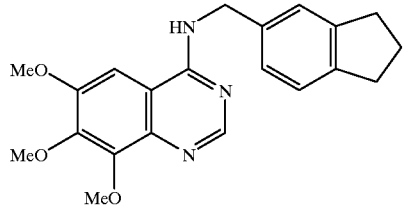

molecular formula; $C_{21}H_{23}N_3O_3$; yield(%); 61; m.p.(° C.); 198~199; Mass; 366 (M+HM)$^+$; NMR δ (CDCl$_3$); 2.11 (2H, quintet, J=7.2 Hz), 2.93 (4H, t, J=7.2 Hz), 3.94 (3H, s), 4.04 (3H, s), 4.14 (3H, s), 4.83 (2H, d, J=4.4 Hz), 5.55 (1H, brs), 6.64 (1H, s), 7.2~7.3 (3H, m), 8.68 (1H, s).

EXAMPLE 17

4-(4-Carboxybenzyl)amino-6,7,8-trimethoxyquinazoline

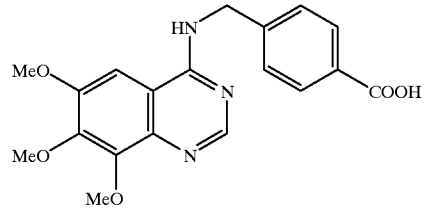

molecular formula; $C_{19}H_{19}N_3O_5$; yield(%); 86; m.p.(° C.); 227~228 (dec.); Mass; 370 (M+H)$^+$; NMR δ (CDCl$_3$); 3.89 (3H, s), 3.92 (3H, s), 3.98 (3H, s), 4.86 (2H, d, J=5.6 Hz), 7.46 (2H, d, J=8.0 Hz), 7.54 (1H, s), 7.90 (2H, d, J=8.0 Hz), 8.35 (1H, s), 8.67 (1H, brs).

EXAMPLE 18

4-(3-Hydroxymethylbenzyl)amino-6,7,8-trimethoxyquinazoline

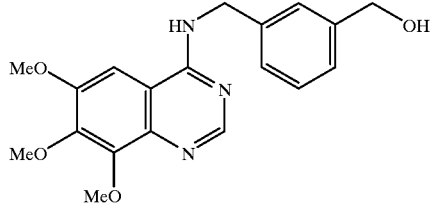

molecular formula; $C_{19}H_{21}N_3O_4$; yield(%); 86; m.p.(° C.); amorphous; Mass; 356 (M+H)$^+$; NMR δ (CDCl$_3$); 3.93 (3H, s), 4.03 (3H, s), 4.12 (3H, s), 4.70 (2H, s), 4.86 (2H, d, J=5.2 Hz), 5.82 (1H, brs), 6.72 (1H, s), 7.3~7.4 (4H, m), 8.63 (1H, s).

EXAMPLE 19

4-(3,4-Dichlorobenzyl)amino-6,7,8-trimethoxyquinazoline

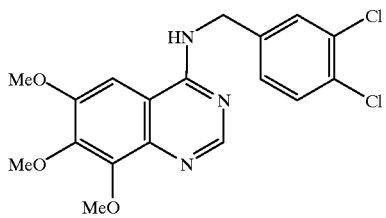

molecular formula; $C_{18}H_{17}N_3O_3Cl_2$; yield(%); 85; m.p.(° C.); 205~206; Mass; 394 (M+H)$^+$; NMR δ (CDCl$_3$); 3.97 (3H, s), 4.04 (3H, s), 4.12 (3H, s), 4.84 (2H, d, J=5.6 Hz), 5.88 (1H, brs), 6.74 (1H, s), 7.24 (1H, d, J=8.4 Hz), 7.40 (1H, d, J=8.4 Hz), 7.47 (1H, s), 8.63 (1H, s).

EXAMPLE 20

4-(3-Chloro-4-methoxybenzyl)amino-6,7,8-trimethoxyquinazoline

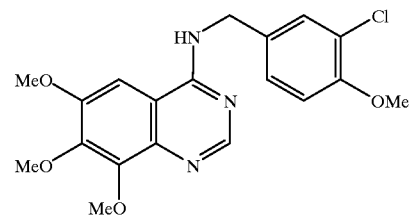

molecular formula; $C_{19}H_{20}N_3O_4Cl$; yield(%); 83; m.p.(° C.); 164~165; Mass; 390 (M+H)$^+$; NMR δ (CDCl$_3$); 3.90 (3H, s), 3.97 (3H, s), 4.04 (3H, s), 4.13 (3H, s), 4.80 (2H, d, J=5.2 Hz), 5.90 (1H, brs), 6.75 (1H, s), 6.91 (1H, d, J=8.8 Hz), 7.30 (1H, dd, J=8.8 Hz, 2.0 Hz), 7.43 (1H, d, J=2.0 Hz), 8.65 (1H, s).

EXAMPLE 21

4-(3,4-Difluorobenzyl)amino-6,7,8-trimethoxyquinazoline

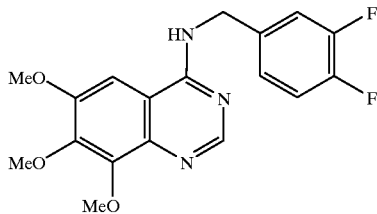

molecular formula; $C_{18}H_{17}N_3O_3F_2$; yield(%); 96; m.p.(° C.); 175~177; Mass; 362 (M+H)$^+$; NMR δ (CDCl$_3$); 3.97 (3H, s), 4.04 (3H, s), 4.13 (3H, s), 4.85 (2H, d, J=5.2 Hz), 5.73 (1H, brs), 6.69 (1H, s), 7.1~7.3 (3H, m), 8.64 (1H, s).

EXAMPLE 22

4-(3-Fluoro-4-methoxybenzyl)amino-6,7,8-trimethoxyquinazoline

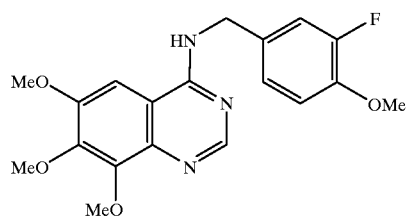

molecular formula; $C_{19}H_{20}N_3O_4F$; yield(%); 82; m.p.(° C.); 171~172; Mass; 374 (M+H)$^+$; NMR δ (CDCl$_3$); 3.89 (3H, s), 3.98 (3H, s), 4.04 (3H, s), 4.12 (3H, s), 4.81 (2H, d, J=5.6 Hz), 6.27 (1H, brs), 6.86 (1H, s), 6.94 (1H, m), 7.14~7.19 (2h, m), 8.64 (1H, s).

EXAMPLE 23

4-(3,4-Dimethoxybenzyl)amino-6,7,8-trimethoxyquinazoline

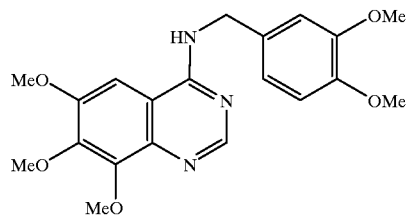

molecular formula; $C_{20}H_{23}N_3O_5$; yield(%); 32; m.p.(° C.); 171~172; Mass; 386 (M+H)$^+$; NMR δ (CDCl$_3$); 3.87 (3H, s), 3.89 (3H, s), 3.94 (3H, s), 4.03 (3H, s), 4.13 (3H, s), 4.79 (2H, d, J=5.2 Hz), 5.67 (1H, brs), 6.69 (1H, s), 6.86 (1H, d, J=8.8 Hz), 6.96 (1H, s), 6.98 (1H, d, J=8.8 Hz), 8.67 (1H, s).

EXAMPLE 24

4-(4-Hydroxy-3-methoxybenzyl)amino-6,7,8-trimethoxyquinazoline

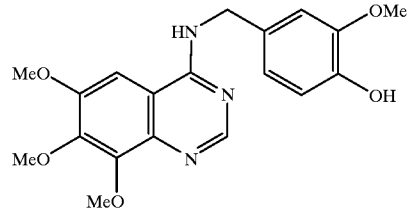

molecular formula; $C_{19}H_{21}N_3O_5$; yield(%); 16; m.p.(° C.); 201~202 (dec.); Mass; 372 (M+H)$^+$; NMR δ (CDCl$_3$); 3.88 (3H, s), 3.96 (3H, s), 4.03 (3H, s), 4.12 (3H, s), 4.78 (2H, d, J=5.2 Hz), 6.00 (1H, brs), 6.77 (1H, s), 6.91 (1H, s), 6.92 (1H, s), 6.97 (1H, s), 8.65 (1H, s).

EXAMPLE 25

4-(3,4-Ethylenedioxybenzyl)amino-6,7,8-trimethoxyquinazoline molecular formula; $C_{20}H_{21}N_3O_5$; yield(%); 92; m.p.(° C.); 217~219; Mass; 384 (M+H)$^+$; NMR δ (CDCl$_3$); 3.95 (3H, s), 4.03 (3H, s), 4.13 (3H, s), 4.26 (4H, s), 4.75 (2H, d, J=5.2 Hz), 5.54 (1H, brs), 6.64 (1H, s), 6.87 (1H, d, J=8.0 Hz), 6.90 (1H, d, J=8.0 Hz), 6.94 (1H, s), 8.66 (1H, s).

EXAMPLE 26

4-(3-Allyl-4-methoxybenzyl)amino-6,7,8-trimethoxyquinazoline

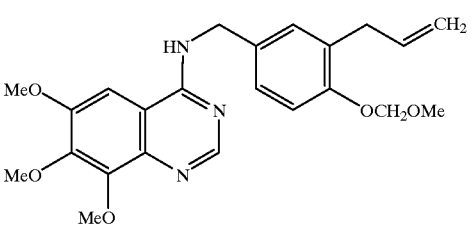

molecular formula; $C_{23}H_{27}N_3O_5$; yield(%); 49; m.p.(° C.); 120~121; Mass; 426 (M+H)$^+$; NMR δ (CDCl$_3$); 3.41 (2H, d, J=6.8 Hz), 3.48 (3H, s), 3.94 (3H, s), 4.03 (3H, s), 4.12 (3H, s), 4.77 (2H, d, J=5.2 Hz), 5.06 (2H, m), 5.21 (2H, s), 5.78 (1H, brs), 5.98 (1H, m), 6.71 (1H, s), 7.07 (1H, d, J=8.4 Hz), 7.23 (1H, s), 7.24 (1H, d, J=8.4 Hz), 8.65 (1H, s).

EXAMPLE 27

4-(Benzimidazol-5-ylmethyl)amino-6,7,8-trimethoxyquinazoline

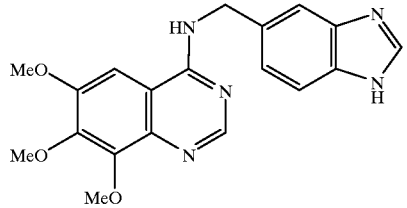

molecular formula; $C_{19}H_{19}N_5O_3$; yield(%); 52; m.p.(° C.); 235~240 (dec.); Mass; 366 (M+H)$^+$; NMR δ (DMSO-d$_6$); 3.93 (3H, s), 3.95 (3H, s), 3.98 (3H, s), 4.97 (2H, d, J=6.0 Hz), 7.30 (1H, dd, J=8.4 Hz, 1.6 Hz), 7.57 (1H, d, J=8.4 Hz), 7.63 (1H, d, J=1.6 Hz), 7.83 (1H, s), 8.31 (1H, s), 8.36 (1H, brs), 8.52 (1H, s), 9.76 (1H, brs).

EXAMPLE 28

4-(4-Benzyloxy-3-nitrobenzyl)amino-6,7,8-trimethoxyquinazoline

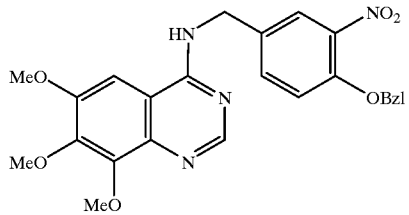

molecular formula; $C_{25}H_{24}N_4O_6$; yield(%); 81; m.p.(° C.); 181~182; Mass; 477 (M+H)$^+$; NMR δ (CDCl$_3$); 3.98 (3H, s), 4.03 (3H, s), 4.10 (3H, s), 4.85 (2H, d, J=5.2 Hz), 5.21 (2H, s), 6.54 (1H, brs), 6.93 (1H, s), 7.06 (1H, d, J=8.4 Hz), 7.30~7.45 (5H, m), 7.60 (1H, dd, J=8.4 Hz, 2.4 Hz), 7.87 (1H, d, J=2.4 Hz), 8.61 (1H, s).

EXAMPLE 29

4-(4-Chloro-3-nitrobenzyl)amino-6,7,8-trimethoxyquinazoline

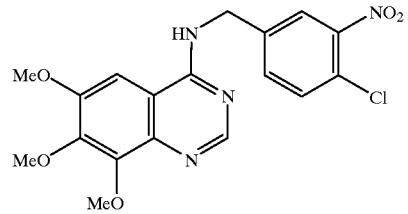

molecular formula; $C_{18}H_{17}N_4O_5Cl$; yield(%); 88; m.p.(° C.); 218~219 (dec.); Mass; 405 (M+H)$^+$; NMR δ (CDCl$_3$); 3.98 (3H,s), 4.04 (3H, s), 4.13 (3H, s), 4.93 (2H, d, J=6.0 Hz), 5.98 (1H, brs), 6.75 (1H, s), 7.50 (1H, d, J=8.4 Hz), 7.58 (1H, dd, J=8.4 Hz, 2.0 Hz), 7.87 (1H, d, J=2.0 Hz), 8.61 (1H, s).

EXAMPLE 30

4-(2-Propoxybenzyl)amino-6,7,8-trimethoxyquinazoline

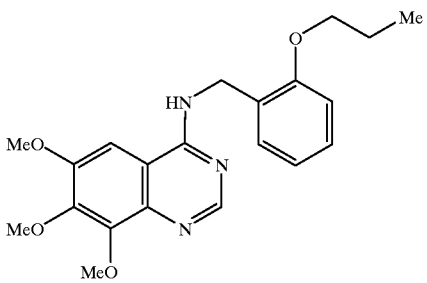

molecular formula; $C_{21}H_{25}N_3O_4$; yield(%); 80; m.p.(° C.); 139~140; Mass; 384 (M+H)$^+$; NMR δ (CDCl$_3$); 1.07 (3H, t, J=7.4 Hz), 1.85 (2H, m), 3.95 (3H, s), 4.02 (3H, s), 4.02 (2H, t, J=6.4 Hz), 4.10 (3H, s), 4.89 (2H, d, J=5.6 Hz), 6.72 (1H, s), 6.9 (2H, m), 7.28 (1H, m), 7.38 (1H, d, J=7.2 Hz), 8.64 (1H, s).

EXAMPLE 31

4-(2,4,6-Trimethoxybenzyl)amino-6,7,8-trimethoxyquinazoline

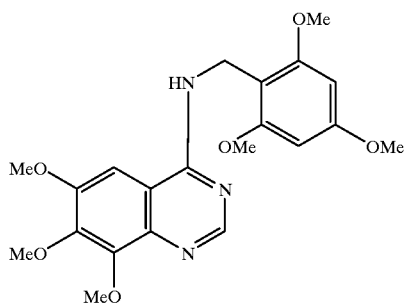

molecular formula; $C_{21}H_{25}N_3O_6$; yield(%); 64; m.p.(° C.); 213~215; Mass; 416 (M+H)$^+$; NMR δ (CDCl$_3$); 3.85 (9H, s), 3.92 (3H, s), 4.01 (3H, s), 4.11 (3H, s), 4.79 (2H, d, J=4.4 Hz), 5.65 (1H, brs), 6.20 (2H, s), 6.60 (1H, s), 8.68 (1H, s).

EXAMPLE 32

4-(3,4,5-Trimethoxybenzyl)amino-6,7,8-trimethoxyquinazoline

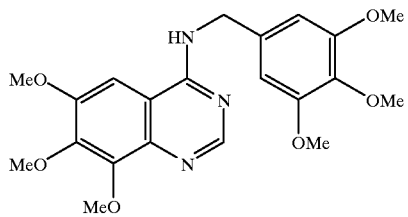

molecular formula; $C_{21}H_{25}N_{36}$; yield(%); 60; m.p.(° C.); 153~154; Mass; (M+H)$^+$ [LEFT OUT BY MISTAKE? NMR δ (CDCl$_3$); 3.85 (9H, s), 3.97 (3H, s), 4.03 (3H, s), 4.13 (3H, s), 4.80 (2H, d, J=5.6 Hz), 6.66 (2H, s), 6.80 (1H, s), 8.66 (1H, s).

EXAMPLE 33

4-(2-Chloro-4,5-methylenedioxybenzyl)amino-6,7,8-trimethoxyquinazoline

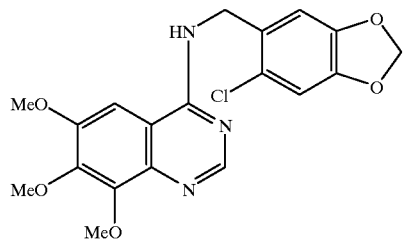

molecular formula; $C_{19}H_{18}N_3O_5Cl$; yield(%); 76; m.p.(° C.); 220~221; Mass; 404 (M+H)$^+$; NMR δ (CDCl$_3$); 3.97 (3H, s), 4.02 (3H, s), 4.11 (3H, s), 4.86 (2H, d, J=6.0 Hz), 5.95 (2H, s), 6.70 (1H, brt, J=6.0 Hz), 6.86 (1H, s), 6.95 (1H, s), 6.98 (1H, s), 8.61 (1H, s).

EXAMPLE 34

4-(4,5-Methylenedioxy-2-nitrobenzyl)amino-6,7,8-trimethoxyquinazoline molecular formula; $C_{19}H_{18}N_4O_7$; yield(%); 15; m.p.(° C.); 182~183; Mass; 415 (M+H)$^+$; NMR δ (CDCl$_3$); 3.99 (3H, s), 4.02 (3H, s), 4.10 (3H, s), 5.08 (2H, d, J=6.4 Hz), 6.09 (2H, s), 6.82 (2H, s & brs), 7.27 (1H, s), 7.57 (1H, s), 8.61 (1H, s).

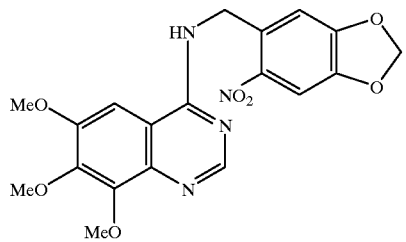

EXAMPLE 35

4-[2-(4-Nitrophenyl)ethyl]amino-6,7,8-trimethoxyquinazoline

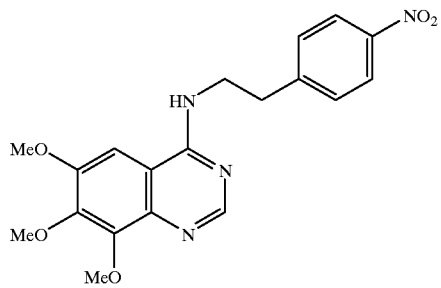

molecular formula; $C_{19}H_{20}N_4O_5$; yield(%); 58; m.p.(° C.); 152~153; Mass; 385 (M+H)$^+$; NMR δ (CDCl$_3$); 3.18 (2H, t, J=7.2 Hz), 3.92 (3H, s), 3.96 (3H, m), 4.04 (3H, s), 4.13 (3H, s), 5.57 (1H, brs), 6.58 (1H, s), 7.41 (2H, d, J=8.8 Hz), 8.17 (2H, d, J=8.8 Hz), 8.66 (1H, s).

EXAMPLE 36

4-[2-(3,4-Methylenedioxyphenyl)ethyl]amino-6,7,8-trimethoxyquinazoline

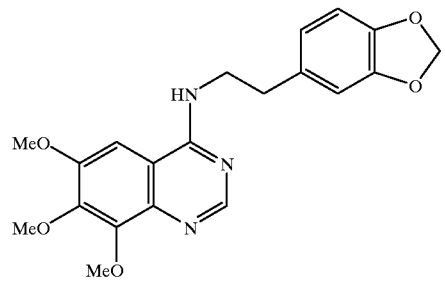

molecular formula: $C_{20}H_{21}N_3O_5$; yield(%): 68; m.p.(° C.); 193~194; Mass; 384 (M+H)$^+$; NMR δ (CDCl$_3$); 2.96 (2H, t, J=6.8 Hz), 3.87 (2H, m), 3.93 (3H, s), 4.03 (3H, s), 4.12 (3H, s), 5.43 (1H, brs), 5.95 (2H, s), 6.52 (1H, s), 6.71 (1H, d, J=8.0 Hz), 6.77 (1H, s), 6.78 (1H, d, J=8.0 Hz), 8.65 (1H, s).

EXAMPLE 37

4-[2-(Imidazol-4-yl)ethyl]amino-6,7,8-trimethoxyquinazoline

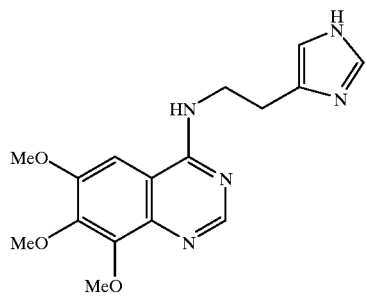

molecular formula: $C_{16}H_{19}N_5O_3$; yield(%): 77; m.p.(° C.); 164~166 (dec.); Mass; 330 (M+H)$^+$; NMR δ (DMSO-d$_6$); 3.00 (2H, t, J=7.2 Hz), 3.81 (2H, m), 3.87 (3H, s), 3.92 (3H, s), 3.97 (3H, s), 7.25 (1H, s), 7.56 (1H, s), 8.39 (1H, s), 8.45 (1H, s), 8.50 (1H, brs).

EXAMPLE 38

4-(α-Methyl-3,4-methylenedioxybenzyl)amino-6,7,8-trimethoxyquinazoline

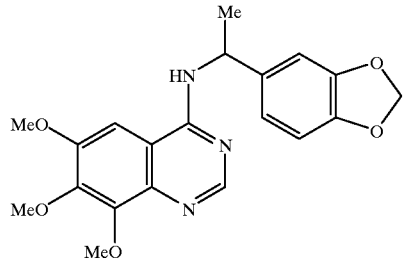

molecular formula: C$_{20}$H$_{21}$N$_3$O$_5$; yield(%): 67; m.p.(° C.); 200~201; Mass; 384 (M+H)$^+$; NMR δ (CDCl); 1.67 (2H, d, J=6.8 Hz), 3.99 (3H, s), 4.04 (3H, s), 4.13 (3H, s), 5.47 (1H, brs), 5.57 (1H, t, J=6.8 Hz), 5.97 (2H, s), 6.65 (1H, s), 6.81 (1H, d, J=7.6 Hz), 6.94 (1H, d, J=7.6 Hz), 6.95 (1H, s), 8.63 (1H, s).

EXAMPLE 39

4-[1-Methyl-1-(3,4-methylenedioxyphenyl)ethyl]amino-6,7,8-trimethoxyquinazoline

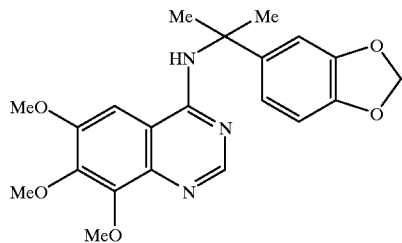

molecular formula: C$_{21}$H$_{23}$N$_3$O$_5$; yield(%): 4; m.p.(° C.); 191~192; Mass; 398 (M+H)$^+$; NMR δ (CDCl$_3$); 1.90 (6H, s), 4.03 (3H, s), 4.03 (3H, s), 4.09 (3H, s), 5.93 (2H, s), 6.74 (1H, d, J=7.6 Hz), 6.82 (1H, s), 6.92 (2H, m), 8.46 (1H,s).

EXAMPLE 40

4-[N-Ethyl-(3,4-methylenedioxybenzyl)amino]-6,7,8-trimethoxyquinazoline

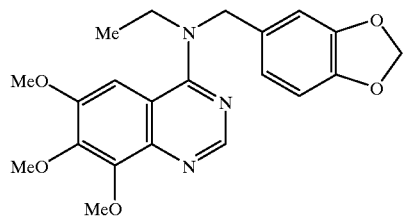

molecular formula; C$_{21}$H$_{23}$N$_3$O$_5$; yield(%); 73; m.p.(° C.); 100~101; Mass; 398 (M+H)$^+$; NMR δ (CDCl$_3$); 1.37 (3H, t, J=7.0 Hz), 3.56 (3H, s), 3.67 (2H, q, J=7.0 Hz), 4.03 (3H, s), 4.11 (3H, s), 4.79 (2H, s), 5.98 (2H, s), 6.85 (1H, d, J=7.2 Hz), 6.93 (1H, s), 6.93 (1H, d, J=7.2 Hz), 6.97 (1H, s), 8.69 (1H, s).

EXAMPLE 41

4-[N-(Ethoxycarbonylmethyl)-(3,4-methylenedioxybenzyl)amino]-6,7,8-trimethoxyquinazoline

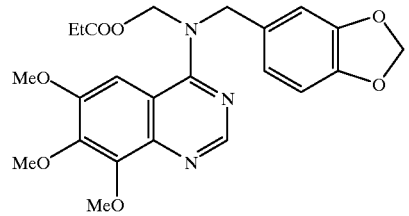

molecular formula; C$_{23}$H$_{25}$N$_3$O$_7$; yield(%); 41; m.p.(° C.); oily substance; Mass; 456 (M+H)$^+$; NMR δ (CDCl$_3$); 1.29 (3H, t, J=7.2 Hz), 3.44 (3H, s), 4.02 (3H, s), 4.10 (3H, s), 4.20 (2H, s), 4.25 (2H, q, J=7.2 Hz), 4.98 (2H, s), 6.00 (2H, s), 6.88 (1H, d, J=8.0 Hz), 6.97 (1H, s), 7.01 (1H, d, J=8.0 Hz), 8.64 (1H, s).

EXAMPLE 42

4-[N-(2-Methoxyethyl)-(3,4-methylenedioxybenzyl)amino]-6,7,8-trimethoxyquinazoline

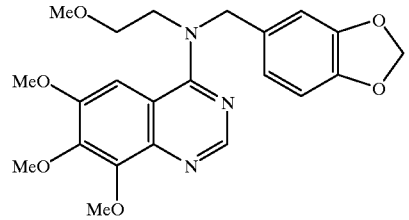

molecular formula; C$_{22}$H$_{25}$N$_3$O$_6$; yield(%); 21; m.p.(° C.); 87~88; Mass; 428 (M+H)$^+$; NMR δ (CDCl$_3$); 3.36 (3H, s), 3.58 (3H, s), 3.80~3.85 (4H, m), 4.02 (3H, s), 4.10 (3H, s), 4.92 (2H, s), 5.97 (2H, s), 6.83 (1H, d, J=7.6 Hz), 6.92 (1H, d, J=7.6 Hz), 6.94 (1H, s), 7.19 (1H, s), 8.67 (1H, s).

EXAMPLE 43

4-(6.7-Dimethoxy-1,2,3,4-tetrahydroisoquinolin-2-yl)-6,7,8-trimethoxyquinazoline

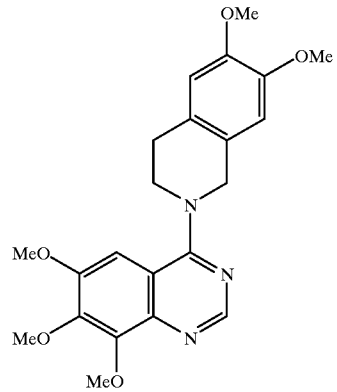

molecular formula; C$_{22}$H$_{25}$N$_3$O$_5$; yield(%); 79; m.p.(° C.); 157~158; Mass; 412 (M+H)$^+$; NMR δ (CDCl$_3$); 3.11

(2H, t, J=5.8 Hz), 3.87 (3H, s), 3.89 (3H, s), 3.96 (2H, t, J=5.8 Hz), 3.99 (3H, s), 4.07 (3H, s), 4.14 (3H, s), 4.80 (2H, s), 6.67 (1H, s), 6.71 (1H, s), 7.03 (1H, s), 8.74 (1H, s).

EXAMPLE 44

4-[4-(1Hydroxyethyl)benzyl]amino-6-methoxyquinazoline

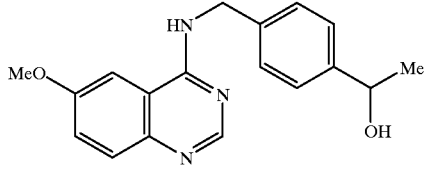

molecular formula; $C_{18}H_{19}N_3O_2$; yield(%); 46; m.p.(° C.); amorphous; Mass; 310 (M+H)$^+$; NMR δ (CDCl$_3$); 1.47 (2H, d, J=6.4 Hz), 3.91 (3H, s), 4.87 (2H, d, J=5.2 Hz), 4.84~4.94 (1H, m), 7.34~7.42 (6H, m), 7.59 (1H, brs), 7.79 (1H, d, J=8.8 Hz), 8.52 (1H, s).

EXAMPLE 45

4-(Benzimidazol-5-ylmethyl)amino-6-methoxyquinazoline

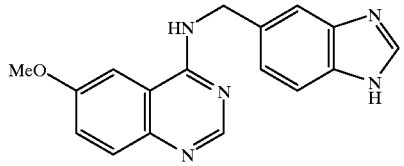

molecular formula; $C_{17}H_{15}N_5O$; yield(%); 18; m.p.(° C.); 254~255; Mass; 306 (M+H)$^+$; NMR δ (DMSO-d$_6$); 3.88 (3H, s), 4.91 (2H, d, J=6.0 Hz), 7.24 (1H, d, J=8.4 Hz), 7.40 (1H, dd, J=9.2 Hz, 2.8 Hz), 7.54 (1H, d, J=8.4 Hz), 7.56 (1H, s), 7.63 (1H, d, J=9.2 Hz), 7.73 (1H, d, J=2.8 Hz), 8.16 (1H, s), 8.37 (1H, s), 8.67 (1H, t, J=6.0 Hz), 12.33 (1H, brs).

EXAMPLE 46

4-(3,4-Methylenedioxybenzyl)amino-6-methoxyquinazoline

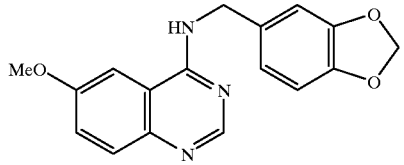

molecular formula; $C_{17}H_{15}N_3O_3$; yield(%); 86; m.p.(° C.); 207~208; Mass; 310 (M+H)$^+$; NMR δ (CDCl$_3$); 3.89 (3H, s), 4.78 (2H, d, J=5.2 Hz), 5.70 (1H, brs), 5.97 (2H, s), 6.80 (1H, d, J=7.6 Hz), 6.9 (3H, m), 7.40 (1H, d, J=9.2 Hz), 7.80 (1H, d, J=9.2 Hz), 8.63 (1H, s).

EXAMPLE 47

4-[2-(3,4-Methylenedioxyphenyl)pyrrolidino]-6-methoxyquinazoline

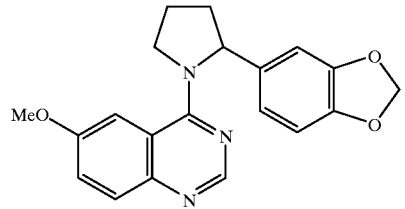

molecular formula; $C_{20}H_{19}N_3O_3$; yield(%); 85; m.p.(° C.); oily substance; Mass; 350 (M+1)$^+$; NMR δ (CDCl$_3$); 1.95~2.10 (3H, m), 2.37 (1H, m), 3.58 (3H, s), 4.05~4.20 (2H, m), 5.58 (1H, m), 5.93 (1H, s), 5.94 (1H, s), 6.78 (1H, d, J=8.4 Hz), 6.84 (1H, s), 6.85 (1H, d, J=8.4 Hz), 7.30 (1H, d, J=10.0 Hz), 7.35 (1H, s), 7.74 (1H, d, J=10.0 Hz), 8.53 (1H, s).

EXAMPLE 48

4-(4-Methoxy-3-nitrobenzyl)amino-6-methoxyquinazoline

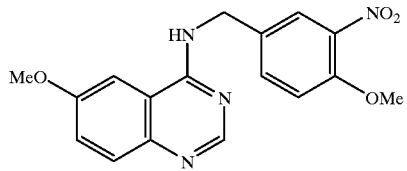

molecular formula; $C_{17}H_{16}N_4O_4$; yield(%); 22; m.p.(° C.); 205~206 (dec.); Mass; 341 (M+1)$^+$; NMR δ (CDCl$_3$); 3.93 (3H, s), 3.94 (3H, s), 4.91 (2H, d, J=6.0 Hz), 7.07 (1H, dd, J=8.4 Hz, 1.2 Hz), 7.21 (1H, d, J=1.2 Hz), 7.39 (1H, dd, J=9.2 Hz, 2.4 Hz), 7.53 (1H, d, J=2.4 Hz), 7.75 (1H, d, J=9.2 Hz), 7.82 (1H, d, J=8.4 Hz), 8.03 (1H, brs), 8.51 (1H,s).

EXAMPLE 49

4-(3,4-Methylenedioxybenzyl)amino-6-methylthioquinazoline

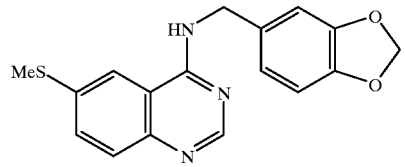

4.12 g(0.0196 mol) of 4-chloro-6-methylthioquinazoline, 3.70 g (0.0245 mol) of piperonylamine and 3.50 g (0.0330 mol) of sodium carbonate were mixed with 100 ml of isopropyl alcohol. The obtained mixture was heated under reflux for 24 hours and distilled under a reduced pressure to remove the solvent. The obtained residue was purified by silica gel column chromatography (ethyl acetate/n-hexane) and recrystallized from chloroform/n-hexane to give 5.32 g of the title compound as a pale-yellow crystal. molecular formula; $C_{17}H_{15}O_2N_3S$; yield(%); 83; m.p.(° C.); 174~175;

Mass; 326 (M+H)⁺; NMR δ (CDCl₃); 2.59 (3H, s), 4.79 (2H, d, J=5.6 Hz), 5.93 (2H, s), 6.77 (1H, d, J=8.0 Hz), 6.89 (1H, d, J=8.0 Hz), 6.94 (1H, s), 7.62 (1H, dd, J=8.8 Hz, 2.0 Hz), 7.75 (1H, d, J=8.8 Hz), 7.97 (1H, d, J=2.0 Hz), 8.10 (1H, brs), 8.56 (1H, s).

EXAMPLES 50 TO 54

The following compounds were prepared in a similar manner to that of Example 49.

EXAMPLE 50

4-(3,4-Dichlorobenzyl)amino-6-methylthioquinazoline

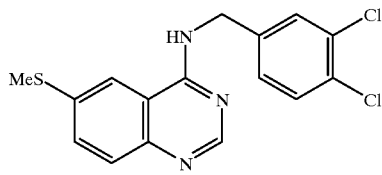

molecular formula; C₁₆H₁₃N₃SCl₂; yield(%); 85; m.p.(° C.); 184~185; Mass; 350 (M+H)⁺; NMR δ (CDCl₃); 2.61 (3H, s), 4.83 (2H, d, J=5.6 Hz), 7.28 (1H, dd, J=8.4 Hz, 2.0 Hz), 7.40 (1H, d, J=8.4 Hz), 7.51 (1H, d, J=2.0 Hz), 7.64 (1H, dd, J=8.8 Hz, 2.0 Hz), 7.76 (1H, d, J=8.8 Hz), 7.97 (1H, d, J=2.0 Hz), 8.19 (1H, brs), 8.55 (1H, s).

EXAMPLE 51

4-(3-Fluoro-4-methoxybenzyl)amino-6-methylthioquinazoline

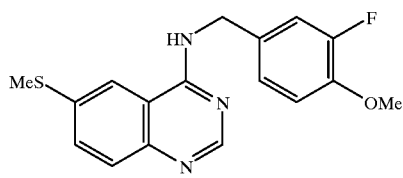

molecular formula; C₁₇H₁₆N₃OSF; yield(%); 89; m.p.(° C.); 168~169; Mass; 330 (M+H)⁺; NMR δ (CDCl₃); 2.58 (3H, s), 3.90 (3H, s), 4.82 (2H, d, J=5.6 Hz), 6.29 (1H, brs), 6.95 (1H, m), 7.13~7.18 (2H, m), 7.54 (1H, s), 7.63 (1H, d, J=8.8 Hz), 7.79 (1H, d, J=8.8 Hz), 8.64 (1H, s).

EXAMPLE 52

4-(Benzimidazol-5-ylmethyl)amino-6-methylthioquinazoline

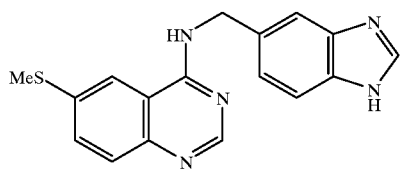

molecular formula; C₁₇H₁₅N₅S; yield(%); 48; m.p.(° C.); 271–275(dec.); Mass; 322 (M+H)⁺; NMR δ (DMSO-d₆); 2.67 (3H, s), 5.06 (2H, d, J=5.6 Hz), 7.47 (1H, d, J=8.4 Hz), 7.68 (1H, d, J=8.8 Hz), 7.77 (2H, m), 7.87 (1H, d, J=8.8 Hz), 8.40 (1H, s), 8.77 (1H, s), 8.84 (1H, s), 10.68 (1H, brs).

EXAMPLE 53

4-[N-(2-Methoxyethyl)-(3,4-methylenedioxybenzyl)amino]-6-methylthioquinazoline

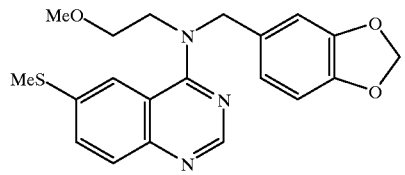

molecular formula; C₂₀H₂₁N₃O₃S; yield(%); 27; m.p.(° C.); 92~93; Mass; 384 (M+H)⁺; NMR δ (CDCl₃); 2.16 (3H, s), 3.35 (3H, s), 3.82 (2H, t, J=5.0 Hz), 3.89 (2H, t, J=5.0 Hz), 5.01 (2H, s), 5.98 (2H, s), 6.84 (1H, d, J=8.4 Hz), 6.89 (1H, d, J=8.4 Hz), 6.90 (1H, s), 7.56 (1H, dd, J=8.8 Hz, 2.0 Hz), 7.66 (1H, d, J=2.0 Hz), 7.82 (1H, d, J=8.8 Hz).

EXAMPLE 54

4-[N-(2-Hydroxyethyl)-(3,4-methylenedioxybenzyl)amino]-6-methylthioquinazoline

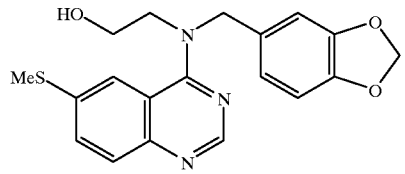

molecular formula; C₁₉H₁₉N₃O₃S; yield(%); 21; m.p.(° C.); 146~147 (dec.); Mass; 370 (M+H)⁺; NMR δ (CDCl₃); 2.00 (3H, s), 3.93 (2H, t, J=4.2 Hz), 4.01 (2H, t, J=4.2 Hz), 5.00 (2H, s), 6.01 (2H, s), 6.89 (3H, m), 7.57 (2H, m), 7.82 (1H, d, J=9.2 Hz), 8.55 (1H,s).

EXAMPLE 55

4-(4-Chloro-3-nitrobenzyl)amino-6-chloroquinazoline

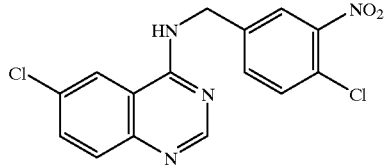

3.00 g (0.015 mol) of 4,6-dichloroquinazoline and 3.80 g (0.0170 mol) of 4-chloro-3-nitrobenzylamine hydrochloride were dissolved in a mixture comprising 100 ml of isopropyl alcohol and 15 ml of triethylamine. The obtained solution was heated under reflux for 24 hours and distilled under a reduced pressure to remove the solvent. The residue was purified by silica gel column chromatography (chloroform/ ethyl acetate) and recrystallized from chloroform/n-hexane to give 4.85 g of the title compounds as a pale-yellow crystal.

molecular formula; C₁₅H₁₀N₄O₂Cl₂; yield(%); 92; m.p.(° C.); 199~200; Mass; 349 (M+H)⁺; NMR δ (CDCl₃); 4.85

(2H, d, J=6.0 Hz), 7.49 (1H, d, J=8.4 Hz), 7.61 (1H, dd, J=8.4 Hz, 2.0 Hz), 7.66 (1H, dd, J=8.8 Hz, 2.0 Hz), 7.76 (1H, d, J=8.8 Hz), 7.96 (1H, d, J=2.0 Hz), 8.20 (1H, d, J=2.0 Hz), 8.23 (1H, brt, J=6.0 Hz), 8.58 (1H,s).

EXAMPLE 56

4-(α-Ethoxycarbonyl-3,4-methylenedioxybenzyl)amino-6-chloroquinazoline

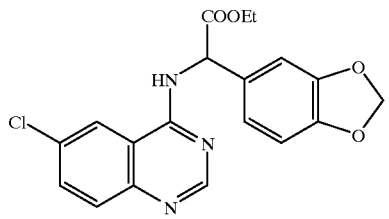

30 ml of 2-propanol, 1.07 g of triethylamine and 1.01 g of α-ethoxycarbonyl-3,4-methylenedioxybenzylamine were added to 704 mg of 4,6-dichloroquinazoline. The obtained mixture was refluxed for 4 hours, followed by the addition of water. The obtained mixture was extracted with chloroform thrice. The chloroform layers were combined, dried over magnesium sulfate and distilled under a reduced pressure to remove the solvent. The residue was recrystallized (from ethanol/ethyl acetate/hexane) to give 1.167 g of the title compound.

molecular formula; $C_{19}H_{16}N_3O_4Cl$; yield(%); 86; m.p.(° C.); 169~170; Mass; 386 (M+1); NMR δ (CDCl$_3$); 1.28 (3H, t, J=7.2 Hz), 4.27 (2H, m), 5.85 (1H, d, J=6.4 Hz), 5.98 (2H, s), 6.70 (1H, brs), 6.81 (1H, d, J=8.8 Hz), 6.99 (2H, m), 7.10 (1H, dd, J=8.8 Hz, 2.4 Hz), 7.83 (1H, d, J=2.4 Hz), 8.85 (1H, d, J=8.8 Hz), 8.63 (1H, s).

EXAMPLES 57–64

The following compounds were prepared in a similar manner to that of Example 56 or 57.

EXAMPLE 57

4-(3,4-Methylenedioxybenzyl)amino-6-chloroquinazoline

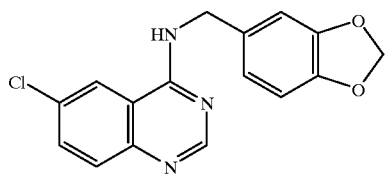

molecular formula; $C_{16}H_{12}N_3O_2Cl$; yield(%); 76; m.p.(° C.); 199~200; Mass; 314 (M+H)$^+$; NMR δ (CDCl$_3$); 4.76 (2H, d, J=5.6 Hz), 5.82 (1H, brs), 5.98 (2H, s), 6.81 (1H, d, J=8.0 Hz), 6.87 (1H, d, J=8.0 Hz), 6.89 (1H, s), 7.67 (1H, s), 7.69 (1H, d, J=8.0 Hz), 7.81 (1H, d, J=8.0 Hz), 8.70 (1H, s).

EXAMPLE 58

4-(3,4-Dichlorobenzyl)amino-6-chloroquinazoline

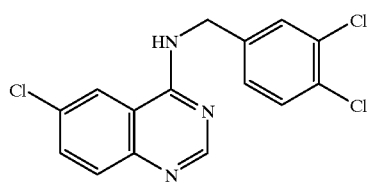

molecular formula; $C_{15}H_{10}N_3Cl_3$; yield(%); 72; m.p.(° C.); 215~216; Mass; 338 (M+H)$^+$; NMR δ (CDCl$_3$); 4.85 (2H, d, J=5.6 Hz), 5.94 (1H, brs), 7.24 (1H, d, J=8.4 Hz), 7.43 (1H, d, J=8.4 Hz), 7.70 (1H, d, J=9.2 Hz), 7.72 (1H, s), 7.83 (1H, d, J=9.2 Hz), 8.68 (1H, s).

EXAMPLE 59

4-(3,4-Dimethoxybenzyl)amino-6-chloroquinazoline

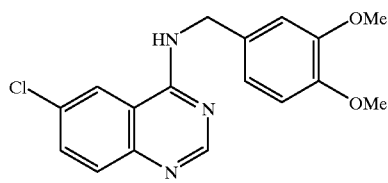

molecular formula; $C_{17}H_{16}N_3O_2Cl$; yield(%); 73; m.p.(° C.); 174~175; Mass; 330 (M+H)$^+$; NMR δ (CDCl$_3$); 3.87 (6H, s), 4.78 (2H, d, J=5.2 Hz), 6.85 (1H, d, J=8.0 Hz), 6.96 (1H, d, J=8.0 Hz), 6.98 (1H, s), 7.34 (1H, brs), 7.65 (1H, dd, J=9.2 Hz, 2.0 Hz), 7.78 (1H, d, J=9.2 Hz), 8.08 (1H, d, J=2.0 Hz), 8.65 (1H, s).

EXAMPLE 60

4-(Benzimidazol-5-ylmethyl)amino-6-chloroquinazoline

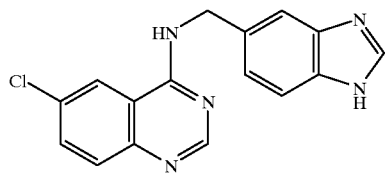

molecular formula; $C_{16}H_{12}N_5Cl$; yield(%); 76; m.p.(° C.); 243~244 (dec.); Mass; 310 (M+H)$^+$; NMR δ (DMSO-d$_6$); 4.89 (2H, d, J=5.6 Hz), 7.27 (1H, d, J=8.4 Hz), 7.55 (1H, d, J=8.4 Hz), 7.59 (1H, s), 7.72 (1H, d, J=8.8 Hz), 7.80 (1H, dd, J=8.8 Hz, 2.4 Hz), 8.25 (1H, s), 8.50 (1H, s), 8.53 (1H, d, J=2.4 Hz), 9.07 (1H, brt, J=5.6 Hz).

EXAMPLE 61

4-(2-Methoxy-2,3-dihydrobenzofuran-5-yl) methylamino-6-chloroquinazoline

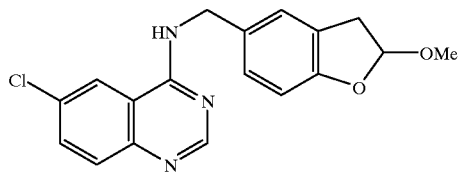

molecular formula; $C_{18}H_{16}N_3O_2Cl$ (341.798); yield(%); 53; m.p.(° C.); 178~179; Mass; 342 (M+H)$^+$; NMR δ (DMSO-d$_6$); 2.88 (1H, dd, J-2.0 Hz, 17.0 Hz), 3.28~3.34 (1H, m), 4.68 (1H, d, J=5.7 Hz), 5.68 (1H, dd, J=2.0 Hz, 6.6 Hz), 6.79 (1H, d, J=8.2 Hz), 7.14 (1H, d, J=8.2 Hz), 7.24 (1H, s), 7.70 (1H, d, J=9.0 Hz), 7.79 (1H, dd, J=2.2 Hz, 9.0 Hz), 8.46 (1H, d, J=2.2 Hz), 8.48 (1H, s), 8.82 (1H, t, J=5.7 Hz).

EXAMPLE 62

4-(2-Methylbenzimidazol-5-ylmethyl)amino-6-chloroquinazoline

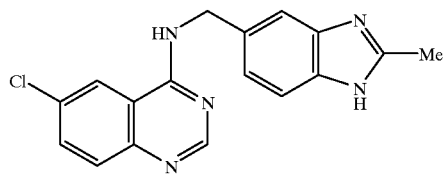

molecular formula; $C_{17}H_{14}N_5Cl$; yield(%); 17; m.p.(° C.); 273~274 (dec.); Mass; 324 (M+H)$^+$; NMR δ (DMSO-d$_6$); 2.71 (3H, s), 4.94 (2H, d, J=5.6 Hz), 7.48 (1H, d, J=8.4 Hz), 7.63 (1H, d, J=8.4 Hz), 7.70 (1H, s), 7.77 (1H, d, J=8.8 Hz), 7.86 (1H, dd, J=8.8 Hz, 2.0 Hz), 8.58 (1H, s), 8.65 (1H, d, J=2.0 Hz), 9.65 (1H, brs).

EXAMPLE 63

4-[1-Methyl-1(3,4-methylenedioxyphenyl)ethyl] amino-6-chloroquinazoline

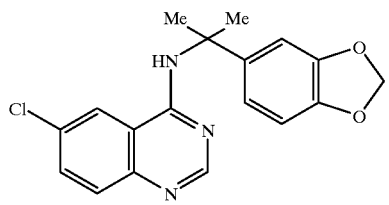

molecular formula; $C_{18}H_{16}N_3O_2Cl$; yield(%,); 32; m.p.(° C.); 175~176; Mass; 342 (M+H)$^+$; NMR δ (CDCl$_3$); 1.92 (6H, s), 5.95 (2H, s), 6.14 (1H, brs), 6.76 (1H, d, J=7.6 Hz), 6.92 (1H, d, J=7.6 Hz), 6.93 (1H, s), 7.67 (1H, dd, J=8.8 Hz), 7.77 (1H, d, J=2.0 Hz), 7.86 (1H, d, J=8.8 Hz), 8.50 (1H, s).

EXAMPLE 64

4-(3,4-Methylenedioxybenzyl)amino-6-ethoxyquinazoline

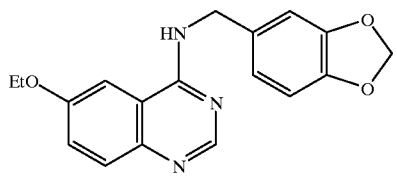

molecular formula; $C_{18}H_{17}N_3O_3$; yield(%); 44; m.p.(° C.); 190~191; Mass; 324 (M+H)$^+$; NMR δ (CDCl$_3$); 1.46 (3H, t, J=6.8 Hz), 4.10 (2H, q, J=6.8 Hz), 4.77 (2H, d, J=5.2 Hz), 5.68 (1H, brs), 5.97 (2H, s), 6.80 (1H, d, J=8.0 Hz), 6.87~6.92 (3H, m), 7.39 (1H, dd, J=9.2 Hz, 2.8 Hz), 7.79 (1H, d, J=9.2 Hz), 8.62 (1H, s).

EXAMPLE 65

4-(3,4-Methylenedioxylbenzyl)amino-6-cyanoquinazoline

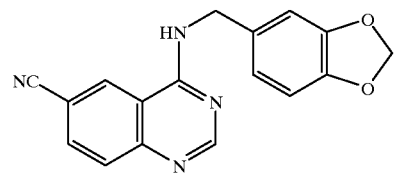

15 ml of isopropyl alcohol, 75 mg of triethylamine and 125 mg of piperonylamine were added to 140 mg of 4-chloro-6-cyanoquinazoline. The obtained mixture was heated under reflux for 5 hours and filtered to recover a precipitate. This precipitate was introduced to a silica gel column, followed by eluting with ethyl acetate to give 200 mg of the title compound.

molecular formula; $C_{17}H_{12}N_4O_2$; yield(%); 89; m.p.(° C.); 243~244; Mass; 305 (M+1)$^+$; NMR δ (DMSO-d$_6$); 4.67 (2H, d, J=5.6 Hz), 5.96 (2H, s), 6.84 (2H, s), 6.95 (1H, s), 7.77 (1H, d, J=8.4 Hz), 8.56 (1H, s), 8.89 (1H, s), 9.04 (1H, br).

EXAMPLES 66 TO 85

The following compounds were prepared in a similar manner to that of Example 65.

EXAMPLE 66

4-[3-(1-Imidazolyl)-propyl]amino-6-cyanoquinazoline

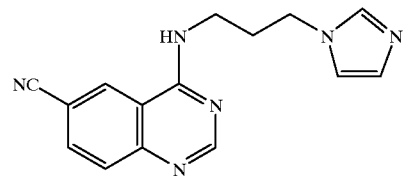

molecular formula; $C_{15}H_{14}N_6$; yield(%); 22; m.p.(° C.); 196~197; Mass m/e; 279 (M+1)$^+$; NMR δ (CDCl$_3$); 2.27

(2H, quintet, J=6.4 Hz), 3.66 (2H, q, J=6.4 Hz), 4.17 (2H, t, J=6.4 Hz), 7.07 (1H, s), 7.11 (1H, s), 7.82 (1H, s), 7.82 (1H, s), 8.09 (1H, s), 8.37 (1H, brs), 8.66 (1H, s), 8.84 (1H, s).

EXAMPLE 67

4-(Benzimidazol-5-yl)methylamino-6-cyanoquinazoline

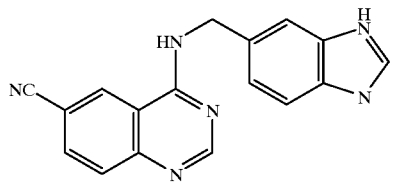

molecular formula; $C_{17}H_{12}N_6$; yield(%); 68; m.p.(° C.); 274~277; Mass; 301 (M+1)$^+$; NMR δ (DMSO-d$_6$); 4.88 (2H, d, J=5.6 Hz), 7.21~7.24 (1H, m), 7.35~7.76 (2H, m), 7.78 (1H, d, J=8.8 Hz), 7.06 (1H, dd, J=8.8 Hz, 1.6 Hz), 8.15 (1H, s), 8.57 (1H, s), 8.92 (1H, s), 9.14 (1H, m), 12.32 (1H, m).

EXAMPLE 68

4-(3,4-Methylenedioxybenzyl)amino-6-ethoxycarbonylquinazoline

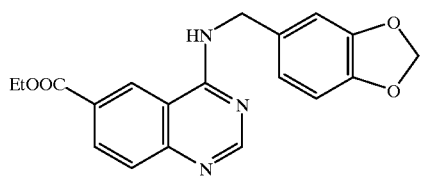

molecular formula; $C_{19}H_{17}N_3O_4$; yield(%); 48; m.p.(° C.); 156~157; Mass; 352 (M+H)$^+$; NMR δ (CDCl$_3$); 1.43 (3H, t, J=7.2 Hz), 4.44 (2H, q, J=7.2 Hz), 4.79 (2H, d, J=5.2 Hz), 5.98 (2H, s), 6.14 (1H, brs), 6.82 (1H, d, J=8.0 Hz), 6.89 (1H, d, J=8.0 Hz), 6.90 (1H, s), 7.87 (1H, d, J=8.8 Hz), 8.33 (1H, d, J=8.8 Hz), 8.46 (1H, s), 8.74 (1H, s).

EXAMPLE 69

4-(3,4-Methylenedioxybenzyl)amino-6-methylquinazoline

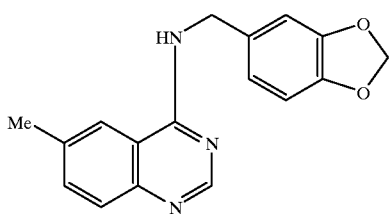

molecular formula; $C_{17}H_{15}N_3O_2$; yield(%); 68; m.p.(° C.); 203~204; Mass; 294 (M+H)$^+$; NMR δ (CDCl$_3$); 2.49 (3H, s), 4.76 (2H, d, J=5.6 Hz), 5.79 (1H, brs), 5.96 (2H, s), 6.81 (1H, d, J=8.0 Hz), 6.88 (1H, d, J=8.0 Hz), 6.91 (1H, s), 7.44 (1H, s), 7.57 (1H, d, J=8.4 Hz), 7.76 (1H, d, J=8.4 Hz), 8.66 (1H, s).

EXAMPLE 70

4-(3, 4-Methylenedioxybenzyl) amino-6,7-dimethoxyquinazoline

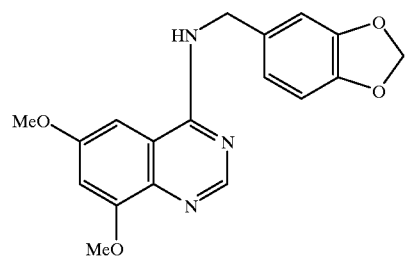

molecular formula; $C_{18}H_{17}N_3O_4$; yield(%); 77; m.p.(° C.); 221~222; Mass; 340 (M+H)$^+$; NMR δ (DMSO-d$_6$); 3.88 (3H, s), 3.89 (3H, s), 4.68 (2H, d, J=6.0 Hz), 5.97 (2H, s), 6.85 (2H, s), 6.94 (1H, s), 7.09 (1H, s), 7.64 (1H, s), 8.33 (1H, s), 8.37 (1H, t, J=6.0 Hz).

EXAMPLE 71

4-(3, 4-Methylenedioxybenzyl)amino-6,8-dimethoxyquinazoline

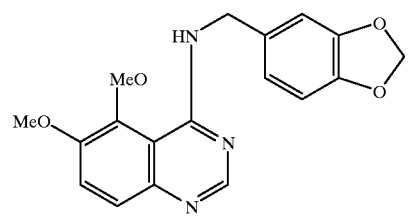

molecular formula; $C_{18}H_{17}N_3O_4$; yield(%); 88; m.p.(° C.); 217~218; Mass; 340 (M+H)$^+$; NMR δ (CDCl$_3$); 3.89 (3H, s), 4.01 (3H, s), 4.77 (2H, d, J=5.2 Hz), 5.63 (1H, brs), 5.97 (2H, s), 6.42 (1H, d, J=2.4 Hz), 6.77 (1H, d, J=2.4 Hz), 6.80 (1H, d, J=7.6 Hz), 6.88 (1H, dd, J=7.6 Hz, 1.6 Hz), 6.92 (1H, d, J=1.6 Hz), 8.65 (1H, s).

EXAMPLE 72

4-(3,4-Methylenedioxybenzyl)amino-5,6-dimethoxyguinazoline molecular formula; $C_{18}H_{17}N_3O_4$; yield(%); 74; m.p.(° C.); 122~123; Mass; 340 (M+H)$^+$; NMR δ (CDCl$_3$); 3.97 (6H, s), 4.77 (2H, d, J=5.2 Hz), 5.97 (2H, s), 6.81 (1H, d, J=8.0 Hz), 6.86 (1H, dd, J=8.0 Hz, 1.6 Hz), 6.88 (1H, d, J=1.6 Hz), 7.49 (1H, d, J=8.8 Hz), 7.82 (1H, d, J=8.8 Hz), 8.51 (1H, s), 8.64 (1H, brs).

EXAMPLE 73

4-(3,4-Methylenedioxybenzyl)amino-6-acetamido-7-methoxyquinazoline

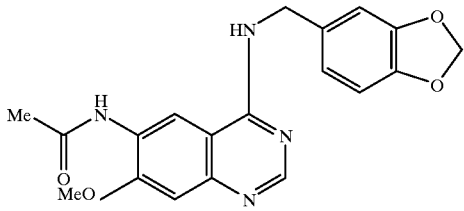

molecular formula; $C_{19}H_{18}N_4O_4$; yield(%); 66; m.p.(° C.); 164~165; Mass; 367 (M+H)⁺; NMR δ (CDCl₃); 2.26 (3H, s), 4.04 (3H, s), 4.76 (2H, d, J=5.6 Hz), 5.95 (2H, s), 6.22 (1H, brs), 6.77 (1H, d, J=8.0 Hz), 6.85 (1H, d, J=8.0 Hz), 6.89 (1H, s), 7.31 (1H, s), 8.02 (1H, brs), 8.59 (1H, s), 8.81 (1H, s).

EXAMPLE 74

4,(3,4-Methylenedioxybenzyl)amino-6-methylthio-7-methoxyquinazoline

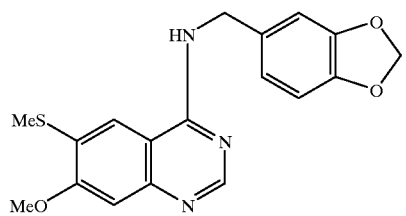

molecular formula; $C_{18}H_{17}N_3O_3S$; yield(%); 39; m.p.(° C.); 200~205 (dec.); Mass; 356 (M+H)⁺; NMR δ (CDCl₃); 2.50 (3H, s), 4.01 (3H, s), 4.78 (2H, d, J=5.6 Hz), 5.95 (2H, s), 6.13 (1H, brs), 6.79 (1H, d, J=8.0 Hz), 6.88 (1H, d, J=8.0 Hz), 6.91 (1H, s), 7.15 (1H, s), 7.33 (1H, s), 8.56 (1H, s).

EXAMPLE 75

4-(3,4-Methylededioxybenzyl)aminoquinazoline

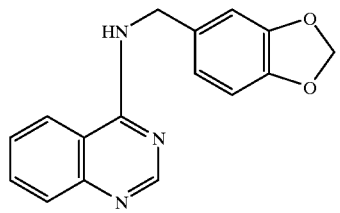

molecular formula; $C_{16}H_{13}N_3O_2$; yield(%); 69; m.p.(° C.); 197~198; Mass; 280 (M+H)⁺; NMR δ (CDCl₃); 4.78 (2H, d, J=5.2 Hz), 5.85 (1H, brs), 5.96 (2H, s), 6.80 (1H, d, J=8.0 Hz), 6.88 (1H, d, J=8.0 Hz), 6.91 (1H, s), 7.46 (1H, t, J=8.0 Hz), 7.68 (1H, d, J=8.0 Hz), 7.75 (1H, t, J=8.0 Hz), 7.87 (1H, d, J=8.0 Hz), 8.71 (1H, s).

EXAMPLE 76

4-(3, 4-Methylededioxybenzyl) amino-8-methoxyquinazoline

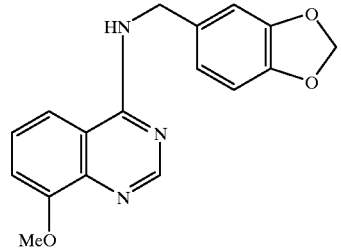

molecular formula; $C_{17}H_{15}N_3O_3$; yield(%); 76; m.p.(° C.); 195~196; Mass; 310 (M+H)⁺; NMR δ (CDCl₃); 4.03 (3H, s), 4.78 (2H, d, J=5.6 Hz), 5.94 (2H, s), 6.77 (1H, d, J=8.0 Hz), 6.89 (1H, d, J=8.0 Hz), 6.92 (1H, s), 6.95 (1H, brs), 7.12 (1H, d, J=8.0 Hz), 7.39 (1H, t, J=8.0 Hz), 7.48 (1H, d, J=8.0 Hz), 8.70 (1H, s).

EXAMPLE 77

4-(3,4-Methylenedioxybenzyl)amino-7-chloroquinazoline

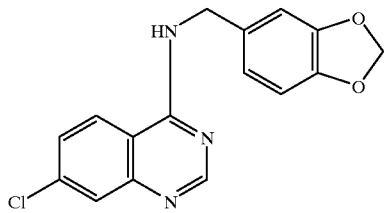

molecular formula; $C_{21}H_{22}N_3O_2Cl$; yield(%); 62; m.p.(° C.); 209~210; Mass; 314 (M+H)⁺; NMR δ (CDCl₃); 4.77 (2H, d, J=5.6 Hz), 5.95 (2H, s), 6.78 (1H, d, J=8.0 Hz), 6.88 (1H, d, J=8.0 Hz), 6.92 (1H, s), 7.39 (1H, dd, J=8.8 Hz, 2.0 Hz), 7.4 (1H, brs), 7.83 (1H, d, J=2.0 Hz), 7.96 (1H, d, J=8.8 Hz), 8.63 (1H, s).

EXAMPLE 78

4-(3,4-Methylenedioxybenzyl)aminobenzo[g]quinazoline

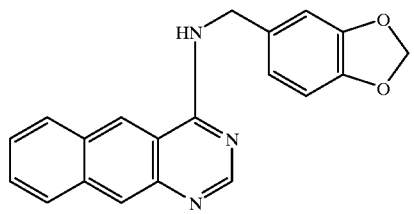

molecular formula; $C_{20}H_{15}N_3O_2$ (329); yield(%); 45; m.p.(° C.); 265 (dec.); Mass; 330 (M+1)⁺; NMR δ (DMSO-d₆); 4.92 (2H, d, J=6.0 Hz), 5.97 (2H, s), 6.88 (1H, d, J=8.0 Hz), 6.94 (1H, dd, J=8.0 Hz, 1.6 Hz), 7.06 (1H, d, J=1.6 Hz), 7.68 7.81 (2H, m), 8.11 (1H, d, J=8.4 Hz), 8.21 (1H, d, J=8.4 Hz), 8.33 (1H, s), 8.90 (1H, s), 9.36 (1H, s), 11.09 (1H, br).

EXAMPLE 79

4-(3,4-Methylenedioxybenzyl)amino-6,7-methylenedioxyquinazoline

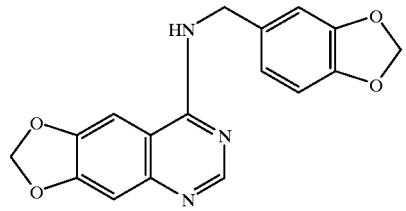

molecular formula; $C_{17}H_{13}N_3O_4$ (323); yield(%); 55; m.p.(° C.); 229~231; Mass; 324(M+1)$^+$; NMR δ (DMSO-$d_6$); 4.62 (2H, d, J=5.6 Hz), 5.94 (2H, s), 6.16 (2H, s), 6.79 (1H, d, J=8.0 Hz), 6.82 (1H, dd, J=8.0 Hz, 2.0 Hz), 6.89 (1H, d, J=2.0 Hz), 7.06 (1H,s), 7.68 (1H, s), 8.26 (1H, brt, J=5.6 Hz), 8.28 (1H, s).

EXAMPLE 80

4-(3.4,5-Trimethoxybenzyl)amino-6,7-methylenedioxyquinazoline

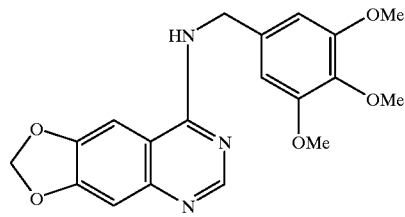

molecular formula; $C_{19}H_{19}N_3O_5$ (369); yield(%); 59; m.p.(° C.); 240~241; Mass; 370 (M+1)$^+$; NMR δ (DMSO-$d_6$); 3.61 (3H, s), 3.70 (6H, s), 4.65 (2H, d, J=6.0 Hz), 6.16 (2H, s), 6.675 (2H, s), 7.06 (1H, s), 7.72 (1H, s), 8.23 (1H, brt, J=6.0 Hz), 8.30 (1H, s).

EXAMPLE 81

2-Methyl-4-(3,4-methylenedioxybenzyl)amino-6,7,8-trimethoxyquinazoline

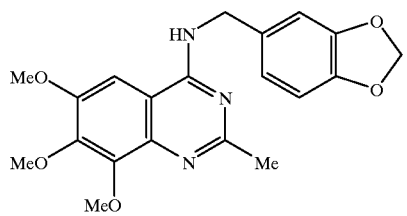

molecular formula; $C_{20}H_{21}N_3O_5$; yield(%); 58; m.p.(° C.); 190~191; Mass; 384 (M+H)$^+$; NMR δ (CDCl$_3$); 2.67 (3H, s), 3.93 (3H, s), 4.01 (3H, s), 4.11 (3H, s), 4.77 (2H, d, J=5.2 Hz), 5.96 (2H, s), 6.70 (1H, s) 6.79 (1H, d, J=7.6 Hz), 6.89 (1H, d, J=7.6 Hz), 6.93 (1H, s).

EXAMPLE 82

2-Isopropyl-4-(3,4-methylenedioxybenzyl)amino-6-methoxyquinazoline

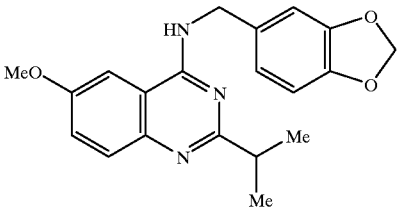

molecular formula; $C_{20}H_{21}N_3O_3$; yield(%); 84; m.p.(° C.); 157~158; Mass; 352 (M+1)$^+$; NMR δ (CDCl$_3$); 1.36 (6H, d, J=6.8 Hz), 3.15 (1H, septet, J=6.8 Hz), 3.88 (3H, s), 4.81 (2H, d, J=5.6H), 5.94 (2H, s), 6.78 (1H, d, J=8.0 Hz), 6.91 (1H, dd, J=8.0 Hz, 2.0 Hz), 6.96 (1H, d, J=2.0 Hz), 6.99 (1H, brd, J=2.4 Hz), 7.32 (1H, dd, J=9.2 Hz, 2.4 Hz), 7.79 (1H, d, J=9.2 Hz).

EXAMPLE 83

4-(3,4-Methylenedioxybenzamido)-6,7,8-trimethoxyquinazoline

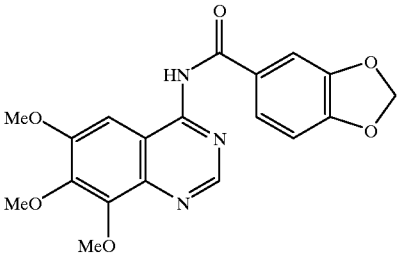

molecular formula; $C_{19}H_{17}N_3O_6$; yield(%); 13; m.p.(° C.); 190~192; Mass; 384 (M+H)$^+$; NMR δ (CDCl$_3$); 4.10 (6H, s), 4.12 (3H, s), 6.07 (2H, s), 6.91 (1H, d, J=8.0 Hz), 7.86 (1H, s), 7.90 (1H, s), 8.06 (1H, d, J=8.0 Hz), 8.18 (1H,s).

EXAMPLE 84

4-(3,4-Methylenedioxybenzyl)oxy-6,7,8-trimethoxyquinazoline

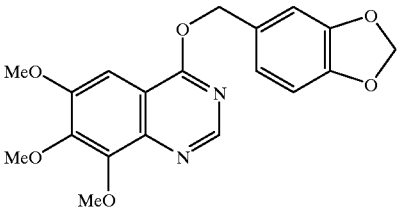

molecular formula; $C_{19}H_{18}N_2O_6$; yield(%); 49; m.p.(° C.); 141~142; Mass; 371 (M+H)$^+$; NMR δ (CDCl$_3$); 3.97 (3H, s), 4.05 (3H, s), 4.13 (3H, s), 5.53 (2H, s), 5.99 (2H, s), 6.84 (1H, d, J=8.0 Hz), 7.00 (1H, dd, J=8.0 Hz, 2.0 Hz), 7.02 (1H, d, J=2.0 Hz), 7.20 (1H, s), 8.74 (1H, s).

EXAMPLE 85

4-(3, 4-Methylenedioxybenzyl)oxy-6-methylthioquinazoline

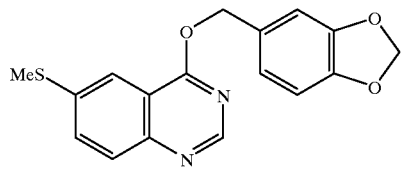

molecular formula; $C_{17}H_{14}N_2O_3Cl$; yield(%); 69; m.p.(° C.); 104~105; Mass; 327 (M+H)$^+$; NMR δ (CDCl$_3$); 2.59 (3H, s), 5.56 (2H, s), 6.00 (2H, s), 6.85 (1H, d, J=8.0 Hz), 7.01 (1H, dd, J=8.0 Hz, 1.6 Hz), 7.03 (1H, d, J=1.6 Hz), 7.72 (1H, dd, J=8.8 Hz, 1.6 Hz), 7.88 (1H, d, J=8.8 Hz), 7.89 (1H, d, J=1.6 Hz), 8.78 (1H, s).

EXAMPLE 86

2,4,6-Trimethoxyquinazoline

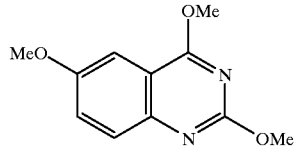

5.0 g(0.022 mol) of 2.4-dichloro-6-methoxyquinazoline was suspended in 150 ml of methanol, followed by the gradual addition of 3.5 g of sodium hydride. The obtained mixture was heated under reflux. After several hours, the reaction mixture was concentrate under a reduced pressure, followed by the addition of water. The crystalline precipitate thus formed was recovered by filtration, washed with water and air-dried to give 4.8 g of the title compounds as a crude yellow crystal.

m.p.; 143~144; Mass; 221 (M+1)$^+$; NMR δ (CDCl$_3$); 3.90 (3H, s), 4.08 (3H, s), 4.18 (3H, s), 7.36 (1H, d, J=2.8 Hz), 7.39 (1H, dd, J=8.8 Hz, 2.8 Hz), 7.67 (1H, d, J=2.8 Hz).

EXAMPLE 87

2,6-Dimethoxy-4-(3,4-methylenedioxybenzyl)aminoquinazoline

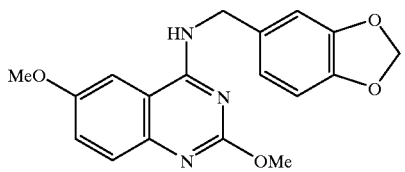

3.75 g (24.8 mmol) of piperonylamine was added to a solution of 2.00 g (8.26 mmol) of the 2,4,6-trimethoxyquinazoline prepared in Example 88 in dimethyl sulfox (15 ml). The obtained mixture was stirred under heating at 150 to 160° C. After one hour, the reaction mixture was purified by silica gel column chromatography (ethyl acetate/n-hexane) and recrystallized from ethyl acetate/n-hexane to give 0.50 g of the title compounds as a pale-yellow crystal.

molecular formula; $C_{18}H_{17}N_3O_4$; yield(%); 18; m.p.(° C.); 166~167; Mass; 340 (M+1)$^+$; NMR δ (CDCl$_3$); 3.89 (3H, s), 4.03 (3H, s), 4.77 (2H, d, J=5.2 Hz), 5.94 (2H, s), 6.76 (1H, d, J=8.0 Hz), 6.89 (1H, dd, J=8.0 Hz, 1.2 Hz), 6.93 (1H, d, J=1.2 Hz), 7.29 (1H, dd, J=8.8 Hz, 2.8 Hz), 7.32 (1H, brs), 7.59 (1H, d, J=8.8 Hz).

EXAMPLE 88

2,4-Bisbenzyloxy-6-methoxyquinazoline

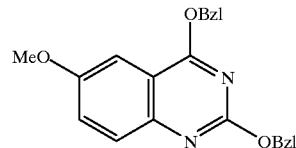

3 ml of benzyl alcohol was dissolved in 50 ml of tetrahydrofuran, followed by the addition of 1.0 g of sodium hydride. The obtained mixture was stirred at 40 to 50° C. for 30 minutes, followed by the addition of 2.50 g (0.0109 mol) of 2,4-dichloro-6-methoxyquinazoline. The obtained mixture was heated under reflux for several hours, followed by the addition of water. The obtained mixture was extracted with chloroform and the organic layer was dried over anhydrous magnesium sulfate and filtered. The filtrate was distilled under a reduced pressure to remove the solvent. The obtained crystalline residue was recrystallized from chloroform/n-hexane to give 3.84 g of the title compound as a yellow crystal.

yield(%); 95; m.p.(° C.); 144~145; Mass; 373 (M+1)$^+$; NMR δ (CDCl$_3$); 3.87 (3H, s), 5.53 (2H, s), 5.62 (2H, s), 7.31~7.55 (12H, m), 7.70 (1H, d, J=8.8 Hz).

EXAMPLE 89

2-Benzyloxy-4-(3,4-methylenedioxybenzyl)amino-6-methoxyguinazoline

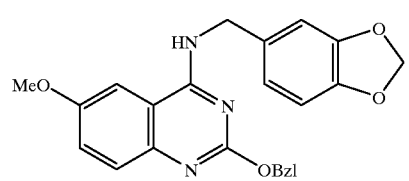

1.25 g (8.27 mmol) of piperonylamine was added to a solution of 1.00 g (2.69 mmol) of the 2,4-bisbenzyloxy-6-methoxyquinazoline prepared in Example 90 in dimethyl sulfoxide (10 ml). The obtained mixture was stirred at 160 to 180° C. After one hour, the reaction mixture was purified by silica gel column chromatography (ethyl acetate/n-hexane) and recrystallized from ethyl acetate/n-hexane to give 0.20 g of the title compound as a colorless needle.

molecular formula; $C_{24}H_{21}N_3O_4$; yield(%); 18; m.p.(° C.); 163~164; Mass; 416 (M+H)$^+$; NMR δ (CDCl$_3$); 3.86 (3H, s), 4.75 (2H, d, J=5.2 Hz), 5.49 (2H, s), 5.68 (1H, brs), 5.96 (2H, s), 6.79 (1H, d, J=8.0 Hz), 6.84~6.87 (3H, m), 7.28~7.36 (4H, m), 7.51~7.53 (2H, m), 7.63 (1H, d, J=9.2 Hz).

EXAMPLE 90

2,6-Dichloro-4-(3,4-methylenedioxybenzyl)aminoquinazoline

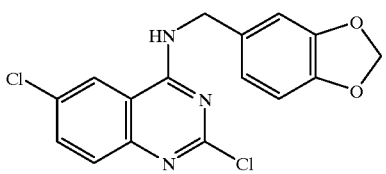

A mixture comprising 3.6 g of 2,4,6-trichloroquinazoline, 2.4 g of piperonylamine, 1.6 g of triethylamine and 50 ml of isopropyl alcohol was heated under reflux for 1.5 hours and hot-filtered to give 5.2 g of the title compound as a filter cake.

molecular formula; $C_{16}H_{11}N_3O_2Cl_2$; yield(%); 98; m.p.(° C.); 215; Mass; 349 (M+1)$^+$; NMR δ (DMSO-D$_6$); 4.61 (2H, s), 5.97 (2H, s), 6.85 (2H, s), 6.95 (1H, s), 7.63 (1H, d, J=8.8 Hz), 7.80 (1H, dd, J=8.8 Hz, 2.4 Hz), 8.45 (1H, d, J=2.4 Hz), 9.24 (1H, br).

EXAMPLE 91

2-Chloro-4-(3,4-methylenedioxybenzyl)amino-6-cyanoquinazoline

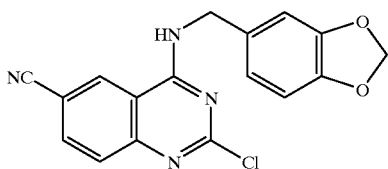

35 ml of isopropyl alcohol, 900 mg of triethylamine and 1.35 g of piperonylamine were added to 2 g of 2,4-dichloro-6-cyanoquinazoline. The obtained mixture was heated under reflux for 1.5 hours and hot-filtered to recover a precipitate. Thus, 2.4 g of the title compound was obtained.

molecular formula; $C_{17}H_{11}N_4O_2Cl$; yield(%); 79; m.p.(° C.); 234~236 (dec.); Mass; 339 (M+1)$^+$; NMR δ (DMSO-d$_6$); 4.63 (2H, d, J=5.6 Hz), 5.97 (2H, s), 6.86 (2H, s), 6.97 (1H, s), 7.72 (1H, d, J=8.4 Hz), 8.10 (1H, dd, J=8.4 Hz, 1.8 Hz), 8.90 (1H, d, J=1.8 Hz), 9.50 (1H, br).

EXAMPLE 92

2-Chloro-4-(3-chloro-4-methoxybenzyl)amino-6-cyanoquinazoline

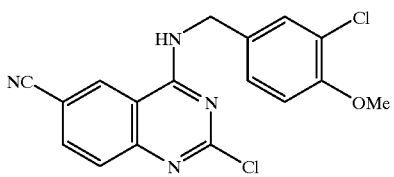

3.9 g of 3-chloro-4-methoxybenzylamine, 3.97 g of triethylamine and 200 ml of 2-propanol were added to 4 g of 2,4-dichloro-6-cyanoquinazoline. The obtained mixture was refluxed for 30 minutes, cooled to room temperature and filtered to recover a crystalline precipitate. The precipitate was washed with water and chloroform successively to give 5.563 g of the title compound.

molecular formula; $C_{17}H_{12}N_4OCl_2$; yield(%); 87; m.p.(° C.); 264~266; Mass m/e; 359 (M+1); NMR δ (CDCl$_3$); 3.90 (3H, s), 4.73 (2H, d, J=5.2 Hz), 6.92 (1H, d, J=8.4), 7.33 (1H, dd, J=8.4 Hz, 2.0 Hz), 7.45 (1H, d, J=2.0 Hz), 7.74 (1H, d, J=8.4 Hz), 7.83 (1H, dd, J=8.4 Hz, 1.6 Hz), 8.78 (1H, d, J=1.6 Hz), 8.85 (1H, brs).

EXAMPLES 93 TO 103

The following compounds were prepared in a similar manner to those of Examples 86 to 92.

EXAMPLE 93

2-Chloro-4-(3,4-methylenedioxybenzyl)amino-6,7,8-trimethoxyquinazoline

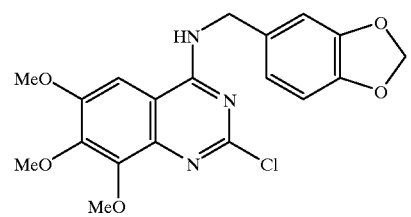

molecular formula; $C_{19}H_{18}N_3O_5Cl$; yield(%); 50; m.p.(° C.); 193~194; Mass; 404 (M+H)$^+$; NMR δ (CDCl$_3$); 3.94 (3H, s), 4.03 (3H, s), 4.10 (3H, s), 4.75 (2H, d, J=5.2 Hz), 5.65 (1H, brs), 5.98 (2H, s), 6.59 (1H, s), 6.81 (1H, d, J=8.0 Hz), 6.89 (1H, d, J=8.0 Hz), 6.91 (1H, s).

EXAMPLE 94

2-Chloro-4-(3-chloro-4-methoxybenzyl)amino-6,7,8-trimethoxyquinazoline

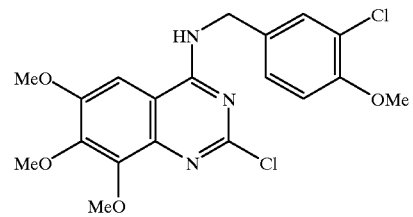

molecular formula; $C_{19}H_{19}Cl_2N_3O_4$; yield(%); 45; m.p.(° C.); 199~200; Mass; 424 (M+1)$^+$; NMR δ (CDCl$_3$); 3.89 (3H, s), 3.95 (3H, s), 4.02 (3H, s), 4.08 (3H, s), 4.76 (2H, d, J=5.6 Hz), 6.39 (1H, brs), 6.83 (1H, s), 6.89 (1H, d, J=8.3 Hz), 7.31 (1H, dd, J=8.4 Hz, 2.0 Hz), 7.40 (1H, d, J=2.0 Hz).

EXAMPLE 95

2-Chloro-4-(3,4-methylenedioxybenzyl)amino-6,7-dimethoxyquinazoline

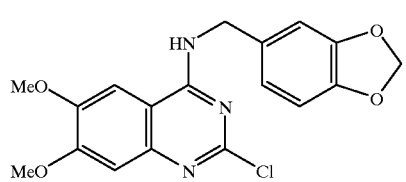

molecular formula; $C_{18}H_{16}N_3O_4Cl$; yield(%); 97; m.p.(° C.); 177~178; Mass; 374(M+H)$^+$; NMR δ (CDCl$_3$); 3.95 (3H, s), 3.97 (3H, s), 4.75 (2H, d, J=5.2 Hz), 5.74 (1H, brt, J=5.2 Hz), 5.97 (2H, s), 6.80 (1H, d, J=8.0 Hz), 6.81 (1H, s), 6.88 (1H, dd, J=8.0 Hz, 2.0 Hz), 6.91 (1H, d, J=2.0 Hz), 7.14 (1H, s).

EXAMPLE 96

2-Chloro-4-(3,4-methylenedioxybenzyl)amino-6-methoxyquinazoline

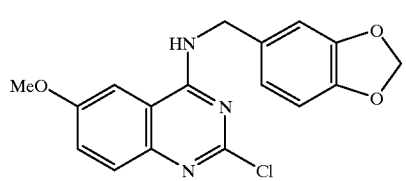

molecular formula; $C_{17}H_{14}N_3O_3Cl$; yield(%); 80; m.p.(° C.); 202~203; Mass; 344 (M+1)$^+$; NMR δ (CDCl$_3$); 3.91 (3H, s), 4.77 (2H, d, J=5.6 Hz), 5.94 (2H, s), 6.76 (1H, d, J=8.0 Hz), 6.91 (1H, dd, J=8,0 Hz, 1.6 Hz), 6.95 (1H, d, J=1.6 Hz), 7.35 (1H, dd, J=9.2 Hz, 2.8 Hz), 7.46 (1H, brd, J=2.8 Hz), 7.69 (1H, d, J=9.2 Hz), 7.90 (1H, brs).

EXAMPLE 97

2-Chloro-4-(3-chloro-4-methoxybenzyl)amino-6-methoxyquinazoline

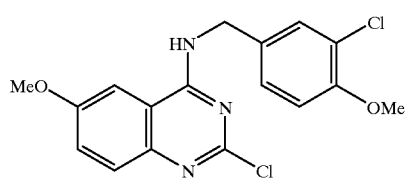

molecular formula; $C_{17}H_{15}N_3O_2Cl_2$; yield(%); 88; m.p.(° C.); 171~172; Mass; 364 (M+1)$^+$; NMR δ (DMSO); 3.83 (3H, s), 3.88 (3H, s), 4.68 (2H, d, J=5.6 Hz), 7.13 (1H, d, J=8.8 Hz), 7.33 (1H, dd, J=2.4 Hz, 8.8 Hz), 7.44 (1H, dd, J=2.8 Hz, 9.2 Hz), 7.46 (1H, d, J=2.4 Hz), 7.58 (1H, d, J=9.2 Hz), 7.72 (1H, d, J=2.8 Hz), 9.05 (1H, t, J=5.6 Hz).

EXAMPLE 98

2,6-Dichloro-4-benzylaminoquinazoline

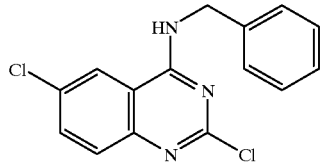

molecular formula; $C_{15}H_{11}N_3 Cl_2$; yield(%); 77; m.p.(° C.); 227~228; NMR δ (CDCl$_3$); 4.85 (2H, d, J=5.2 Hz), 5.97 (1H, brs), 733~7.43 (5H, m), 7.62 (1H, d, J=2.0 Hz), 7.68 (1H, dd, J=8.8 Hz, 2.0 Hz), 7.74 (1H, d, J=8.8 Hz).

EXAMPLE 99

2,6-Dichloro-4-[2-(3,4-methylenedioxyphenyl)ethyl]aminoquinazoline

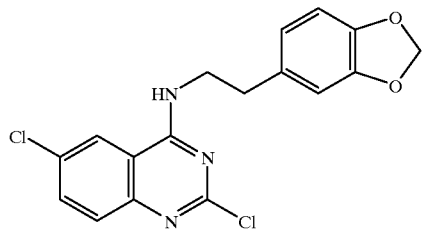

molecular formula; $C_{17}H_{13}N_3O_2Cl_2$; yield(%); 71; m.p.(° C.); 228~229; NMR δ (DMSO-d$_6$); 2.88 (2H, t, J=7.4 Hz), 3.68 (2H, m), 5.96 (2H, s), 6.70 (1H, dd, J=8.0 Hz, 1.6 Hz), 6.81 (1H, d, J=8.0 Hz), 6.87 (1H, d, J=1.6 Hz), 7.63 (1H, d, J=8.8 Hz), 7.80 (1H, dd, J=8.8 Hz, 2.0 Hz), 8.40 (1H, d, J=2.0 Hz), 8.86 (1H, d, J=5.2 Hz).

EXAMPLE 100

2,6-Dichloro-4-(3-chloro-4-methoxybenzyl)aminoquinazoline

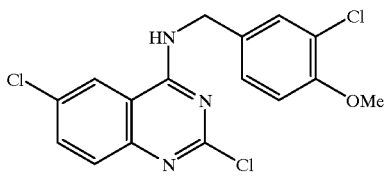

molecular formula; $C_{16}H_{12}N_3OCl_3$; yield(%); 93; m.p.(° C.); 207~208; Mass m/e; 368 (M+1); NMR δ (CDCl$_3$); 3.90 (3H, s), 4.73 (2H, d, J=5.6 Hz), 6.91 (1H, d, J=8.4 Hz), 7.32 (1H, d, J=8.4 Hz, 2.0 Hz), 7.45 (1H, d, J=2.0 Hz), 7.62 (1H, dd, J=8.8 Hz, 2.0 Hz), 7.66 (1H, d, J=8.8 Hz), 8.07 (1H, brs), 8.16 (1H, d, J=2.0 Hz).

EXAMPLE 101

2,6-Dichloro-4-(benzimidazol-5-yl)methylaminoquinazoline

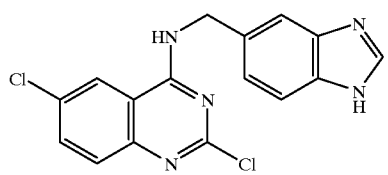

molecular formula; $C_{16}H_{11}N_5Cl_2$ (344.205); yield(%); 81; m.p.(° C.);>290; Mass; 344 (M+1)$^+$; NMR δ (DMSO); 4.85 (2H, d, J=6.0 Hz), 7.25 (1H, dd, J=1.6 Hz, 6.4 Hz), 7.57 (1H, d, J=6.4 Hz), 7.60 (1H, s), 7.66 (1H, d, J=8.8 Hz), 7.83 (1H, dd, J=2.0 Hz, 8.8 Hz), 8.21 (1H, s), 8.44 (1H, brs), 8.52 (1H, d, J=2.0 Hz), 9.37 (1H, t, J=6.0 Hz).

EXAMPLE 102

2-Chloro-4-(benzimidazol-5-yl)methylamino-6-cyanoquinazoline

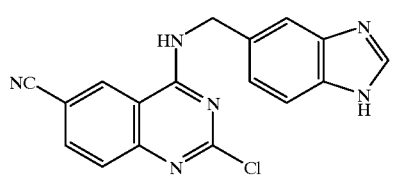

molecular formula; $C_{17}H_{11}N_6Cl$ (334.5); yield(%); 58; m.p.(° C.);>290; Mass; 335 (M+1)$^+$; NMR δ (DMSO-$d_6$); 4.81 (2H, s), 7.21 7.68 (3H, m), 7.73 (1H, d, J=8.8 Hz), 8.10 (1H, d, J=8.8 Hz), 8.17 (1H, s), 8.91 (1H, s), 9.55 (1H, br).

EXAMPLE 103

2-Chloro-4-[N-(2-hydroxyethyl)-(3,4-methylenedioxybenzyl)amino]-6,7,8-trimethoxyquinazoline

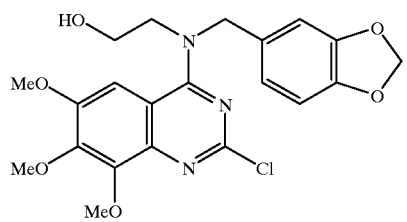

molecular formula; $C_{21}H_{22}N_3O_6Cl$; yield(%); 55; Mass; 448 (M+H)$^+$; NMR δ (CDCl$_3$); 3.38 (3H, s), 3.88 (2H, t, J=4.4 Hz), 4.01 (2H, t, J=4.4 Hz), 4.03 (3H, s), 4.07 (3H, s), 4.92 (2H, s), 6.01 (2H, s), 6.88~6.91 (3H, m), 7.00 (1H, s).

EXAMPLE 104

2-Formyl-4-(3,4-methylenedioxybenzyl)amino-6-chloroquinazoline

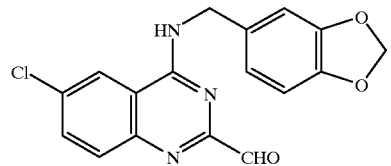

0.50 g (0.0013 mol) of 2-ethoxycarbonyl-4-(3,4-methylenedioxybenzyl)amino-6-chloroquinazoline was dissolved in a solvent mixture comprising 20 ml of methylene chloride and 20 ml of tetrahydrofuran, 2.6 ml of a 1.0 M solution of diisobutylaluminum hydride in toluene was dropped into the solution prepared above at −78° C. under stirring. The obtained mixture was stirred at −78° C. for several hours, followed by the addition of 20 ml of methanol. The obtained mixture was distilled under a reduced pressure to remove the solvent. The residue was purified by silica gel column chromatography and recrystallized from ethyl acetate/n-hexane to give 0.23 g of the title compound as a pale-yellow crystal.

yield(%); 52; m.p.(° C.); 200~202 (dec.); Mass; 342 (M+1)$^+$; NMR δ (CDCl$_3$); 4.86 (2H, d, J=5.2 Hz), 5.98 (2H, s), 6.81 (1H, d, J=7.6 Hz), 6.90 (1H, d, J=7.6 Hz), 6.92 (1H, s), 7.72 (1H, d, J=2.0 Hz), 7.77 (1H, dd, J=8.8 Hz, 2.0 Hz), 8.01 (1H, d. J=8.8 Hz), 10.05 (1H, s).

EXAMPLE 105

2-Ethoxycarbonyl-4-(3,4-methylenedioxybenzyl)amino-6-chloroquinazoline

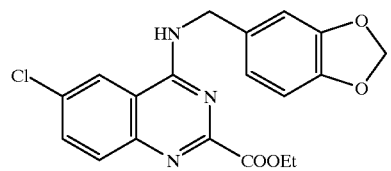

2.72 g (0.0100 mol) of 2-ethoxycarbonyl-4,6-dichloroquinazoline, 1.75 g (0.0116 mol) of piperonylamine and 1.60 g (0.0151 mol) of sodium carbonate were mixed with 100 ml of isopropyl alcohol. The obtained mixture was heated under reflux for 24 hours and distilled under a reduced pressure to remove the solvent. The residue was purified by silica gel column chromatography and recrystallized from chloroform/n-hexane to give 3.56 g of the title compound as a colorless needle.

molecular formula; $C_{19}H_{16}N_3O_4Cl$; yield(%); 92; m.p.(° C.); 212~213; Mass; 386 (M+H)$^+$; NMR δ (CDCl$_3$); 1.49 (3H, t, J=7.2 Hz), 1.54 (2H, q, J=7.2 Hz), 4.83 (2H, d, J=5.6 Hz), 5.96 (1H brs), 5.97 (2H, s), 6.80 (1H, d, J=8.0 Hz), 6.91 (1H, dd, J=8.0 Hz, 1.6 Hz), 6.97 (1H, d, J=1.6 Hz), 7.70 (1H, d, J=2.0 Hz), 7.72 (1H, dd, J=8.8 Hz, 2.0 Hz), 8.00 (1H, d, J=8.8 Hz).

EXAMPLES 106 TO 109

The following compounds were prepared in a similar manner to that of Examples 104 or 105.

EXAMPLE 106

2-Ethoxycarbonyl-4-(3-chloro-4-methoxybenzyl)
amino-6-chloroquinazoline

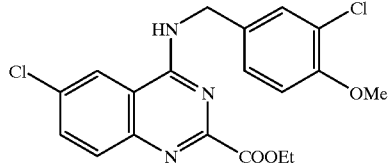

molecular formula; C$_{19}$H$_{17}$N$_3$O$_3$Cl$_2$; yield(%); 88; m.p.(° C.); 185~186; Mass; 406 (M+1)$^+$; NMR δ (CDCl$_3$); 1.49 (3H, t, J=7.2 Hz), 3.90 (3H, s), 4.54 (2H, q, J=7.2 Hz), 4.84 (2H, d, J=5.2 Hz), 6.09 (1H, brs), 6.90 (1H, d, J=8.4 Hz), 7.33 (1H, dd, J=8.4 Hz, 2.4 Hz), 7.48 (1H, d, J=2.4 Hz), 7.72 (1H, dd, J=8.8 Hz, 2.4 Hz), 7.74 (1H, d, J=2.4 Hz), 7.99 (1H, d, J=8.8 Hz).

EXAMPLE 107

2-Ethoxycarbonyl-4-(3,4-methylenedioxybenzyl)
amino-6,7,8-trimethoxyquinazoline

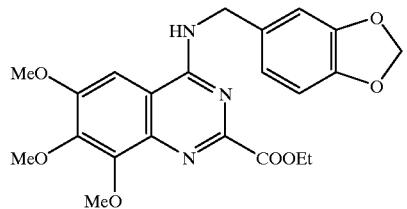

molecular formula; C$_{22}$H$_{23}$N$_3$O$_7$; yield(%); quantitative; m.p.(° C.); 163~165 (dec.); Mass; 442 (M+1)$^+$; NMR δ (CDCl$_3$); 1.45 (3H, t, J=7.2 Hz), 3.94 (3H, s), 4.02 (3H, s), 4.18 (3H, s), 4.46 (2H, q.

J=7.2 Hz), 4.80 (2H, d, J=5.2 Hz), 5.89 (1H, brt, J=5.2 Hz), 5.94 (2h, s), 6.74 (1H, d, J=7.6 Hz), 6.76 (1H, s), 6.86 (1H, dd, J=7.6 Hz, 1.6 Hz), 6.94 (1H, d, J=1.6 Hz).

EXAMPLE 108

2-Ethoxycarbonyl-4-(3-chloro-4-methoxybenzyl)
amino-6-methoxyguinazoline

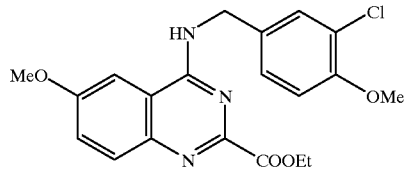

molecular formula; C$_{20}$H$_{20}$N$_3$O$_4$Cl; yield(%); 73; m.p.(° C.); 192~193; Mass; 402 (M+1)$^+$; NMR δ (CDCl$_3$); 1.49 (3H, t, J=7.2 Hz), 3.90 (3H, s), 3.91 (3H, s), 4.53 (2H, q, J=7.2 Hz), 4.86 (2H, d, J=5.6 Hz), 5.90 (1H, brt, J=5.6 Hz), 6.90 (1H, d, J=8.4 Hz), 6.96 (1H, d, J=2.4 Hz), 7.36 (1H, dd, J=8.4 Hz, 2.4 Hz), 7.44 (1H, dd, J=9.2 Hz, 2.4 Hz), 7.49 (1H, d, J=2.4 Hz), 8.00 (1H, d, J=9.2 Hz).

EXAMPLE 109

2-Ethoxycarbonyl-4-(benzimidazol-5-ylmethyl)
amino-6-methoxyquinazoline

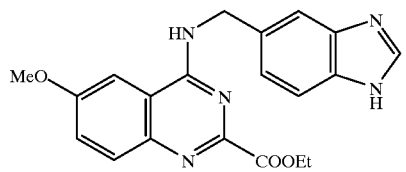

molecular formula; C$_{20}$H$_{19}$N$_5$O$_3$; yield(%); 48; m.p.(° C.); 244~245 (dec.); Mass; 378 (M+1)$^+$; NMR δ (DMSO-d$_6$); 1.35 (3H, t, J=7.2 Hz), 3.90 (3H, s), 4.33 (2H, q, J=7.2 Hz), 4.94 (2H, d, J=6.0 Hz), 7.31 (1H, d, J=8.0 Hz), 7.47 (1H, dd, J=8.8 Hz, 2.8 Hz), 7.53 (1H, d, J=8.0 Hz), 7.65 (1H, brs), 7.77 (1H, d, J=8.8 Hz), 7.78 (1H, s), 8.17 (1H, s), 8.89 (1H, brt, J=6.0 Hz).

EXAMPLE 110

(E)-2-(2-Ethoxycarbonyl-1-propenyl)-4-(3,4-
methylenedioxybenzyl)amino-6-chloroquinazoline

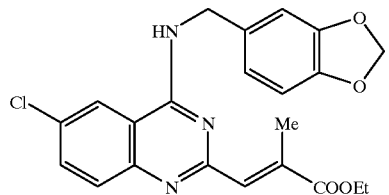

0.52 g (0.013 mol) of sodium hydride was added to a solution of 4.00 g (0.0117 mol) of 2-formyl-4-(3,4-methylene dioxybenzyl)amino-6-chloroquinazoline in 250 ml of tetrahydrofuran. 2.8 ml (0.013 mol) of triethyl 2-phosphonopropionate was dropped into the mixture prepared above under stirring and cooling with ice. The mixture thus prepared was stirred under cooling with ice for a while, heated to room temperature and stirred for additional one hour, followed by the addition of 1.5 ml of 8M hydrochloric acid/ethanol. The obtained mixture was passed through a small amount of silica gel and distilled under a reduced pressure to remove the solvent. The residue was purified by silica gel column chromatography (ethyl acetate/n-hexane) and recrystallized from chloroform/n-hexane to give 2.00 g of the title compound.

molecular formula; C$_{22}$H$_{20}$N$_3$O$_4$Cl; yield(%); 40; m.p.(° C.); 179~180 (dec.); Mass; 426 (M+1)$^+$; NMR δ (CDCl$_3$); 1.35 (3H, t, J=7.2 Hz), 2.50 (3H, d, J=1.6 Hz), 4.29 (2H, q, J=7.2 Hz), 4.78 (2H, d, J=5.2 Hz), 5.77 (1H, brt, J=5.2 Hz), 5.97 (2H, s), 6.81 (1H,. d, J=8.0 Hz), 6.87 (1H, dd, J=8.0 Hz, 1.6 Hz), 6.89 (1H, d, J=1.6 Hz), 7.62 (1H, q, J=1.6 Hz), 7.64 (1H, d, J=2.0 Hz), 7.68 (1H, dd, J=8.8 Hz, 2.0 Hz), 7.81 (1H, d, J=8.8 Hz).

EXAMPLES 111 TO 117

The following compounds were prepared in a similar manner to that of Example 110.

EXAMPLE 111

(Z)-2-(2-Ethoxycarbonyl-1-propenyl)-4-(3,4-methylenedioxybenzyl)amino-6-chloroquinazoline

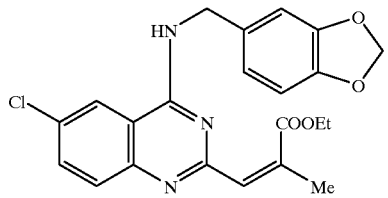

molecular formula; $C_{22}H_{20}N_3O_4Cl$; yield(%); 13; amt. of product(g); 0.64; m.p.(° C.); 162~164 (dec.); Mass; 426 (M+1)⁺; NMR δ (CDCl₃); 1.20 (3H, t, J=7.2 Hz), 2.17 (3H, d, J=1.6 Hz), 4.21 (2H, q, J=7.2 Hz), 4.70 (2H, d, J=4.8 Hz), 5.64 (1H, brs), 5.97 (2H, s), 6.53 (1H, q, J=1.6 Hz), 6.81 (1H, d, J=7.6 Hz), 6.85 (1H, dd, J=7.6 Hz, 1.6 Hz), 6.87 (1H, d, J=1.6 Hz), 7.58 (1H, d, J=2.4 Hz), 7.62 (1H, dd, J=8.8 Hz, 2.4 Hz), 7.71 (1H, d, J=8.8 Hz).

EXAMPLE 112

(E)-2-(2-Ethoxycarbonylvinyl)-4-(3,4-methylenedioxybenzyl)amino-6-chloroquinazoline

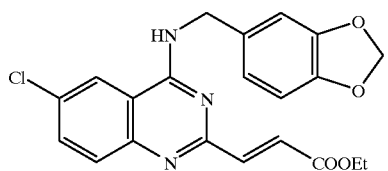

molecular formula; $C_{21}H_{18}N_3O_4Cl$; yield(%); 67; m.p.(° C.); 195~196; Mass; 412 (M+1)⁺; NMR δ (CDCl₃); 1.35 (3H, t, J=7.2 Hz), 4.29 (2H, q, J=7.2 Hz), 4.80 (2H, d, J=5.2 Hz), 5.77 (1H, brs), 5.97 (2H, s), 6.81 (1H, d, J=7.6 Hz), 6.89 (1H, d, J=7.6 Hz), 6.90 (1H, s), 7.21 (1H, d, J=15.6 Hz), 7.64 (1H, d, J=2.0 Hz), 7.66 (1H, d, J=15.6 Hz), 7.68 (1H, dd, J=9.2 Hz, 2.0 Hz), 7.82 (1H d, J=9.2 Hz).

EXAMPLE 113

(E)-2-(2-Ethoxycarbonylvinyl)-4-(3-chloro-4-methoxybenzyl)amino-6-chloroquinazoline

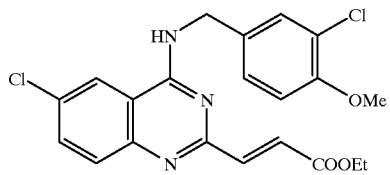

molecular formula; $C_{21}H_{19}N_3O_4Cl_2$; yield(%); 74; m.p.(° C.); 211~212; Mass; 432 (M+1)⁺; NMR δ (CDCl₃); 1.35 (3H, t, J=7.2 Hz), 3.89 (3H, s), 4.28 (2H, q, J=7.2 Hz), 4.79 (2H, d, J=5.6 Hz), 6.91 (1H, d, J=8.4 Hz), 7.16 (1H, d, J=15.6 Hz), 7.33 (1H, dd, J=8.4 Hz, 2.0 Hz), 7.46 (1H, d, J=2.0 Hz), 7.62 (1H, d, J=15.6 Hz), 7.64 (1H, dd, J=8.8 Hz, 2.4 Hz), 7.75 (1H, d, J=8.8 Hz), 7.77 (1H, brs), 8.16 (1H, d, J=2.4 Hz).

EXAMPLE 114

(E)-2-(2-Ethoxycarbonyl-1-propenyl)-4-(3-chloro-4-methoxybenzyl)amino-6-chloroquinazoline

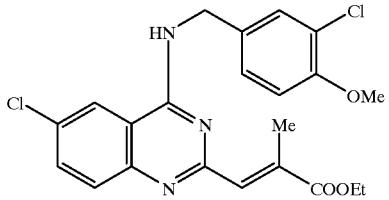

molecular formula; $C_{22}H_{21}N_3O_3Cl_2$; yield(%); 54; m.p.(° C.); 154~155; Mass; 446 (M+1)⁺; NMR δ (CDCl₃); 1.35 (3H, t, J=7.2 Hz), 2.48 (3H, d, J=1.6 Hz), 3.91 (3H, s), 4.29 (2H, q, J=7.2 Hz), 4.80 (2H, d, J=5.2 Hz), 5.82 (1H, brt, J=5.2 Hz), 6.92 (1H, d, J=8.8 Hz), 7.27 (1H, dd, J=8.8 Hz, 2.0 Hz), 7.42 (1H, d, J=2.0 Hz), 7.6.2 (1H, q, J=1.6 Hz), 7.67 (1H, d, J=2.4 Hz), 7.69 (1H, dd, J=8.8 Hz, 2.4 Hz), 7.82 (1H, d, J=8.8 Hz).

EXAMPLE 115

(Z)-2-(2-Ethoxycarbonyl-1propenyl)-4-(3-chloro-4-methoxybenzyl)amino-6-chloroquinazoline

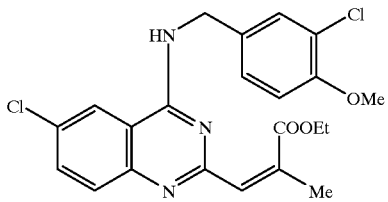

molecular formula; $C_{22}H_{21}N_3O_4Cl_2$; yield(%); 11; m.p.(° C.); 141~142; Mass; 446 (M+1⁺ NMR δ (CDCl₃); 1.19 (3H, t, J=7.2 Hz), 2.17 (3H, d, J=1.6 Hz), 3.91 (3H, s), 4.19 (2H, q, J=7.2 Hz), 4.73 (2H, d, J=5.2 Hz), 5.69 (1H, brt, J=5.2 Hz), 6.53 (1H, q, J=1.6 Hz), 6.92 (1H, d, J=8.4 Hz), 7.26 (1H, dd, J=8.4 Hz, 2.0 Hz), 7.40 (1H, d, J=2.0 Hz), 7.60 (1H, d, J=2.0 Hz), 7.63 (1H, dd, J=8.8 Hz, 2.0 Hz), 7.71 (1H, d, J=8.8 Hz).

EXAMPLE 116

(E)-2-(2-Ethoxycarbonyl-1-propenyl)-4-(3,4-methylenedioxybenzyl)amino-6,7,8-tribethoxyquinazoline

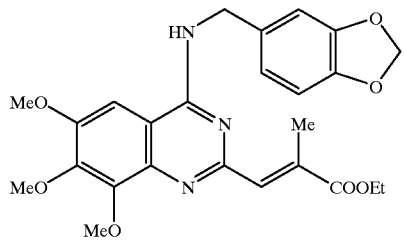

molecular formula; $C_{25}H_{27}N_3O_7$; yield(%); 51; m.p.(° C.); 175~176; Mass; 482 (M+1)⁺; NMR δ (CDCl₃); 1.35 (3H, t, J=7.2 Hz), 2.52 (3H, d, J=1.6 Hz), 3.95 (3H, s), 4.04

(3H, s), 4.14 (3H, s), 4.28 (2H, q, J=7.2 Hz), 4.80 (2H, d, J=5.2 Hz), 5.60 (1H, brt, J=5.2 Hz), 5.96 (2H, s), 6.67 (1H, s), 6.80 (1H, d, J=8.0 Hz), 6.87 (1H, dd, J=8.0 Hz, 1.6 Hz), 6.90 (1H, d, J=1.6 Hz), 7.69 (1H, q, J=1.6 Hz).

EXAMPLE 117

(Z)-2-(2-Ethoxycarbonyl-1-propenyl)-4-(3,4-methylenedioxybenzyl)amino-6,7,8-trimethoxyquinazoline

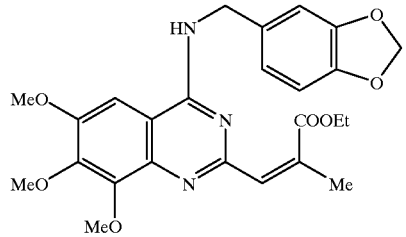

molecular formula; $C_{25}H_{27}N_3O_7$; yield(%); 11; m.p.(° C.); 157~158 (dec.); Mass; 482 (M+1)$^+$; NMR δ (CDCl$_3$); 1.19 (3H, t, J=7.2 Hz), 2.16 (3H, s), 3.92 (3H, s), 4.02 (3H, s), 4.09 (3H, s), 4.21 (2H, q, J=7.2 Hz), 4.72 (2H, d, J=5.2 Hz), 5.43 (1H, brs), 5.96 (2H, s), 6.59~6.61 (2H, m), 6.80 (1H, d, J=8.0 Hz), 6.86~6.89 (2H, m).

EXAMPLE 118

(E-2-(2-Carboxy-1propenyl)-4-(3,4-methylenedioxybenzyl)amino-6-chloroquinazoline

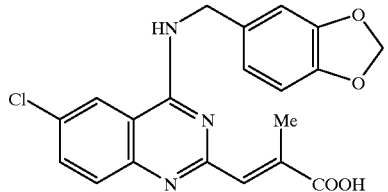

1.00 g (0.0023 mol) of (E)-2-(2-ethoxycarbonylpropenyl)-4-(3,4-methylenedioxybenzyl)amino-6-chloroquinazoline was dissolved in a mixture comprising 5 ml of tetrahydrofuran and 20 ml of ethanol, followed by the addition of 20 ml of a 1N aqueous solution of sodium hydroxide. The obtained mixture was stirred at room temperature for several hours, neutralized with 20 ml of 1N hydrochloric acid and concentrated under a reduced pressure. The crystal thus formed was recovered by filtration, washed with water and air-dried to give 0.85 g of the title compound.

molecular formula; $C_{20}H_{16}N_3O_4Cl$; yield(%); 91; m.p.(° C.); 145~146; Mass; 398 (M+1)$^+$; NMR δ (DMSO-d$_6$); 2.36 (3H, d, J=1.6 Hz), 4.70 (2H, d, J=5.6 Hz), 5.97 (2H, s), 6.85 (2H, s), 6.95 (1H, s), 7.34 (1H, q, J=1.6 Hz), 7.72 (1H, d, J=8.8 Hz), 7.79 (1H, dd, J=8.8 Hz, 2.0 Hz), 8.46 (1H, d, J=2.0 Hz), 8.86 (1H, brt, J=5.6 Hz).

EXAMPLES 119 TO 126

The following compounds were prepared in a similar manner to that of Example 118.

EXAMPLE 119

2-Carboxy-4-(3,4-methylenedioxybenzyl)amino-6-chloroquinazoline

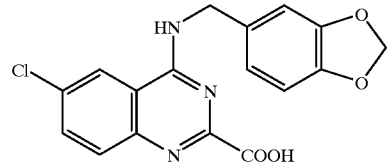

molecular formula; $C_{17}H_{12}N_3O_4Cl$; yield(%); quantitative; m.p.(° C.); 240 (dec.); Mass; 402 (M−1+2Na)$^+$; NMR δ (DMSO-d$_6$); 4.71 (2H, d, J=5.6 Hz), 5.96 (2H, s), 6.83 (1H, d, J=8.0 Hz), 6.89 (1H, dd, J=8.0 Hz, 1.2 Hz), 7.06 (1H, d, J=1.2 Hz), 7.75 (1H, dd, J=8.8 Hz, 2.4 Hz), 7.90 (1H, d, J=8.8 Hz), 8.48 (1H, d, J=2.4 Hz), 8.82 (1H, brt, J=5.6 Hz).

EXAMPLE 120

(E)-2-(2-Carboxyvinyl)-4-(3,4-methylenedioxybenzyl)amino-6-chloroquinazoline

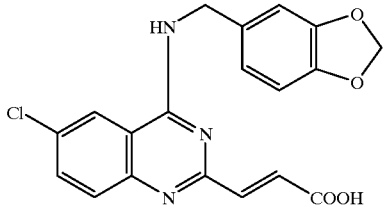

molecular formula; $C_{19}H_{14}N_3O_4Cl$; yield(%); 43; m.p.(° C.); 114~115; Mass; 428 (M−1+2Na)$^+$; NMR δ (DMSO-d$_6$); 4.71 (2H, d, J=5.6 Hz), 5.96 (2H, s), 6.84 (1H, d, J=8.0 Hz), 6.90 (1H, dd, J=8.0 Hz, 1.6 Hz), 6.99 (1H, d, J=1.6 Hz), 7.02 (1H, d, J=15.6 Hz), 7.23 (1H, d, J=15.6 Hz), 7.73 (1H, d, J=9.2 Hz), 7.78 (1H, dd, J=9.2 Hz, 2.0 Hz), 8.44 (1H, d, J=2.0 Hz), 8.89 (1H, brt, J=5.6 Hz).

EXAMPLE 121

(Z)-2-(2-carboxy-1-propenyl)-4-(3,4-methylenedioxybenzyl)amino-6-chloroquinazoline

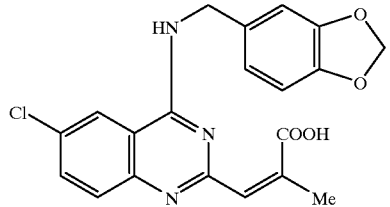

molecular formula; $C_{20}H_{16}N_3O_4Cl$; yield(%); quantitative; m.p.(° C.); 195~196; Mass; 398 (M+1)$^+$; NMR δ (DMSO-d$_6$); 2.10 (3H, d, J=1.6 Hz), 4.70 (2H, d, J=5.6 Hz), 5.97 (2H, s), 6.56 (1H, d, J=1.6 Hz), 6.86 (1H, d, J=8.0 Hz), 6.91 (1H, dd, J=8.0 Hz, 1.6 Hz), 7.00 (1H, d, J=1.6 Hz), 7.65 (1H, d, J=9.2 Hz), 7.81 (1H, dd, J=9.2 Hz, 2.4 Hz), 8.46 (1H, d, J=2.4 Hz), 8.96 (1H, brt, J=5.6 Hz).

EXAMPLE 122

(E)-2-(2-Carboxyvinyl)-4-(3-chloro-4-methoxybenzyl)amino-6-chloroquinazoline

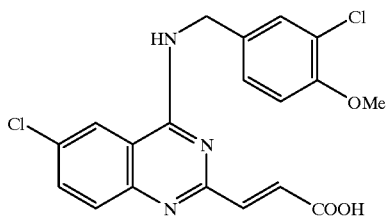

molecular formula; $C_{19}H_{15}N_3O_3Cl_2$; yield(%); quantitative; m.p.(° C.); 109~110; Mass; 448 (M−1+2Na)$^+$; NMR δ (DMSO-d$_6$); 3.81 (3H, s), 4.73 (2H, d, J=5.6 Hz), 6.95 (1H, d, J=15.6 Hz), 7.05 (1H, d, J=15.6 Hz), 7.08 (1H, d, J=8.4 Hz), 7.37 (1H, dd, J=8.4 Hz, 2.0 Hz), 7.48 (1H, d, J=2.0 Hz), 7.68 (1H, d, J=8.8 Hz), 7.73 (1H, dd, J=8.8 Hz, 2.0 Hz), 8.42 (1H, d, J=2.0 Hz), 8.91 (1H, brt, J=5.6 Hz).

EXAMPLE 123

(E)-2-(2-Carboxy-1propenyl)-4-(3-chloro-4-methoxybenzyl)amino-6-chloroquinazoline

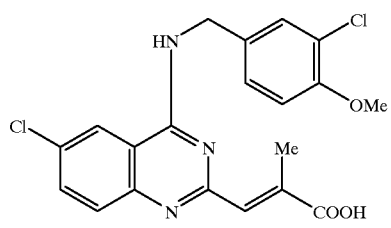

molecular formula; $C_{20}H_{17}N_3O_3Cl_2$; yield(%); quantitative; m.p.(° C.); 151~152; Mass; 462 (M−1+2Na); NMR δ (DMSO-d$_6$); 2.33 (3H, d, J=1.2 Hz), 3.82 (3H, s), 4.72 (2H, d, J=5.6 Hz), 7.09 (1H, d, J=8.4 Hz), 7.20 (1H, d, J=1.2 Hz), 7.32 (1H, dd, J=8.4 Hz, 2.0 Hz), 7.44 (1H, d, J=2.0 Hz), 7.67 (1H, d, J=8.8 Hz), 7.74 (1H, dd, J=8.8 Hz, 2.4 Hz), 8.43 (1H, d, J=2.4 Hz), 8.87 (1H, brt, J=5.6 Hz).

EXAMPLE 124

(Z)-2-(2-Carboxy-1-propenyl)-4-(3-chloro-4-methoxybenzyl)amino-6-chloroquinazoline

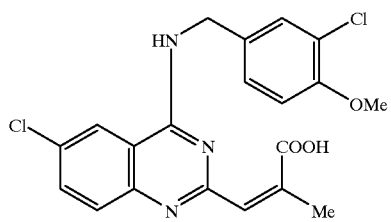

molecular formula; $C_{20}H_{17}N_3O_3Cl_2$; yield(%); quantitative; m.p.(° C.); 207~208 (dec.); Mass; 418 (M+1)$^+$; NMR δ (DMSO-d$_6$); 2.10 (3H, d, J=1.4 Hz), 3.83 (3H, s), 4.72 (2H, d, J=5.2 Hz), 6.54 (1H, d, J=1.4 Hz), 7.10 (1H, d, J=8.4 Hz), 7.38 (1H, dd, J=8.4 Hz, 2.4 Hz), 7.49 (1H, d, J=2.4 Hz), 7.65 (1H, d, J=8.8 Hz), 7.81 (1H, dd, J=8.8 Hz, 2.4 Hz), 8.44 (1H, d, J=2.4 Hz), 8.95 (1H, brt, J=5.2 Hz).

EXAMPLE 125

(E)-2-(2-Carboxy-1-propenyl)-4-(3,4-methylenedioxybenzyl)amino-6,7,8-trimethoxyquinazoline

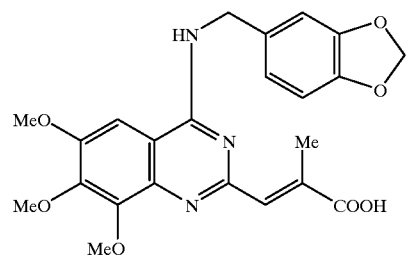

molecular formula; $C_{23}H_{23}N_3O_7$; yield(%); 91; m.p.(° C.); 200~201 (dec.); Mass; 454 (M+1)$^+$; NMR δ (DMSO-d$_6$); 2.38 (3H, s), 3.89 (3H, s), 3.92 (3H, s), 4.01 (3H, s), 4.71 (2H, d, J=5.6 Hz), 5.97 (2H, s), 6.85 (2H, s), 6.93 (1H, s), 7.37 (1H, s), 7.53 (1H, s), 8.53 (2H, brt, J=5.6 Hz), 12.55 (1H, brs).

EXAMPLE 126

(Z)-2-(2-Carboxy-1-propenyl)-4-(3,4-methylenedioxybenzyl)amino-6,7 8-trimethoxyquinazoline

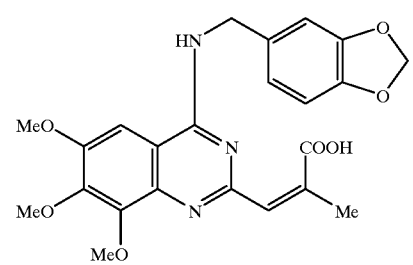

molecular formula; $C_{23}H_{23}N_3O_7$; yield(%); 90; m.p.(° C.); 237~238 (dec.); Mass; 454 (M+1)$^+$; NMR δ (DMSO-d$_6$); 2.11 (3H, d, J=1.2 Hz), 3.92 (3H, s), 3.93 (3H, s), 3.94 (3H, s), 4.76 (2H, d, J=5.6 Hz), 5.98 (2H, s), 6.8~6.9 (3H, m), 6.97 (1H, s), 7.61 (1H, s), 9.08 (1H, brt, J=5.6 Hz).

EXAMPLE 127

4-(α-Carboxy-3,4-methylenedioxybenzyl)amino-6-chloroquinazoline

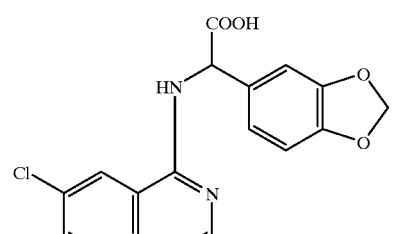

10 ml of ethanol, 5 ml of water and 20 mg of sodium hydroxide were added to 100 mg of 4-(α-ethoxycarbonyl- 3,4-methylenedioxybenzyl)amino- 6-chloroquinazoline. The obtained mixture was refluxed for 10 minutes and concentrated under a reduced pressure, followed by the addition of 20 ml of water. The obtained mixture was neutralized with 1N hydrochloric acid. The crystal thus precipitated was recovered by filtration. Thus, 45 mg of the title compound was obtained.

molecular formula; $C_{17}H_{12}N_3O_4Cl$; yield(%); 49; m.p.(° C.); 235~236; Mass; 358 (M+1); NMR δ (DMSO-$d_6$); 5.75 (1H, d, J=6.4 Hz), 6.01 (2H, s), 6.89 (1H, d, J=8.0 Hz), 7.00 (1H, d, J=8.0 Hz), 7.08 (1H, s), 7.70 (1H, d, J=8.8 Hz), 7.75 (1H, dd, J=1.6 Hz, 8.8 Hz), 8.49 (1H, s), 8.59 (1H, d, J=6.4 Hz), 8.70 (1H, d, J=1.6 Hz).

EXAMPLES 128 TO 129

The following compounds were prepared in a similar manner to that of Example 127.

EXAMPLE 128

4-[N-(Carboxymethyl)-3(3,4-methylenedioxybenzyl) amino]-6,7,8-trimethoxyquinazoline

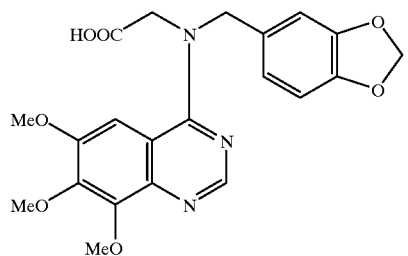

molecular formula; $C_{21}H_{21}N_3O_7$; yield(%); 90; m.p.(° C.); 134~136; Mass; 428 (M+H)$^+$; NMR δ (CDCl$_3$); 3.43 (3H, s), 4.06 (3H, s), 4.17 (3H, s), 4.62 (2H, s), 5.16 (2H, s) 6.03 (2H, s), 6.87 (1H, s), 6.91 (2H, s), 7.06 (1H, s), 8.87 (1H, s).

EXAMPLE 129

4-(3,4-Methylenedioxybenzyl)amino-6-carboxyquinazoline

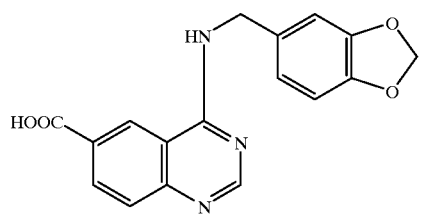

molecular formula; $C_{17}H_{13}N_3O_4$; yield(%); 98; m.p.(° C.); 247~248 (dec.); Mass; 324 (M+H)$^+$; NMR δ (DMSO-$d_6$); 4.86 (2H, d, J=5.6 Hz), 5.99 (2H, s), 6.89 (1H, d, J=8.0 Hz), 6.92 (1H, d, J=8.0 Hz), 7.02 (1H, s), 7.92 (1H, d, J=8.8 Hz), 8.46 (1H, d, J=8.8 Hz), 8.96 (1H, s), 9.20 (1H, s), 10.88 (1H, brs).

EXAMPLE 130

4-(α-Carbamoyl-3,4-methylenedioxybenzyl)amino-6-chloroquinazoline

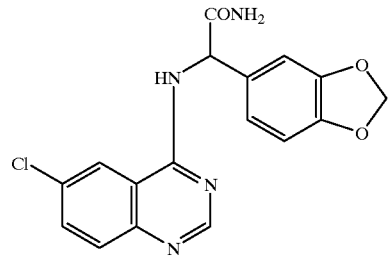

20 ml of a 10% solution of ammonia in ethanol was added to 200 mg of 4-(α-ethoxycarbonyl-3,4-methylenedioxybenzyl)amino-6-chloroquinazoline. The obtained mixture was stirred at room temperature for 3 days. The crystal thus precipitated was recovered by filtration. Thus, 60 mg of the title compounds was obtained.

molecular formula; $C_{17}H_{13}N_4O_3Cl$; yield(%); 32; m.p.(° C.); 230~231; Mass m/e; 357 (M+1); NMR δ (CDCl$_3$+ DMSO-$d_6$); 5.96 (3H, m), 6.42 (1H, brs), 6.79 (1H, d, J=8.0 Hz), 7.09 (1H, dd, J=8.0 Hz, 1.6 Hz), 7.14 (1H, d, J=1.6 Hz), 7.15 (1H, brs), 7.67 (1H, dd, J=8.8 Hz, 2.0 Hz), 7.75 (1H, d, J=8.8 Hz), 8.28 (1H, d, J=2.0 Hz), 8.57 (1H, s).

EXAMPLES 131

The following compound was prepared in a similar manner to that of Example 130.

EXAMPLE 131

4-(3 4-Methylenedioxybenzyl)amino-6-carbamoylquinazoline

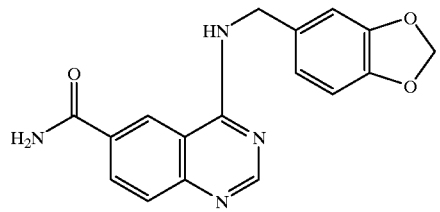

molecular formula; $C_{17}H_{14}N_4O_3$; Mass; 323 (M+H)$^+$; NMR δ (DMSO-$d_6$); 4.68 (2H, d, J=6.0 Hz), 5.97 (2H, s), 6.85 (1H, d, J=8.0 Hz), 6.88 (1H, d, J=8.0 Hz), 6.97 (1H, s), 7.55 (1H, brs), 7.70 (1H, d, J=8.4 Hz), 7.97 (1H, brs), 8.18 (1H, dd. J=8.4 Hz, 1.6 Hz), 8.50 (1H, s), 8.84 (1H, d, J=1.6 Hz), 8.92 (1H, brt, J=6.0 Hz).

EXAMPLE 132

4-(α-Hydroxymethyl-3,4-methylenedioxybenzyl)amino-6-chloroquinazoline

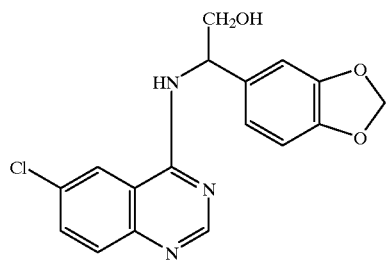

10 ml of ethanol and 197 mg of sodium borohydride were added to 200 mg of 4-(α-ethoxycarbonyl-3,4-methylenedioxybenzyl)amino-6-chloroquinazoline. The obtained mixture was refluxed for 30 minutes, followed by the addition of 5 ml of water. The obtained mixture was concentrated under a reduced pressure, followed by the addition of 10 ml of water. The crystal thus precipitated was recovered by filtration. Thus, 30 mg of the title compound was obtained.

molecular formula; $C_{17}H_{14}N_3O_3Cl$; yield(%); 17; m.p.(° C.); 204~205; Mass m/e; 344 (M+1); NMR δ (CDCl$_3$(+DMSO-d$_6$)); 3.95 (2H, m), 5.43 (1H, q, J=4.4 Hz), 5.92 (1H, d, J=1.6 Hz), 5.93 (1H, d, J=1.6 Hz), 6.76 (1H, d, J=8.0 Hz), 6.90 (1H, dd, J=8.0 Hz, 1.6 Hz), 6.95 (1H, d, J=1.6 Hz), 7.60 (1H, brs), 7.65 (1H, dd, J=8.4 Hz, 2.4 Hz), 7.74 (1H, d, J=8.4 Hz), 8.31 (1H, d, J=2.4 Hz), 8.53 (1H, s).

EXAMPLE 133

4-[(3,4-Methylenedioxybenzyl)]amino-6-hydroxymethylquinazoline

The title compound was prepared in a similar manner to that of Example 135.

molecular formula; $C_{17}H_{15}N_3O_3$; yield(%); 34; m.p.(° C.); 176~177; Mass m/e; 310 (M+1); NMR δ (DMSO-d$_6$); 4.62 (2H, d, J=5.6 Hz), 4.65 (2H, d, J=5.6 Hz), 5.36 (1H, t, J=5.6 Hz), 5.94 (2H, s), 6.82 (1H, s), 6.82 (1H, s), 6.92 (1H, s), 7.63 (1H, d, J=8.4 Hz), 7.70 (1H, d, J=8.4 Hz), 8.20 (1H, s), 8.41 (1H, s), 8.74 (1H, t, J=5.6 Hz).

EXAMPLE 134

4-(3,4-Methylenedioxybenzyl)amino-6-methylsulfinylquinazoline

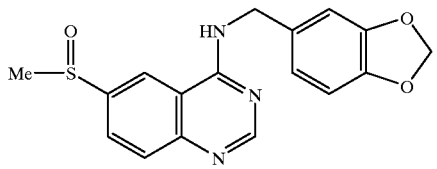

A solution of 1.20 g (6.95 mmol) of m-chloroperbenzoic acid in 30 ml of chloroform was dropped into a solution of 1.80 g (5.53 mmol) of 4-(3,4-methylenedioxybenzyl)amino-6-methylthioquinazoline in 100 ml of chloroform under cooling with ice and stirring. The obtained mixture was stirred under cooling with ice for several hours, washed with a saturated aqueous solution of sodium hydrogencarbonate, dried over anhydrous magnesium sulfate and filtered. The filtrate was purified by silica gel column chromatography (ethyl acetate/acetone) and recrystallized from chloroform/n-hexane to give 1.51 g of the title compound as a pale-yellow crystal.

molecular formula; $C_{17}H_{15}N_3O_3S$; yield(%); 80; m.p.(° C.); 154~155; Mass; 342 (M+H)$^+$; NMR δ (CDCl$_3$); 2.75 (3H, s), 4.80 (2H, d, J=5.2 Hz), 5.96 (2H, s), 6.80 (1H, d, J=8.0 Hz), 6.89 (1H, d, J=8.0 Hz), 6.91 (1H, s), 7.06 (1H, brs), 7.64 (1H, d, J=8.8 Hz), 7.98 (1H, d, J=8.8 Hz), 8.43 (1H, s), 8.74 (1H, s).

EXAMPLE 135

4-(3,4-Methylenedioxybenzyl)amino-6-methylsulfonylquinazoline

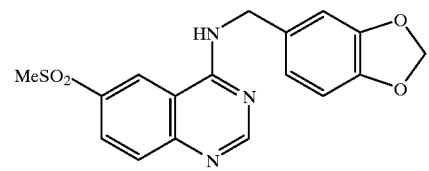

A solution of 0.65 g (3.8 mmol) of m-chloroperbenzoic acid in 20 ml of chloroform was dropped into a solution of 1.00 g (2.93 mmol) of the 4-(3,4-methylenedioxybenzyl)amino-6-methylsulfinylquinazoline prepared in Example 137 under stirring at room temperature. The obtained mixture was stirred at room temperature for several hours, washed with a saturated aqueous solution of sodium hydrogencarbonate, dried over anhydrous magnesium sulfate and filtered. The filtrate was purified by silica gel column chromatography (ethyl acetate) and recrystallized from chloroform/n-hexane to give 0.85 g of the title compound as a yellow crystal.

molecular formula; $C_{17}H_{15}N_3O_4S$; yield(%); 81; m.p.(° C.); 192~193; Mass; 358 (M+H)$^+$; NMR δ (CDCl$_3$); 3.13 (3H, s), 4.80 (2H, d, J=5.2 Hz), 5.95 (2H, s), 6.79 (1H, d, J=8.0 Hz), 6.91 (1H, d, J=8.0 Hz), 6.95 (1H, s), 8.05 (1H, d, J=8.8 Hz), 8.17 (1H, d, J=8.8 Hz), 8.72 (1H, s), 8.81 (1H, brs), 8.98 (1H, s).

EXAMPLE 136

2-Hydroxymethyl-4-(3,4-methylenedioxybenzyl)amino-6-methoxyquinazoline

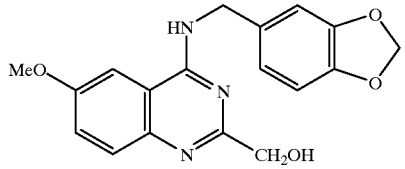

1.5 g of 10% palladium/carbon powder was added to a solution of 1.26 g (2.93 mmol) of 2-benzyloxymethyl-4-(3,4-methylenedioxybenzyl)amino-6-methoxyquinazoline in an ethyl acetate/ethanol (20 ml—20 ml) mixture. The obtained mixture was stirred at room temperature in a stream of hydrogen for 24 hours and filtered through Celite. The filter cake was washed with hot ethyl acetate/ethanol. The filtrate and the washings were distilled under a reduced pressure to remove the solvent. Thus 0.89 g of the title compound was obtained as a pale-yellow crystal.

molecular formula; $C_{18}H_{17}N_3O_4$; yield(%); 89; m.p.(° C.); 216~218; Mass; 340 (M+H)$^+$; NMR δ (CDCl$_3$); 3.91 (3H, s), 4.15 (1H, brs), 4.68 (2H, brs), 4.77 (2H, d, J=5.6 Hz), 5.95 (2H, s), 6.79 (1H, d, 7.6 Hz), 6.85 (1H, brs), 6.88 (1H, dd, J=7.6 Hz, 1.6 Hz), 6.92 (1H, d, J=1.6 Hz), 7.21 (1H, d, J=2.8 Hz), 7.37 (1H, dd, J=9.2 Hz, 2.8 Hz), 7.72 (1H, d, J=9.2 Hz).

EXAMPLE 137

2-Hydroxy-4-(3,4-methylenedioxybenzyl)amino-6-methoxyquinazoline

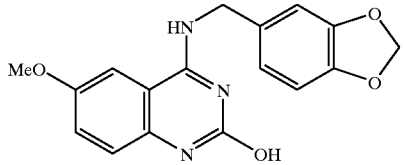

The title compound was prepared in a similar manner to that of Example 136.

molecular formula; $C_{17}H_{15}N_3O_4$; yield(%); 16; m.p.(° C.); 215~217 (dec.); Mass; 326 (M+H)$^+$; NMR δ (DMSO-d$_6$); 3.79 (3H, s), 4.62 (2H, d, J=5.6 Hz), 5.98 (2H, s), 6.84~6.87 (2H, m), 6.94 (1H, s), 7.09 (1H, d, J=8.8 Hz), 7.22 (1H, dd, J=8.8 Hz, 2.8 Hz), 7.60 (1H, d, J=2.8 Hz), 8.65 (1H, brt, J=5.6 Hz), 10.55 (1H, s).

EXAMPLE 138

2-Formyl-4-(3,4-methylenedioxybenzyl)amino-6-methoxyquinazoline

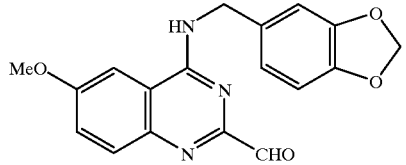

A solution of 1.5 ml of dimethyl sulfoxide in 5 ml of methylene chloride was dropped into a solution of 1.0 ml (11 mmol) of oxalyl chloride in 10 ml of methylene chloride under stirring at −78° C. The obtained mixture was stirred at −78° C. for 15 minutes, followed by the dropwise addition of a solution of 0.74 g (2.2 mmol) of 2-hydroxymethyl-4-(3,4-methylenedioxybenzyl)amino-6-methoxyquinazoline in 7 ml of dimethyl sulfoxide. After the mixture thus obtained had been stirred at −78° C. for 20 minutes, 5 ml of triethylamine was dropped into the resulting mixture. The mixture thus prepared was stirred for 30 minutes, while raising the temperature to room temperature. Water was added to the reaction mixture and the resulting mixture was extracted with chloroform. The organic layer was dried over anhydrous magnesium sulfate and filtered. The filtrate was distilled under a reduced pressure to remove the solvent. Thus, 0.74 g of the title compound was obtained as a crude brown oil.

molecular formula; $C_{18}H_{15}N_3O_4$; yield(%); quantitative; NMR δ (CDCl$_3$); 3.93 (3H, s), 4.86 (2H, d, J=5.6 Hz), 5.95 (2H, s), 6.28 (1H, brs), 6.78 (1H, d, J=8.0 Hz), 6.89 (1H, dd, J=8.0 Hz, 1.6 Hz), 6.92 (1H, d, J=1.6 Hz), 7.09 (1H, d, J=2.8 Hz), 7.47 (1H, dd, J=9.2 Hz, 2.8 Hz), 7.97 (1H, d, J=9.2 Hz), 10.02 (1H, s).

EXAMPLE 139

2-Carboxy-4-(3,4-methylenedioxybenzyl)amino-6-methoxyquinazoline

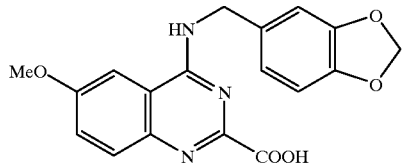

1.00 g of silver (I) oxide and 15 ml of a 1N aqueous solution of sodium hydroxide were added to a solution of 0.59 g (1.8 mmol) of the 2-formyl-4-(3,4-methylenedioxybenzyl)amino-6-methoxyquinazoline prepared in Example 141 in 20 ml of 1,4-dioxane. The obtained mixture was stirred at 60° C. After 30 minutes, the reaction mixture was filtered through Celite and the filter cake was washed with a small amount of dioxane and water. The filtrate and washings were neutralized with 1N hydrochloric acid and extracted with chloroform/ethanol. The organic layer was dried over anhydrous magnesium sulfate and filtered. The filtrate was distilled under a reduced pressure to remove the solvent. The crystal thus formed was recovered by filtration and washed with chloroform to give 0.34 g of the title compound as a pale-yellow crystal.

molecular formula; $C_{18}H_{15}N_3O_5$; yield(%); 55; m.p.(° C.); 190~191 (dec.); Mass; 354 (M+H)⁺; NMR δ (DMSO-d₆); 3.90 (3H, s), 4.77 (2H, d, J=5.6 Hz), 5.97 (2H, s), 6.86 (1H, d, J=8.0 Hz), 6.92 (1H, d, J=8.0 Hz), 7.05 (1H, s), 7.49 (1H, dd, J=9.2 Hz, 2.8 Hz), 7.76 (1H, d, J=2.8 Hz), 7.79 (1H, d, J=9.2 Hz), 8.91 (1H, brt, J=5.6 Hz).

EXAMPLES 140 TO 142

The following compounds were prepared in a similar manner to that of Example 138 or 139.

EXAMPLE 140

4-(3-Formylbenzyl)amino-6,7,8-trimethoxyquinazoline

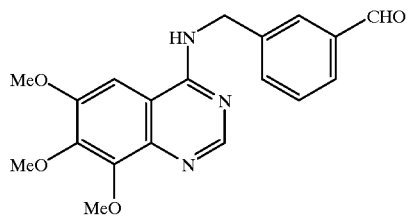

molecular formula; $C_{19}H_{19}N_3O_4$; yield(%); quantitative; m.p.(° C.); oily substance; NMR δ (CDCl₃); 3.96 (3H, s), 4.04 (3H, s), 4.13 (3H, s), 4.97 (2H, d, J=5.6 Hz), 5.97 (1H, brt, J=5.6 Hz), 6.76 (1H, s), 7.53 (1H, t, J=7.6 Hz), 7.70 (1H, d, J=7.6 Hz), 7.81 (1H, d, J=7.6 Hz), 7.91 (1H, s), 8.64 (1H, s), 10.00 (1H, s).

EXAMPLE 141

4-(3-Carboxybenzyl)amino-6,7,8-trimethoxyquinazoline

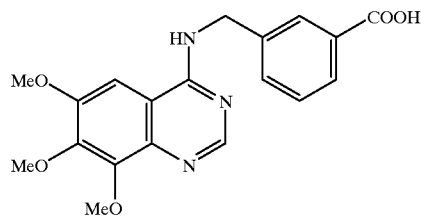

molecular formula; $C_{19}H_{19}N_3O_5$; yield(%); 45; m.p.(° C.); 245~246 (dec.); Mass; 370 (M+H)⁺; NMR δ (DMSO-d₆); 3.89 (3H, s), 3.93 (3H, s), 3.98 (3H, s), 4.86 (2H, d, J=5.6 Hz), 7.46 (1H, d, J=7.6 Hz), 7.56 (1H, s), 7.62 (1H, d, J=7.6 Hz), 7.83 (1H, d, J=7.6 Hz), 7.95 (1H, s), 8.39 (1H, s), 8.83 (1H, brs).

EXAMPLE 142

4-(4-Acetylbenzyl)amino-6-methoxyquinazoline

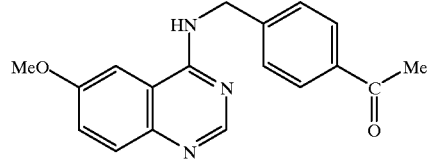

molecular formula; $C_{18}H_{17}N_3O_2$; yield(%); 41; m.p.(° C.); 204~206; Mass; 308 (M+H)⁺; NMR δ (CDCl₃); 2.60 (3H, s), 3.91 (3H, s), 4.97 (2H, d, J=5.6 Hz), 5.96 (1H, brs), 6.98 (1H, s), 7.42 (1H, d, J=9.2 Hz), 7.50 (2H, d, J=8.0 Hz), 7.82 (1H, d, J=9.2 Hz), 7.94 (2H, d, J=8.0 Hz), 8.61 (1H, s).

EXAMPLE 143

2-Hydroxyiminomethyl-4-(3,4-methylenedioxybenzyl)amino-6-chloroquinazoline

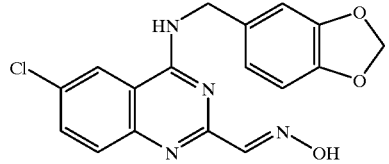

0.60 g of hydroxylamine hydrochloride and 3.0 ml of a 1N aqueous solution of sodium hydroxide were added to a solution of 1.00 g (2.93 mmol) of 2-formyl-4-(3,4-methylenedioxybenzyl)amino-6-cloroquinazoline in 30 ml of ethanol. The obtained mixture was stirred at 60° C. for 30 minutes and cooled by allowing to stand. The crystal thus precipitated was recovered by filtration, washed with ethanol and n-hexane and air-dried to give 1.00 g of the title compound as a white crystal.

molecular formula; $C_{17}H_{13}N_4O_3Cl$; yield(%); 96; m.p.(° C.); 245~246 (dec.); Mass; 357 (M+1); NMR δ (DMSO-d₆); 4.69 (2H, d, J=6.0 Hz), 5.96 (2H, s), 6.84 (1H, d, J=7.6 Hz), 6.91 (1H, d, J=7.6 Hz, 1.6 Hz), 7.05 (1H, d, J=1.6 Hz), 7.72 (1H, d, J=8.8 Hz), 7.78 (1H, dd, J=8.8 Hz, 2.0 Hz), 7.96 (1H, s), 8.45 (1H, d, J=2.0 Hz), 8.91 (1H, brt, J=6.0 Hz), 11.83 (1H, s).

EXAMPLES 144 TO 146

The following compounds were prepared in a similar manner to that of Example 143.

EXAMPLE 144

2-Hydroxyiminomethyl-4-(3,4-methylenedioxybenzyl)amino-6-methoxyquinazoline

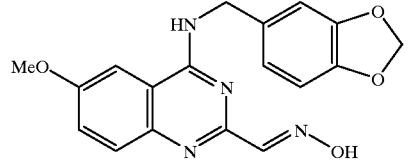

molecular formula; $C_{18}H_{16}N_4O_4$; yield(%); 46; m.p.(° C.); 229~230 (dec.); Mass; 353 (M+H)⁺; NMR δ (DMSO-d$_6$); 3.88 (3H, s), 4.72 (2H, d, J=5.6 Hz), 5.96 (2H, s), 6.85 (1H, d, J=8.0 Hz), 6.91 (1H, d, J=8.0 Hz), 7.05 (1H, s), 7.40 (1H, dd, J=9.2 Hz, 2.8 Hz), 7.66 (1H, d, J=9.2 Hz), 7.69 (1H, d, J=2.8 Hz), 7.94 (1H, s), 8.62 (1H, brt, J=5.6 Hz), 11.63 (1H, s).

EXAMPLE 145

4-(3-Hydroxyiminomethylbenzyl)amino-6,7,8-trimethoxyquinazoline

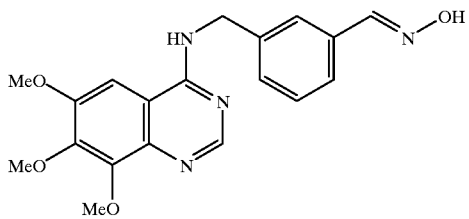

molecular formula; C$_{19}$H$_{20}$N$_4$O$_4$; yield(%); 56; m.p.(° C.); 231~232 (dec.); Mass; 369 (M+H)$^+$; NMR δ DMSO-d$_6$); 3.88 (3H, s), 3.91 (3H, s), 3.98 (3H, s), 4.80 (2H, d, J=6.0 Hz), 7.3~7.5 (3H, m), 7.52 (1H, s), 7.60 (1H, s), 8.11 (1H, s), 8.35 (1H, s), 8.60 (1H, brs), 11.17 (1H, s).

EXAMPLE 146

4-[4-(1Hydroxyiminoethyl)benzyl]amino-6-methoxyquinazoline

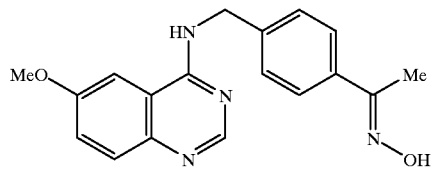

molecular formula; C$_{18}$H$_{18}$N$_4$O$_2$; yield(%); quantitative; m.p.(° C.); 245~246 (dec.); Mass; 323 (M+H)$^+$; NMR δ (DMSO-d$_6$); 2.13 (3H, s), 3.95 (3H, s), 4.97 (2H, d, J=5.6 Hz), 7.44 (2H, d, J=8.4 Hz), 7.63 (2H, d, J=8.4 Hz), 7.68 (1H, dd, J=9.2 Hz, 2.8 Hz), 7.83 (1H, d, J=9.2 Hz), 8.14 (1H, d, J=2.8 Hz), 8.84 (1H, s), 10.75 (1H, brs), 11.18 (1H, s).

EXAMPLE 147

4-(3-Amino-4-chlorobenzyl)amino-6-chloroquinazoline

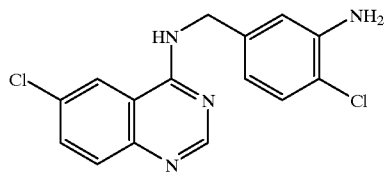

A mixture comprising 1.00 g (2.86 mmol) of 4-(4-chloro-3-nitrobenzyl)amino-6-chloroquinazoline, 0.85 g of powdered iron, 10 ml of acetic acid and 50 ml of ethanol was heated under reflux for several hours and distilled under a reduced pressure to remove the solvent. The residue was purified by silica gel column chromatography (ethyl acetate/n-hexane) to give 0.91 g of the title compound as a pale-yellow crystal.

molecular formula; C$_{15}$H$_{12}$N$_4$Cl$_2$; yield(%); quantitative; m.p.(° C.); 226~229 (dec.); Mass; 319 (M+H)$^+$; NMR δ (CDCl$_3$); 4.19 (2H, brs), 4.73 (2H, d, J=6.0 Hz), 6.71 (1H, dd, J=8.0 Hz, 2.0 Hz), 6.83 (1H, d, J=2.0 Hz), 7.18 (1H, d, J-8.0 Hz), 7.64 (1H, dd, J=8.8 Hz, 2.0 Hz), 7.72 (1H, brs), 7.74 (1H, d, J=8.8 Hz), 8.19 (1H, d, J=2.0 Hz), 8.60 (1H, s).

EXAMPLE 148

4-(4-Chloro-3-formamidobenzyl)amino-6-chloroquinazoline

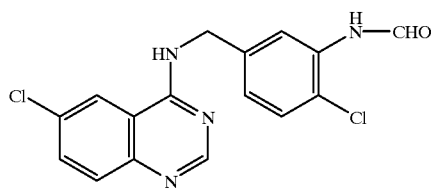

0.90 g (2.82 mmol) of the 4-(3-amino-4-chlorobenzyl)amino-6-chloroquinazoline prepared in Example 147 was dissolved in 15 ml of formic acid, followed by the addition of 1 ml of acetic anhydride. The obtained mixture was stirred at room temperature for several hours and distilled under a reduced pressure to remove the solvent. The residue was purified by silica gel column chromatography (ethyl acetate) and recrystallized from ethyl acetate to give 0.64 g of the title compound as a pale yellow crystal.

molecular formula; C$_{17}$H$_{15}$N$_4$O$_2$Cl (342.786); yield(%); 65; m.p.(° C.); 229~230; Mass; 347 (M+H)$^+$; NMR δ (DMSO-d$_6$); 4.74 (2H, d, J=5.6 Hz), 7.15 (1H, dd, J=8.4 Hz, 2.0 Hz), 7.43 (1H, d, J=8.4 Hz), 7.72 (1H, d, J=8.8 Hz), 7.80 (1H, dd, J=8.8 Hz, 2.0 Hz), 8.16 (1H, d, J=2.0 Hz), 8.32 (1H, d, J=2.0 Hz), 8.45 (1H, s), 8.46 (1H, s), 8.95 (1H, brs), 9.83 (1H, brs).

EXAMPLE 149

4-(3-Formamido-4-methoxybenzyl)amino-6-chloroquinazoline

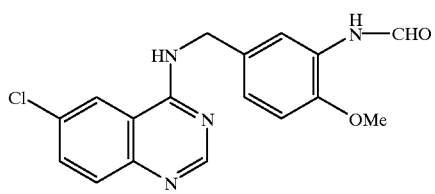

1 g of powdered iron was added in portions to a mixture comprising 1 g of 4-(3-nitro-4-methoxybenzyl)-amino-6-chloroquinazoline, 4 ml of acetic acid, 4 ml of water and 40 ml of ethanol, while heating the mixture under mild reflux. The obtained mixture was heated under reflux for 2 hours and filtered to remove insolubles. Concentrated hydrochloric acid was added in portions to the brown filtrate obtained above to give a yellow transparent solution. This solution was cooled with ice to precipitate crystals. The crystals were recovered by filtration and dried to give 1.1 g of 4-(3-amino-4-methoxybenzyl)amino-6-chloroquinazoline hydrochloride. This hydrochloride was dissolved in ethanol/water and the obtained solution was made alkaline by adding a 15% aqueous solution of sodium hydroxide in portions. Water was added to the resulting alkaline solution in portions to precipitate crystals. The crystals were recovered by filtration, washed with water and dried to give 770 mg of 4-(3-amino-4-methoxybenzyl)amino-6-chloroquinazoline (an aniline derivative). Separately, 1 ml of formic acid was dropped into 2 ml of acetic anhydride under cooling with ice and the obtained mixture was heated at 50° C. for 15 minutes and immediately cooled with ice, followed by the addition of the above aniline derivative as such (in a crystalline state). The obtained mixture was reacted at that temperature for one hour and at room temperature for one hour, followed by the addition of water. The crystals thus formed were recovered by filtration, washed with water and dried to give 130 mg of the title compound.

molecular formula; $C_{17}H_{15}N_4O_2Cl$ (342.786); yield(%); 60; m.p.(° C.); 208~209; Mass; 343 (MH)$^+$; NMR δ (DMSO-d$_6$); 3.82 (3H, s), 4.68 (2H, d, J=5.7 Hz), 6.98 (1H, d, J=8.2 Hz), 7.09 (1H, dd, J=2.0 Hz, 8.2 Hz), 7.71 (1H, d, J=9.0 Hz), 7.79 (1H, dd, J=2.4 Hz, 9.0 Hz), 8.23 (1H, d, J=2.0 Hz), 8.27 (1H, d, J=2.4 Hz), 8.47 (2H, s), 8.88 (1H, t, J=5.7 Hz), 9.62 (1H, brs).

EXAMPLE 150

4-(3-Methanesulfonylamino-4-chlorobenzyl)amino-6-chloroquinazoline

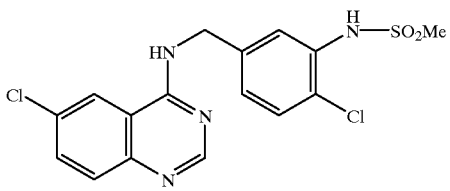

75 μl of methanesulfonyl chloride was added to a mixture comprising 100 mg of 4-(3-amino-4-chlorobenzyl)amino-6-chloroquinazoline and 3 ml of pyridine. The obtained mixture was stirred at room temperature for 1.5 hours. 20 ml of water was added in portions to the reaction mixture to precipitate crystals. The crystals were recovered by filtration, washed with water and dried to give 109 mg of the title compound.

molecular formula; $C_{16}H_{14}N_4O_2SCl_2$ (397.284); yield (%); 88; m.p.(° C.); 209~210; Mass; 397 (MH)$^+$; NMR δ (DMSO-d$_6$); 3.01 (3H, s), 4.75 (2H, d, J=5.7 Hz), 7.23 (1H, dd, J=2.2 Hz, 8.2 Hz), 7.45 (1H, d, J=8.2 Hz), 7.46 (1H, d, J=2.2 Hz), 7.73 (1H, d, J=9.0 Hz), 7.81 (1H, dd, J=2.4 Hz, 9.0 Hz), 8.45 (1H, d, J=2.4 Hz), 8.47 (1H, s), 8.97 (1H, brt, J=5.7 Hz), 9.4 (1H, brs).

EXAMPLES 151 TO 157

The following compounds were prepared in a similar manner to those of Examples 147 to 150.

EXAMPLE 151

4-(3-Amino-4-hydroxybenzyl)amino-6,7,8-trimethoxyquinazoline

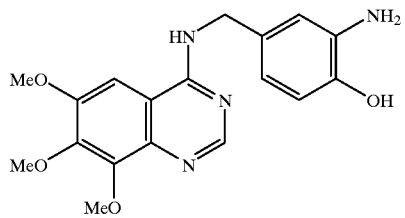

molecular formula; $C_{18}H_{20}N_4O_4$; yield(%); quantitative; m.p.(° C.); amorphous; Mass; 357 (M+H)$^+$; NMR δ (CDCl$_3$); 3.68 (1H, brs), 3.82 (1H, brs), 3.95 (3H, s), 4.02 (3H, s), 4.11 (3H, s), 4.68 (2H, d, J=4.4 Hz), 6.61 (1H, brs), 6.64 (1H, d, J=7.6 Hz), 6.77 (1H, d, J=7.6 Hz), 7.01 (1H, s), 8.50 (1H, brs), 8.60 (1H, s).

EXAMPLE 152

4-(3-Ethoxycarbonylamino-4-ethoxycarbonyloxybenzyl)-amino-6,7,8-trimethoxyquinazoline

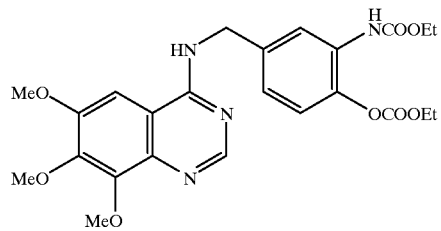

molecular formula; $C_{24}H_{28}N_4O_8$; yield(%); 54; m.p.(° C.); 229~230 (dec.); Mass; 501 (M+H)$^+$; NMR δ (CDCl$_3$); 1.31 (3H, t, J=7.2 Hz), 1.40 (3H, t, J=7.2 Hz), 3.95 (3H, s), 4.03 (3H, s), 4.11 (3H, s), 4.21 (2H, q, J=7.2 Hz), 4.35 (2H, q, J=7.2 Hz), 4.81 (1H, d, J=5.2 Hz), 5.80 (1H, brt, J=5.2 Hz), 6.74 (1H, s), 6.87 (1H, s), 7.13 (1H, d, J=8.0 Hz), 7.20 (1H, d, J=8.0 Hz), 8.18 (1H, brs), 8.64 (1H, s).

EXAMPLE 153

4-[Benzoxazol-2(3H)-on-5-ylmethyl]amino-6,7,8-trimethoxyquinazoline

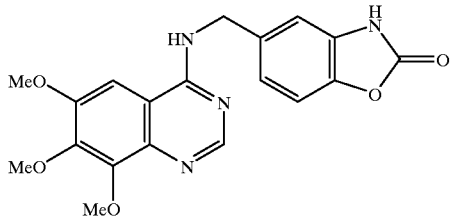

molecular formula; $C_{19}H_{18}N_4O_5$; yield(%); 62; m.p.(° C.); 232~233 (dec.); Mass; 383 (M+H)$^+$; NMR δ (DMSO-d$_6$); 3.87 (3H, s), 3.90 (3H, s), 3.96 (3H, s), 4.78 (2H, d, J=5.6 Hz), 7.06 (1H, s), 7.07 (1H, d, J=8.0 Hz), 7.20 (1H, d, J=8.0 Hz), 7.50 (1H, s), 8.35 (1H, s), 8.58 (1H, brt, J=5.6 Hz), 11.48 (1H, brs).

EXAMPLE 154

4-(4-Hydroxy-3-methanesulfonylaminobenzyl)amino-6,7,8-trimethoxyquinazoline

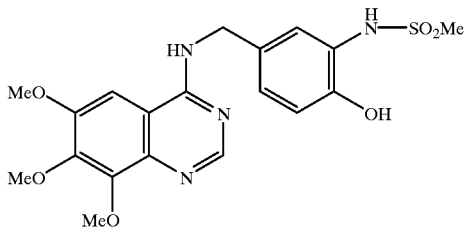

molecular formula; $C_{19}H_{22}N_4O_6S$; yield(%); 56; m.p.(° C.); 215~216 (dec.); Mass; 435 (M+H)⁺; NMR δ (DMSO-d₆); 2.91 (3H, s), 3.86 (3H, s), 3.89 (3H, s), 3.96 (3H, s), 4.65 (2H, d, J=5.6 Hz), 6.83 (1H, d, J=8.0 Hz), 7.04 (1H, dd, J=8.0 Hz, 2.0 Hz), 7.22 (1H, d, J=2.0 Hz), 7.50 (1H, s), 8.34 (1H, s), 8.52 (1H, brt, J=5.6 Hz), 8.66 (1H, brs), 9.75 (1H, brs).

EXAMPLE 155

4-(3-Amino-4-chlorobenzyl)amino-6,7,8-trimethoxyquinazoline

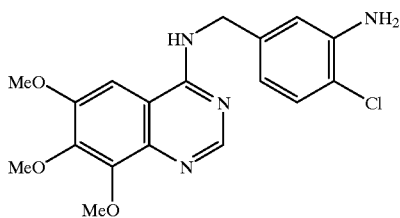

molecular formula; $C_{18}H_{19}N_4O_3Cl$; yield(%); 86; m.p.(° C.); 181~182 (dec.); Mass; 375 (M+H)⁺; NMR δ (CDCl₃); 3.95 (3H, s), 4.03 (3H, s), 4.08 (2H, brs), 4.13 (3H, s), 4.75 (2H, d, J=5.6 Hz), 5.65 (1H, brs), 6.67 (1H, s), 6.72 (1H, dd, J=8.0 Hz, 2.0 Hz), 6.81 (1H, d, J=2.0 Hz), 7.23 (1H, d, J=8.0 Hz), 8.65 (1H, s).

EXAMPLE 156

4-(4-Chloro-3-formamidobenzyl)amino-6,7,8-trimethoxyquinazoline

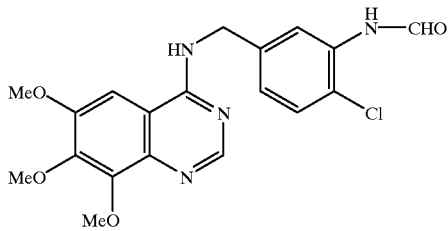

molecular formula; $C_{19}H_{19}N_4O_4Cl$; yield(%); 68; m.p.(° C.); 202~204 (dec.); Mass; 403 (M+H)⁺; NMR δ (DMSO-d₆); 3.88 (3H, s), 3.91 (3H, s), 3.98 (3H, s), 4.75 (2H, d, J=5.6 Hz), 7.14 (1H, dd, J=8.4 Hz, 2.0 Hz), 7.42 (2H, d, J=8.4 Hz), 7.52 (1H, s), 8.15 (1H, d, J=2.0 Hz), 8.32 (1H, s), 8.35 (1H, s), 8.67 (1H, brs), 9.83 (1H, brs).

EXAMPLE 157

4-(3-Acetamido-4-chlorobenzyl)amino-6-chloroquinazoline

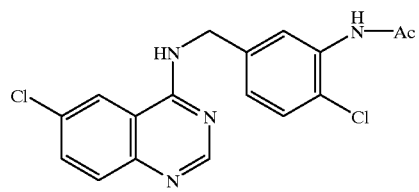

molecular formula; $C_{17}H_{14}N_4OCl_2$ (361.232); yield(%); 77; m.p.(° C.); 267~268; Mass; 361 (MH)⁺; NMR δ (DMSO-d₆); 2.06 (3H, s), 4.74 (2H, d, J=5.7 Hz), 7.17 (1H, dd, J=2.0 Hz, 8.2 Hz), 7.42 (1H, d, J=8.2 Hz), 7.69 (1H, brs), 7.72 (1H, d, J=9.0 Hz), 7.81 (1H, dd, J=2.4 Hz, 9.0 Hz), 8.45 (1H, d, J=2.4 Hz), 8.46 (1H, s), 8.96 (1H, brt, J=5.7 Hz), 9.48 (1H, brs).

EXAMPLE 158

4-(3,4-Dihydroxybenzyl)amino-6,7,8-trimethoxyquinazoline hydrochloride

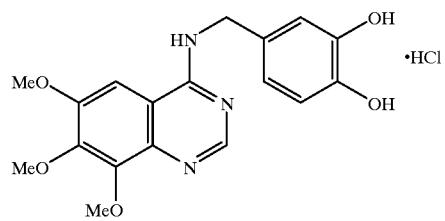

30 ml of a 1.0 M solution of boron trichloride in methylene chloride was dropped into a solution of 2.00 g (5.41 mmol) of 4-(3,4-methylenedioxybenzyl)amino-6,7,8-trimethoxyquinazoline in 150 ml of chloroform under stirring at room temperature. The obtained mixture was stirred at room temperature for 2 days, followed by the addition of methanol and the obtained mixture was distilled under a reduced pressure to remove the solvent. This procedure was repeated thrice and the obtained residue was purified by silica gel column chromatography (chloroform/n-hexane). Hydrochloric acid/ethanol was added to the eluate and the obtained mixture was distilled under a reduced pressure to remove the solvent, followed by the addition of ethanol. The crystals thus formed were recovered by filtration. Thus, 0.59 g of the title compound was obtained as a colorless needle.

molecular formula; $C_{18}H_{19}N_3O_5$.HCl; yield(%); 28; m.p.(° C.); 204~205 (dec.); Mass; 358 (M+H)⁺; NMR δ (DMSO-d₆); 3.98 (3H, s), 3.99 (3H, s), 3.99 (3H, s), 4.78 (2H, d, J=5.6 Hz), 6.65~7.71 (2H, m), 6.79 (1H, s), 7.94 (1H, s), 8.71 (1H, s), 8.90 (2H, brs), 10.54 (1H, brs), 14.06 (1H, brs).

EXAMPLE 159

4-(3,4-Dihydroxybenzyl)amino-6-chloroquinazoline hydrochloride

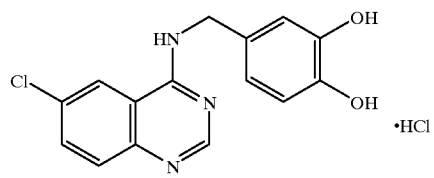

40 ml of a 1.0 M solution of boron trichloride in methylene chloride was dropped into a solution of 2.00 g (6.37 mmol) of 4-(3,4-methylenedioxybenzyl)amino-6-chloroquinazoline in 150 ml of chloroform under stirring at room temperature. The obtained mixture was stirred at room temperature for 2 days, followed by the addition of methanol, and the obtained mixture was distilled under a reduced pressure to remove the solvent. This procedure was repeated twice. The crystals thus precipitated were washed with methanol and recrystallized from ethanol to give 1.53 g of the title compound as a yellow crystal.

molecular formula; $C_{15}H_{12}N_3O_2Cl \cdot HCl$; yield(%); 71; m.p.(° C.); 154~155 (dec.); Mass; 302 (M+H)$^+$; NMR δ (DMSO-d$_6$); 4.74 (2H, d, J=5.6 Hz), 7.67 (1H, dd, J=8.0 Hz, 2.0 Hz), 6.70 (1H, d, J=8.0 Hz), 6.81 (1H, d, J=2.0 Hz), 7.87 (1H, d, J=8.8 Hz), 8.02 (1H, dd, J=8.8 Hz, 2.0 Hz), 8.76 (1H, d, J=2.0 Hz), 8.85 (1H, s), 8.90 (2H, brs), 10.42 (1H, brs).

EXAMPLES 160 TO 163

The following compounds were prepared in a similar manner to those of Examples 158 to 159.

EXAMPLE 160

2-Methoxy-4-(3,4-methylenedioxybenzyl)amino-6-chloroquinazoline

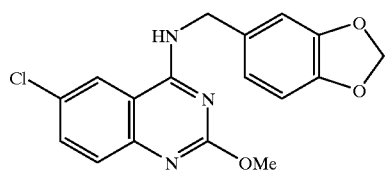

molecular formula; $C_{17}H_{14}N_3O_3Cl$; yield(%); 15; m.p.(° C.); 187~189; Mass; 344 (M+1)$^+$; NMR δ (CDCl$_3$); 4.03 (3H, s), 4.50 (2H, d, J=5.6 Hz), 5.91 (1H, br), 5.96 (2H, s), 6.78 (1H, d, J=7.6 Hz), 6.81 (1H, dd, J=7.6 Hz, 1.6 Hz), 6.82 (1H, d, J=1.6 Hz), 7.58~7.60 (3H, m).

EXAMPLE 161

2-Methoxy-4-(3,4-methylenedioxybenzyl)amino-6-cyanoquinazoline

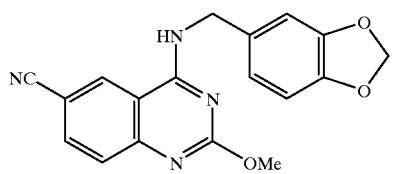

molecular formula; $C_{18}H_{14}N_4O_3$ (334); yield(%); 23; m.p.(° C.); 224 (dec.); Mass; 335 (M+1)$^+$; NMR δ (DMSO-d$_6$); 3.87 (3H, s), 4.60 (2H, brs), 5.95 (2H, s), 6.84 (2H, s), 6.95 (1H, s), 7.55 (1H, d, J=8.8 Hz), 7.94 (1H, dd, J=8.8 Hz, 1.6 Hz), 8.83 (1H, d, J=1.6 Hz), 9.18 (1H, br).

EXAMPLE 162

2,6,7,8-Tetramethoxy-4-(3,4-methylenedioxybenzyl)-aminoquinazoline

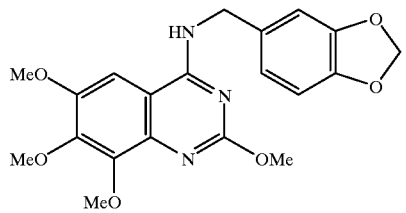

molecular formula; $C_{20}H_{21}N_3O_6$; yield(%); 28; m.p.(° C.); 128~129; Mass; 400 (M+H)$^+$; NMR δ (CDCl$_3$); 3.91 (3H, s), 4.04 (3H, s), 4.07 (3H, s), 4.14 (3H, s), 4.75 (2H, d, J=5.2 Hz), 5.51 (1H, brs), 5.97 (2H, s), 6.60 (1H, s), 6.80 (1H, d, J=8.0 Hz), 6.87 (1H, dd, J=8.0 Hz, 2.0 Hz), 6.90 (1H, d, J=2.0 Hz).

EXAMPLE 163

2-Hydroxy-4-(3,4-methylenedioxybenzyl)amino-6-chloroquinazoline

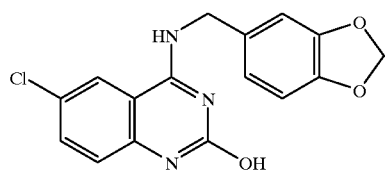

molecular formula; $C_{16}H_{12}N_3O_3Cl$ (329.5); m.p.(° C.); 257 (dec.); NMR δ (DMSO-d$_6$); 4.668 (2H, d, J=5.6 Hz), 5.967 (2H, s), 6.846~6.905 (2H, m), 6.995 (1H, s), 7.821 7.859 (2H, m), 8.508 (1H, s), 10.103 (1H, br), 11.916 (1H, s).

EXAMPLE 164

2-Chloro-4,6,7,8-tetramethoxyquinazoline

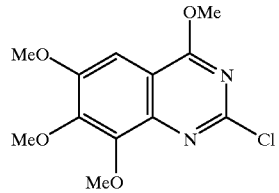

5.00 g (17.3 mmol) of 2,4-dichloro-6,7,8-trimethoxyquinazoline was suspended in 100 ml of methanol, followed by the gradual addition of 1.5 g of sodium hydride. The obtained mixture was heated under reflux. After several hours, the reaction mixture was concentrated under a reduced pressure, followed by the addition of water. The crystal thus precipitated was recovered by filtration, washed with water and air-dried to give 4.80 g of the title compound as a pale-pink crystal.

yield(%); 97; m.p.(° C.); 119~120; Mass; 285 (M+1)$^+$; NMR δ (CDCl$_3$); 3.98 (3H, s), 4.06 (3H, s), 4.12 (3H, s), 4.19 (3H, s), 7.17 (1H, s).

EXAMPLE 165

2-Benzyloxymethyl-4-chloro-6-methoxyquinazoline

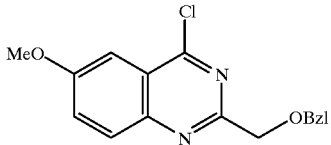

30 ml of phosphorus oxychloride was added to a suspension of 1.50 g (5.06 mmol) of 2-benzyloxymethyl-6-methoxyquinazoline-4(3H)-one in 75 ml of acetonitrile. The obtained mixture was heated under reflux. After one hour, the reaction mixture was distilled under a reduced pressure to remove the solvent and the obtained residue was dissolved in chloroform. The obtained solution was washed with a saturated aqueous solution of sodium hydrogencarbonate. The organic layer was dried over anhydrous magnesium sulfate and filtered. The filtrate was distilled under a reduced pressure to remove the solvent. The residue was purified by silica gel column chromatography (ethyl acetate/n-hexane) to give 1.10 g of the title compound as a yellow crystal.

yield(%); 69; m.p.(° C.); 49~50; Mass; 315 (M+1)$^+$; NMR δ (CDCl$_3$); 3.98 (3H,s), 4.79 (2H, s), 4.84 (2H, s), 7.42 (1H, d, J=2.8 Hz), 7.26~7.46 (5H, m), 7.57 (1H, dd, J=9.2 Hz, 2.8 Hz), 8.01 (1H, d, J=9.2 Hz).

EXAMPLE 166

2-Benzyloxymethyl-4-(3,4-methylenedioxybenzyl) amino-6-methoxyquinazoline

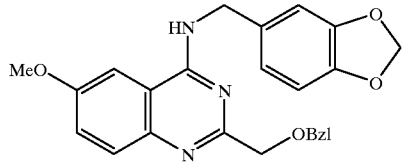

0.74 g (2.4 mmol) of the 2-benzyloxymethyl-4-chloro-6-methoxyquinazoline prepared in Example 165, 0.55 g (3.6 mmol) of piperonylamine and 0.50 g of sodium carbonate were mixed with 20 ml of isopropyl alcohol. The obtained mixture was heated under reflux. After 6 hours, the reaction mixture was distilled under a reduced pressure to remove the solvent and the residue was purified by silica gel column chromatography (ethyl acetate/n-hexane) and recrystallized from chloroform/n-hexane to give 1.01 g of the title compound as a yellow crystal.

molecular formula; C$_{25}$H$_{23}$N$_3$O$_4$; yield(%); quantitative; m.p.(° C.); 158~159; NMR δ (CDCl$_3$); 3.91 (3H, s), 4.69 (2H, s), 4.77 (2H, s), 4.79 (2H, d, J=5.6 Hz), 5.94 (2H, s), 6.77 (1H, d, J=7.6 Hz), 6.90 (1H, dd, J=7.6 Hz, 1.6 Hz), 6.94 (1H, d, J=1.6 Hz), 7.10 (1H, brs), 7.25~7.35 (5H, m), 7.41~7.44 (2H, m), 7.81 (1H, d, J=9.2 Hz).

EXAMPLE 167

2,6-Dichloro-4-(3,4-methylenedioxybenzyl) oxyquinazoline

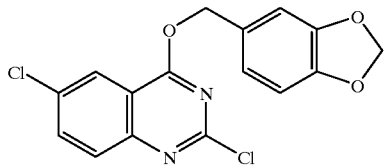

molecular formula; C$_{16}$H$_{10}$Cl$_2$N$_2$O$_3$; yield(%); 55; m.p.(° C.); 141~142; Mass m/e; 349 (M+1); NMR δ (CDCl$_3$); 5.54 (2H, s), 6.01 (2H, s), 6.86 (1H, d, J=8.8 Hz), 7.01 (1H, d, J=8.8 Hz), 7.02 (1H, s), 7.76 (1H, dd, J=8.0 Hz, 2.4 Hz), 7.81 (1H, dd, J=8.0 Hz, 0.8 Hz), 8.09 (1H, dd, J=2.4 Hz, 0.8 Hz).

EXAMPLE 168

2,6-Dichloro-4-(3,4-methylenedioxybenzyl)-thiochloroquinazoline

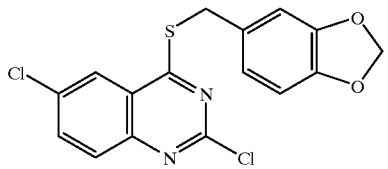

molecular formula; C$_{16}$H$_{10}$Cl$_2$N$_2$O$_2$S; yield(%); 92; m.p.(° C.); 180~182; Mass m/e; 365 (M+1); NMR δ (CDCl$_3$); 4.55 (2H, s), 5.96 (2H, s), 6.77 (1H, d, J=8.4 Hz), 6.96 (1H, s), 6.96 (1H, d, J=8.4 Hz), 7.77 (1H, dd, J=8.8 Hz, 2.0 Hz), 7.82 (1H, d, J=8.8 Hz), 7.99 (1H, dd, J=2.0 Hz).

EXAMPLE 169

2,6-Dichloro-4-(3,4-methylenedioxybenzyl) aminoquinoline

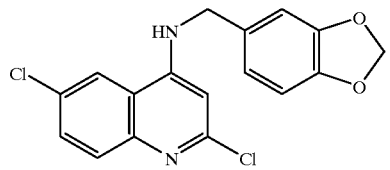

a) 2,4,6-Trichloroquinoline

The title compound was prepared from methyl 5-chloroanthranilate in a similar manner to that described in Journal of American Chemical Society, 68 1285 (1946).

NMR δ (CDCl$_3$); 7.55(1H, s), 7.74(1H, dd, J=9.0 Hz, 2.2 Hz), 7.98(1H, d, J=9.0 Hz), 8.19(1H, d, J=2.2 Hz).

b) 2,6-Dichloro-4-(3,4-methylenedioxybenzyl)-aminoquinoline

A reaction of a mixture comprising 500 mg of the compound prepared in the step (a), 350 mg of 3,4-methylenedioxybenzylamine, 1 ml of N,N-diisopropyl-ethylamine and 4 ml of N-methyl-2-pyrrolidone was conducted on an oil bath of 130° C. for 10 hours. Water was added to the reaction mixture and the obtained mixture was extracted with ethyl acetate. The ethyl acetate layer was washed with water and a saturated aqueous solution of sodium chloride, dried over anhydrous magnesium sulfate, and concentrated. The residue was subjected to column chromatography with 5 to 20% ethyl acetate/hexane to give 430 mg of the title compound as a highly polar component.

molecular formula; C$_{17}$H$_{12}$Cl$_2$N$_2$O$_3$; m.p.(° C.); 198~199; Mass m/e; 347 (M+1); NMR δ (CDCl$_3$); 4.39(2H, d, J=4.9 Hz), 5.21(1H, t, J=4.9 Hz), 6.00(2H, s), 6.47(1H, s), 6.82~6.87(3H, m), 7.58(1H, dd, J=9.0 Hz, 2.2 Hz), 7.65(1H, d, J=2.2 Hz), 7.84(1H, d, J=9.0 Hz).

Simultaneously, 190 mg of 4,6-dichloro-2-(3,4-methylenedioxybenzyl)aminoquinoline was obtained as a lowly polar component.

NMR δ (CDCl$_3$); 4.58(2H, d, J=5.7 Hz), 5.00(1H, brt, J=5.7 Hz), 5.94(2H, s), 6.74(1H, s), 6.77(1H, d, J=7.9 Hz), 6.84(1H, dd, J=7.9 Hz, 1.6 Hz), 6.88(1H, d, J=1.6 Hz), 7.50(1H, dd, J=9.0 Hz, 2.4 Hz), 7.62(1H, d, J=9.0 Hz), 7.96(1H, d, J=2.4 Hz).

EXAMPLE 170

2,6-Dichloro-4-(3-chloro-4-methoxybenzylamino)quinoline

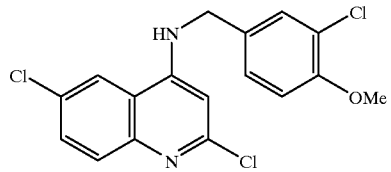

The title compound was prepared in a similar manner to that of Example 253.

molecular formula; C$_{17}$H$_{13}$Cl$_3$N$_2$O; yield(%); 59; m.p.(° C.); 204~205; NMR δ (CDCl$_3$); 3.91(3H, s), 3.40(3H, s), 4.38(2H, d, J=5.1 Hz), 4.97(1H, t, J=5.1 Hz), 5.93(1H, s), 6.93(1H, d, J=8.4 Hz), 7.24(1H, dd, J=8.4 Hz, 2.2 Hz), 7.40(1H, d, J=2.2 Hz), 7.50(1H, dd, J=8.8 Hz, 2.2 Hz), 7.59 (1H, d, J=2.2 Hz), 7.71(1H, d, J=8.8 Hz).

EXAMPLE 171

2-Methoxy-4-(3-chloro-4-methoxybenzyl)amino-6-chloroquinoline

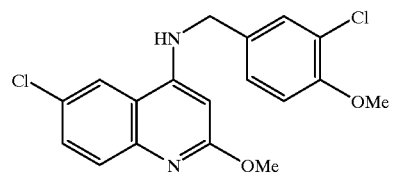

A mixture comprising 200 mg of 2.6-dichloro-4-(3-chloro-4-methoxybenzyl)aminoquinoline, 0.5 ml of methanol, 200 mg of potassium t-butoxide and 3 ml of 1,4-dioxane was heated under reflux for one hour and cooled, followed by the addition of water. The resulting mixture was extracted with ethyl acetate and the ethyl acetate layer was washed with a saturated aqueous solution of sodium chloride, dried over anhydrous magnesium sulfate, and concentrated. The residue was purified by silica gel column chromatography with 10 to 30% ethyl acetate/hexane and recrystallized from ethyl acetate/hexane to give 150 mg of the title compound.

molecular formula; C$_{18}$H$_{16}$Cl$_2$N$_2$O$_2$; yield(%); 76; m.p.(° C.); 170~171; NMR δ (CDCl$_3$); 3.93(3H, s), 4.42(2H, d, J=5.2 Hz), 5.22(1H, t, J=5.2 Hz), 6.46(1H, s), 6.96(1H, d, J=8.4 Hz), 7.25(1H, dd, J=8.4 Hz, 2.2 Hz), 7.41(1H, d, J=2.2 Hz), 7.59(1H, dd, J=9.0 Hz, 2.2 Hz), 7.66(1H, d, J=2.2 Hz), 7.85(1H, d, J=9.0 Hz).

EXAMPLE 172

2-Chloro-4-(3-chloro-4-methoxybenzyl)amino-6-cyanoquinoline

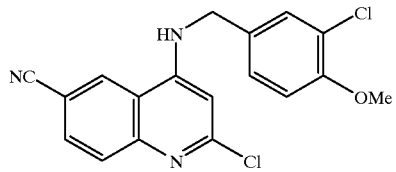

a) 4-Hydroxyquinolin-2-one-6-carboxylic acid

The title compound was prepared from dimethyl 4-aminobenzene-1,4-dicarboxylate in a similar manner to that described in Journal of American Chemical Society, 68, 1285(1946).

NMR δ (DMSO-d$_6$); 5.79(1H, s), 7.31(1H, d, J=8.6 Hz), 8.02(1H, dd, J=8.6 Hz, 2.0 Hz), 8.39(1H, d, J=2.0 Hz), 11.51(1H, s), 11.63(1H, brs), 12.86(1H, brs).

b) 2,4-Dichloroquinoline-6-carboxamide

A mixture comprising 9 g of the compound prepared in the step (a) and 50 ml of phosphorus oxychloride was heated under reflux for one hour. The reaction mixture was concentrated and ethyl acetate/acetone was added to the obtained residue to form a homogeneous suspension. This suspension was gradually poured into a concentrated aqueous ammonia cooled with ice under stirring. After 30 minutes, the crystals thus precipitated were recovered by filtration, washed with water and ethyl acetate, and dried to give 8.96 g of the title compound.

NMR δ (DMSO-D$_6$); 7.72(1H, brs), 8.06(1H, s), 8.10(1H, d, J=8.8 Hz), 8.34(1H, dd, J=8.8 Hz, 2.0 Hz), 8.43(1H, brs), 8.73(1H, d, J=2.0 Hz).

A mixture comprising 3 g of the compound prepared in the step (b), 300 mg of lithium chloride and 30 ml of phosphorus oxychloride was heated under reflux for 2 hours. The reaction mixture was concentrated, followed by the addition of 120 ml of benzene. The resulting mixture was washed with a saturated aqueous solution of sodium chloride, dried over anhydrous magnesium sulfate, and filtered through a silica gel bed. The silica gel was further washed with benzene. The benzene solutions were combined and concentrated and the residue was recrystallized from ethyl acetate/hexane to give 2.15 g of the title compound.

7.65(1H, s), 7.95(1H, dd, J=8.8 Hz, 1.8 Hz), 8.14(1H, d, J=8.8 Hz), 8.60(1H, d, J=1.8 Hz)

d) 2-Chloro-4-(3-chloro-4-methoxybenzyl)amino-6-cyanoquinoline

A reaction of a mixture comprising 1 g of the compound prepared in the step (c), 1 g of 3-chloro-4-methoxybenzylamine hydrochloride, 2.4 ml of N,N-diisopropylethylamine and 10 ml of N-methyl-2-pyrrolidone was conducted on an oil bath at 130° C. for one hour. The reaction mixture was cooled, followed by the addition of water and ethyl acetate. The crystals thus precipitated were recovered by filtration, washed with water and ethyl acetate, and dried to give 610 mg of the title compound.

molecular formula; C$_{18}$H$_{13}$Cl$_2$N$_3$O; yield(%); 38; m.p.(° C.); 254~255; NMR δ (CDC$_3$); 3.94(3H, s), 4.45(2H, d, J=4.9 Hz), 5.41(1H, d, J=4.9 Hz), 6.54(1H, s), 6.98(1H, d, J=8.4 Hz), 7.26(1H, dd, J=8.4 Hz, 2.2 Hz), 7.41(1H, d, J=2.2 Hz), 7.80(1H, dd, J=8.8 Hz, 1.6 Hz), 7.97(1H, d, J=8.8 Hz), 8.08(1H, d, J=1.6 Hz).

EXAMPLE 173

2-Chloro-8-(3,4-methoxydioxybenzyl)aminopyrido[2,3-d]polyrimidine

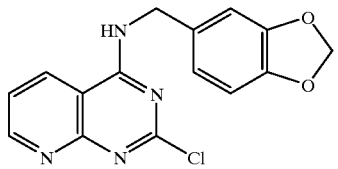

66 mg of triethylamine and 89 mg of piperonylamine were added to a solution of 118 mg of 2.8-dichloropyrido[2,3-d]pyrimidine in 20 ml of tetrahydrofuran. The obtained mixture was stirred at room temperature for 16 hours, followed by the addition of water. The crystals thus precipitated were recovered by filtration, whereby 166 mg of the title compound was obtained.

molecular formula; C$_{15}$H$_{11}$ClN$_4$O$_2$; yield(%); 89; m.p.(° C.); 200~202; Mass m/e; 315 (M+1); NMR δ (DMSO-d$_6$); 4.64(1H, J=5.6 Hz), 5.97(2H, s), 6.85(1H, d, J=8.0 Hz), 6.87(1H, d, J=8.0 Hz), 6.96(1H, s), 7.55(1H, dd, J=8.0 Hz, 4.4 Hz), 8.73(1H, dd, J=8.0 Hz, 1.6 Hz), 8.96(1H, dd, J=4.4 Hz, 1.6 Hz), 9.46(1H, t, J=5.6 Hz).

EXAMPLES 174 TO 180

The following compounds were prepared in a similar manner to those of Examples 86 to 92.

EXAMPLE 174

2,6-Dichloro-4-(4-ethoxycarbonylpiperidino)quinazoline

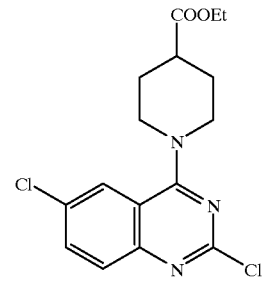

molecular formula; C$_{16}$H$_{17}$Cl$_2$N$_3$O$_2$; yield(%); 100; m.p.(° C.); 101~103; Mass m/e; 354(M+1); NMR δ (CDCl$_3$); 1.30 (3H, t, J=7.2 Hz), 1.99 (2H, m), 2.14 (2H, m), 2.69 (1H, m), 3.35 (2H, dt, J=11.2 Hz, 2.4 Hz), 4.20 (2H, q, J=7.2 Hz), 4.31 (2H, dt, J=13.6 Hz3.6 Hz), 7.67 (1H, dd, J=8.8 Hz, 2.2 Hz), 7.76 (1H, d, J=8.8 Hz), 7.79 (1H, d, J=2.2 Hz).

EXAMPLE 175

2,6-Dichloro-4-(5-hydroxypentyl)aminoquinazoline

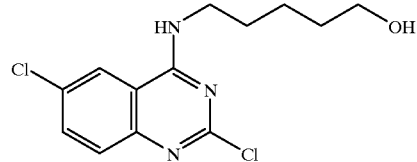

molecular formula; C$_{13}$H$_{15}$Cl$_2$N$_3$O; yield(%); 82; m.p.(° C.); 134~135; Mass m/e; 300 (M+1)$^+$; NMR δ (CDCl$_3$); 1.53(2H, m), 1.65(2H, m), 1.76(2H, m), 3.63(2H, m) 3.66 (2H, m), 7.61(1H, dd, J=8.8 Hz, 2.4 Hz), 7.67(1H, d, J=8.8 Hz), 7.85(1H, brs), 8.20(1H, d, J=2.4 Hz).

EXAMPLE 176

2-(Carboxymethyl)methylamino-4-(3-pyridylmethyl)amino-6-chloroquinazoline

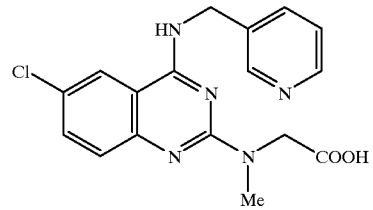

molecular formula; C$_{17}$H$_{16}$ClN$_5$O$_2$; yield(%); 97; m.p.(° C.); 222~223; Mass m/e; 358 (M+1); NMR δ (DMSO-d$_6$); 3.10(3H, s), 4.22(2H, brs), 4.63(2H, brs), 7.31(2H, m), 7.48(1H, m), 7.72(1H, m), 8.14(1H, d, J=2.4 Hz), 8.43(1H, d, J=4.8 Hz), 8.59(1H, m), 8.66(1H, brs).

EXAMPLE 177

2-[N-(3-Carboxypropyl)-N-methylamino]-4-(3-pyridylmethyl)amino-6-chloroquinazoline

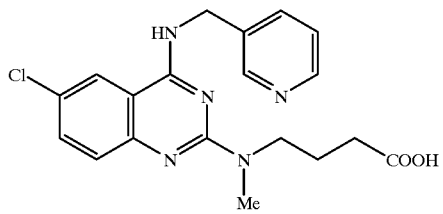

molecular formula; $C_{19}H_{20}ClN_5O_2$; yield(%); 41; m.p.(° C.); 110~112; Mass m/e; 386 (M+1); NMR δ (DMSO-$d_6$); 1.67(2H, brs), 2.09(2H, m), 3.02(3H, s), 3.53(2H, t, J=6.8 Hz), 4.67(2H, d, J=5.6 Hz), 7.24(2H, d, J=8.8 Hz), 7.31(1H, dd, J=8.0 Hz, 4.8 Hz), 7.47(1H, dd, J=8.8 Hz, 2.0 Hz), 7.73(1H, d, J=8.0 Hz), 8.13(1H, d, J=2.0 Hz), 8.41(1H, d, J=4.8 Hz), 8.58(1H, s), 8.62(1H, brs), 12.04(1H, brs).

EXAMPLE 178

2-(4-Carboxypiperidino)-4-(2-pyridylmethyl)amino-6-chloroquinazoline

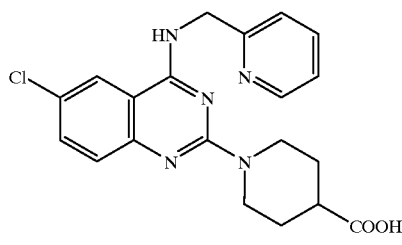

molecular formula; $C_{20}H_{20}ClN_5O_2$; yield(%); 92; m.p.(° C.); 235~237; Mass m/e; 398 (M+1); NMR δ (DMSO-$d_6$); 1.25~1.45(2H, m), 1.71~1.83(2H, m), 2.45~2.54(1H, m), 2.93~3.10(2H, m), 4.37~4.48(2H, m), 4.77(2H, d, J=5.5 Hz), 7.25(1H, dd, J=7.7 Hz, 5.0 Hz), 7.37(1H, d, J=7.7 Hz), 7.48(1H, brs), 7.63(1H, brs), 7.73(1H, td, J=7.7 Hz, 1.6 Hz), 8.34(1H, brs), 8.51(1H, brd, J=5.0 Hz), 12.23(1H, brs).

EXAMPLE 179

2-(4-Carboxypiperidino)-4-(3-pyridylmethyl)amino-6-chloroquinazoline

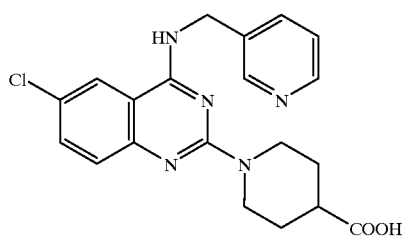

molecular formula; $C_{20}H_{20}ClN_5O_2$; yield(%); 93; m.p.(° C.);>250; Mass m/e; 398 (M+1); NMR δ (DMSO-$d_6$); 1.45~1.60(2H, m), 1.84~1.97(2H, m), 2.58~2.68(1H, m), 3.25~3.45(2H, m), 4.45~4.54(2H, m), 4.80(2H, d, J=5.7 Hz), 7.41(1H, dd, J=7.9 Hz, 4.8 Hz), 7.82(1H, dd, J=9.0 Hz, 2.0 Hz), 7.86~7.96(2H, m), 8.50(1H, d, J=4.8 Hz), 8.55(1H, d, J=1.6 Hz), 8.69(1H, s).

EXAMPLE 180

2-(4-Carboxypiperidino)-4-(4-pyridylmethyl)amino-6-chloroquinazoline

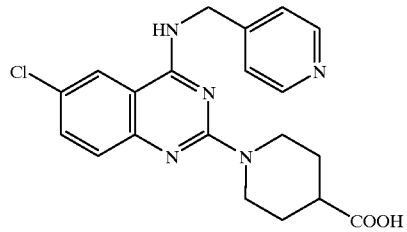

molecular formula; $C_{20}H_{20}ClN_5O_2$; yield(%); 89; m.p.(° C.); 167~168; Mass m/e; 398 (M+1); NMR δ (DMSO-$d_6$); 1.24~1.36(2H, m), 1.68~1.77(2H, m), 2.40~2.49(1H, m), 2.86~2.96(2H, m), 4.42~4.50(2H, m), 4.66(2H, d, J=5.7 Hz), 7.28(1H, d, J=9.0 Hz), 7.34(2H, d, J=6.0 Hz), 7.51(1H, dd, J=9.0 Hz, 2.4 Hz), 8.18(1H, d, J=2.4 Hz), 8.47(2H, d, J=6.0 Hz), 8.74(1H, t, J=5.7 Hz).

EXAMPLE 181

2-(6-Nitroxyhexyloxy)-4-(3,4-methylenedioxybenzyl)amino-6-chloroquinazoline

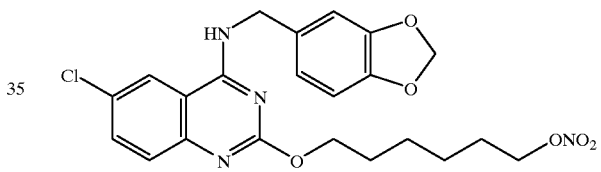

860 mg of 2-(6-Hydroxyhexyloxy)-4-(3,4-methylenedioxybenzyl) amino-6-chloroquinazoline was dissolved in 15 ml of pyridine, followed by the addition of 570 mg of methyl chloride under cooling with ice. The obtained mixture was stirred for 10 hours, followed by the addition of water. The resulting mixture was extracted with ethyl acetate. The ethyl acetate layer was dried and concentrated to give 1.2 g of crude 2-(6-tosyloxyhexyloxy)-4-(3,4-methylenedioxybenzyl)amino-6-chloroquinazoline.

3 g of sodium iodide and 30 ml of dimethyl-formamide were added to the crude product. The obtained mixture was maintained at 60° C. by heating for one hour, followed by the addition of water. The resulting mixture was extracted with ethyl acetate. The organic layer was washed with an aqueous solution of sodium chloride, dried and concentrated. The residue was purified by silica gel column chromatography to give 450 mg of 2-(6-iodohexyloxy)-4-(3,4-methylenedioxybenzyl)amino-6-chloroquinazoline.

410 mg of the 2-(6-iodohexyloxy)-4-(3,4-methylenedioxybenzyl)amino-6-chloroquinazoline was suspended in 15 ml of acetonitrile, followed by the addition of 900 mg of silver nitrate. The obtained mixture maintained at 60° C. by heating for one hour, followed by the addition of water and ethyl acetate. The resulting mixture was filtered through Celite to remove insolubles. The organic layer was recovered, dried and subjected to silica gel column chromatography to give 340 mg of the title compound.

molecular formula; $C_{22}H_{23}ClN_4O_6$ (474.5); yield(%); 95; m.p.(° C.); 121~122; Mass; 475 (MH$^+$); NMR δ (CDCl$_3$); 1.42~1.59 (4H, m), 1.70~1.89 (4H, m), 4.43 (4H, q, J=6.8 Hz), 4.73 (2H, d, J=4.4 Hz), 5.95 (2H, s), 6.28 (1H, br), 6.77 (1H, d, J=8.0 Hz), 6.83 (1H, d, J=8.0 Hz), 6.85 (1H, s), 7.54 (1H, d, J=8.8 Hz), 7.58 (1H, d, J=8.8 Hz), 7.66 (1H, s).

EXAMPLE 182

Sodium 2-(3-sulfoxypropoxy)-4-(3,4-methylenedioxybenzyl)amino-6-chloroquinazoline

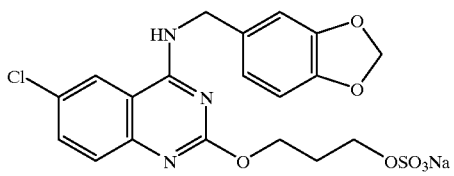

1 g of 2-(3-hydroxypropoxy)-4-(3,4-methylenedioxybenzyl)amino-6-chloroquinazoline and 540 mg of sulfur trioxide/trimethylamine complex were suspended in 10 ml of pyridine. The obtained suspension was stirred at room temperature overnight, followed by the addition of ethyl acetate. The crystals thus precipitated were recovered by filtration, suspended in methanol and dissolved therein by the addition of 1N sodium hydroxide. Ether was added to the obtained solution to precipitate crystals. The crystals were recovered by filtration, whereby 400 mg (32%) of the title compound was obtained.

molecular formula; $C_{19}H_{17}ClN_3NaO_7S$ (489.5); yield (%); 32; m.p.(° C.); 190~192 (dec.); Mass; 490 (MH$^+$); NMR δ (DMSO-d$_6$); 1.90~1.95 (2H, m), 3.82 (2H, t, J=6.4 Hz), 4.28 (2H, t, J=6.8 Hz), 4.61 (2H, d, J=5.6 Hz), 5.95 (2H, s), 6.84 (2H, s), 6.98 (1H, s), 7.50 (1H, d, J=8.8 Hz), 7.64 (1H, dd, J=8.8 Hz, 2.4 Hz), 8.84 (1H, d, J=2.4 Hz), 8.79 (1H, t, J=1.6 Hz).

EXAMPLE 183

2-(4-Ethoxycarboxypiperidino)carbonyl-4-(3,4-methylenedioxybenzyl)amino-6-chloroquinazoline hydrochloride

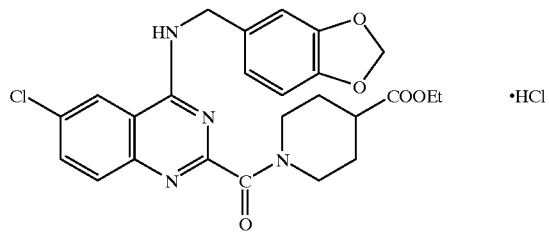

A solution of 0.50 ml (3.3 mmol) of diethyl cyanophosphate in 3 ml of dimethylformamide and 0.50 ml (3.6 mmol) of triethylamine were dropped, in this order, into a solution of 0.78 g (2.2 mmol) of 2-carboxy-4-(3,4-methylenedioxybenzyl)amino-6-chloroquinazoline and 0.50 g (3.2 mmol) of ethyl isonipecotate in 7 μl of dimethylformamide under cooling with ice and stirring. The obtained mixture was stirred under cooling with ice for 30 minutes and thereafter at room temperature for 3 hours, followed by the addition of water. The resulting mixture was extracted with ethyl acetate and the organic layer was dried over anhydrous magnesium sulfate and filtered. The filtrate was distilled in a vacuum to remove the solvent. The residue was recrystallized from hydrochloric acid/ethanol/ether to give 0.96 g of the title compound.

molecular formula; $C_{25}H_{25}ClN_4O_5$.HCl; yield(%); 82; m.p.(° C.); 205~206 (dec.); Mass m/e; 497 (M+1); NMR δ (DMSO-$_6$); 1.18(3H, t, J=7.2 Hz), 1.51(2H, m), 1.70(1H, m), 1.95(1H, m), 2.66(1H, m), 3.02(1H, m), 3.11(1H, m), 3.62 (1H, m), 4.08(2H, q, J=7.2 Hz), 4.31(1H, m), 4.71(1H, dd, J=14.9 Hz, 6.0 Hz), 4.78(1H, dd, J=14.9 Hz, 6.0 Hz), 5.97(2H, s), 6.84(1H, d, J=8.0 Hz), 6.87(1H, dd, J=8.0 Hz, 1.2 Hz), 6.97(1H, d, J=1.2 Hz), 7.82(1H, d, J=9.2 Hz), 7.97(1H, dd, J=9.2 Hz, 2.0 Hz), 8.67(1H, d, J=2.0 Hz), 10.13(1H, brs).

EXAMPLE 184

2-[N-(2-Sulfoethyl)carbamoyl]-4-(3,4-methylenedioxybenzyl)amino-6-chloroquinazoline hydrochloride

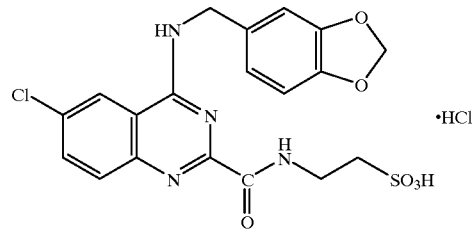

0.60 ml (3.8 mmol) of diethyl cyanophosphate and 0.90 ml (6.4 mmol) of triethylamine were dropped, in this order, into a solution of 0.50 g (1.4 mmol) of 2-carboxy-4-(3,4-methylenedioxybenzyl)amino-6-chloroquinazoline and 0.28 g (1.9 mmol) of sodium 2-aminoethanesulfonate in 15 ml of dimethylformamide under cooling with ice and stirring. The obtained mixture was stirred at room temperature for several days, followed by the addition of 10 ml of 1N hydrochloric acid and water. The crystals thus precipitated were recovered by filtration, washed with water and air-dried to give 0.61 g of the title compound.

molecular formula; $C_{19}H_{17}ClN_4O_6S$.HCl; yield(%); 93; NMR δ (DMSO-d$_6$); 2.76(2H, t, J=6.4 Hz), 3.67(2H, q, J=6.4 Hz), 5.01(2H, d, J=5.6 Hz), 5.99(2H, s), 6.88(1H, d, J=7.6 Hz), 7.05(1H, dd, J=7.6 Hz, 1.6 Hz), 7.11(1H, d, J=1.6 Hz), 8.09(1H, dd, J=8.8 Hz, 2.0 Hz), 8.13(1H, d, J=8.8 Hz), 8.68(1H, d, J=2.0 Hz), 9.97(1H, t, J=5.6 Hz), 10.55(1H, brs).

EXAMPLE 185

2-(4-cis-Carboxycyclohexyl)-4-(3,4-methylenedioxybenzyl)amino-6-chloroquinazoline

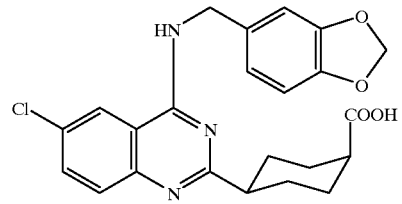

a) 2-(4-Ethoxycarbonylcyclohexylcarbonyl)amino-5-chlorobenzamide 1.5 g of 4-ethoxycarbonylcyclohexanecarbonyl chloride was added to a mixture comprising 1.23 g of 2-amino-5- chlorobenzamide hydrochloride, 3 ml of N,N-diisopropylethylamine and 100 ml of tetrahydrofuran at room temperature. The obtained mixture was reacted at room temperature overnight, followed by the addition of water. The resulting mixture was extracted with ethyl acetate. The organic layer was washed with water and a saturated aqueous solution of sodium chloride, dried over magnesium sulfate, and concentrated. The residue was subjected to silica gel chromatography with 30 to 35% ethyl acetate/hexane to give 1.5 g of the title compound (as a cis/trans mixture).

b) 2-(4-Ethoxycarbonylcyclohexyl)-6-chloroquinazolin-4-one 1.3 g of the compound prepared in the step (a) was suspended in 20 ml of ethanol. 320 mg of potassium t-butoxide was added to the obtained suspension in three portions at room temperature. The resulting mixture was reacted at room temperature overnight. The reaction mixture was partially concentrated, followed by the addition of water and 3.5 ml of 1N hydrochloric acid in this order. The crystals thus precipitated were recovered by filtration, washed with water, and vacuum-dried over phosphorus pentaoxide to give 1.16 g of the title compound (as a cis/trans mixture).

c) 2-(4-cis-Ethoxycarbonylcyclohexyl)-4,6-dichloroquinazoline 20 ml of phosphorus oxychloride was added to 1.0 g of the compound prepared in the step (b). The obtained mixture was heated under reflux for 2 hours and concentrated. 50 ml of chloroform was added to the residue to form a solution, which was poured into a saturated aqueous solution of sodium hydrogencarbonate cooled with ice. The chloroform layer was recovered and the aqueous layer was extracted with 30 ml of chloroform. The chloroform layers were combined, washed with a saturated aqueous solution of sodium chloride, dried over magnesium sulfate, and filtered through a silica gel bed. The silica gel was washed with 10% ethyl acetate/hexane. The washings and the filtrate were combined and concentrated. The residue was subjected to silica gel column chromatography with 5% ethyl acetate/hexane to give 145 mg of the title compound.

NMR δ (CDCl$_3$); 1.28(3H, t, J=7.2 Hz), 1.69~1.78(2H, m), 1.92~2.02(2H, m), 2.05~2.21(4H, m), 2.61~2.68(1H, m), 3.05~3.13(1H, m), 4.17(2H, q, J=7.2 Hz), 7.83(1H, dd, J=9.2 Hz, 2.4 Hz), 7.94(1H, d, J=9.2 Hz), 8.19-(1H, d, J=2.4 Hz).

Simultaneously, 470 mg of 2-(4-trans-ethoxycarbonylcyclohexyl)-4,6-dichloroquinazoline was obtained as a more highly polar component.

NMR δ (CDCl$_3$); 1.28(3H, t, J=7.2 Hz), 1.57~1.69(2H, m), 1.71~1.84(2H, m), 2.13~2.24(4H, m), 1.41(1H, tt, J=12.2 Hz, 3.5 Hz), 2.99(1H, tt, J=12.2 Hz, 3.5 Hz), 4.15 (2H, q, J=7.2 Hz), 7.84(1H, dd, J=9.2 Hz, 2.4 Hz), 7.94(1H, d, J=9.2 Hz), 8.20(1H, d, J=2.4 Hz).

d) 2-(4-cis-Ethoxycarbonylcychlohexyl)-4-(3,4-methylenedioxybenzyl)amino-6-chloroquinazoline A mixture comprising 145 mg of the compound prepared in the step (c), 80 mg of 3,4-methylenedioxybenzylamine, 20 μl of triethylamine and 5 ml of isopropyl alcohol was maintained at 80° C. for 3 hours to conduct a reaction. The reaction mixture was concentrated and extracted with ethyl acetate/water. The ethyl acetate layer was washed with water and a saturated aqueous solution of sodium chloride, dried over anhydrous magnesium sulfate, and concentrated. The residue was subjected to silica gel column chromatography with 15% ethyl acetate/hexane to give 190 mg of the title compound.

NMR δ (CDCl$_3$); 1.25(3H, t, J=7.2 Hz), 1.66~1.75(2H, m), 1.84~1.72(2H, m), 2.05~2.23(4H, m), 2.60~2.66(1H, m), 2.85~2.93(1H, m), 4.15(2H, q, J=7.2 Hz), 4.74(2H, d, J=5.6 Hz), 5.72(1H, t, J=5.6 Hz), 5.96(2H, s), 6.79(1H, d, J=8.0 Hz), 6.85~6.90(2H, m), 7.58~7.62(2H, m), 7.74(1H, d, J=9.6 Hz).

e) 2-(4-cis-Carboxycyclohexyl)-4-(3,4-methylenedioxybenzyl)amino-6-chloroquinazoline 25 ml of ethanol and 2 ml of a 1N aqueous solution of sodium hydroxide were added to the compound prepared in the step (d). The obtained mixture was maintained at 60° C. for 8 hours and thereafter heated under reflux for 3 hours to conduct a reaction. The reaction mixture was cooled to room temperature, followed by the addition of 2 ml of 1N aqueous hydrochloric acid. The resulting mixture was partially concentrated to precipitate crystals. The crystals were recovered by filtration, washed with water and diethyl ether, and vacuum-dried over phosphorus pentaoxide to give 138 mg of the title compound.

molecular formula; C$_{23}$H$_{22}$ClN$_3$O$_4$; yield(%); 77; m.p.(° C.); 152~153; Mass m/e; 440 (M+1) NMR δ (DMSO-d$_6$); 1.54~1.64(2H, m), 1.66~1.76(2H, m), 1.89~2.02(4H, m), 2.69~2.77(1H, m), 4.63(2H, d, J=5.6 Hz), 5.96(2H, s), 6.84(1H, d, J=8.0 Hz), 6.89(1H, dd, J=8.0 Hz, 1.6 Hz), 6.95(1H, d, J=1.6 Hz), 7.63(1H, d, J=8.8 Hz), 7.71(1H, dd, J=8.8 Hz, 2.4 Hz), 8.36(1H, d, J=2.4 Hz), 8.71(1H, t, J=5.6 Hz).

EXAMPLE 186

2-(4-trans-Carboxycyclohexyl)-4-(3,4-methylenedioxybenzyl)amino-6-chloroquinazoline

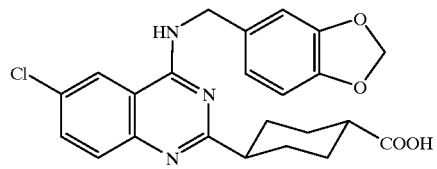

a) 2-(4-trans-Ethoxycarbonylcyclohexyl)-4-(3,4-methylenedioxybenzyl)amino-6-chloroquinazoline 145 mg of the trans isomer prepared in the step (c) of Example 296 was treated in a similar manner to that of the step (d) of Example 296 to give 180 mg of the title compound.

NMR δ (CDCl$_3$); 1.27(3H, t, J=7.2 Hz), 1.54~1.67(2H, m), 1.70~1.83(2H, m), 2.08~2.17(4H, m), 2.39(1H, tt, J=12.2 Hz, 3.2 Hz), 2.79(1H, tt, J=12.2 Hz, 3.2 Hz), 4.14 (2H, q, J=7.2 Hz), 4.76(2H, d, J=5.5 Hz), 5.82(1H, t, J=5.5 Hz), 5.96(2H, s), 6.79(1H, d, J=7.9 Hz), 6.86(1H, dd, J=7.9 Hz, 1.6 Hz), 6.90(1H, d, J=1.6 Hz), 7.59~7.63(2H, m), 7.73(1H, d, J=7.9 Hz).

b) 2-(4-Trans-carboxycyclohexyl)-4-(3,4-methylenedioxybenzyl)amino-6-chloroquinazoline The compound prepared in the step (a) was hydrolyzed in a similar manner to that of the step (e) of Example 296 to give 163 mg of the title compound.

molecular formula; C$_{23}$H$_{22}$ClN$_3$O$_4$; yield(%); 96; m.p.(° C.); 245~246; Mass m/e; 440 (M+1); NMR δ (DMSO-D$_6$); 1.38~1.50(2h, m), 1.55~1.68(2H, m), 1.94~2.04(4H, m), 2.34(1H, tt, J=11.9 Hz, 3.1 Hz), 2.60(1H, tt, J=11.9 Hz, 3.1 Hz), 4.66(2H, d, J=5.7 Hz), 5.97(2H, s), 6.85(1H, d, J=8.1 Hz), 6.88(1H, dd, J=8.1 Hz, 1.5 Hz), 6.98(1H, d, J=1.5 Hz), 7.63(1H, d, J=9.0 Hz), 7.72(1H, dd, J=9.0 Hz, 2.4 Hz), 8.37(1H, d, J=2.4 Hz), 8.71(1H, brt, J=5.7 Hz), 12.04(1H, s).

EXAMPLE 187

2-(4-trans-Carboxycyclohexyl)-4-(3,4-methylenedioxybenzyl)amino-6-cyanoguinazoline

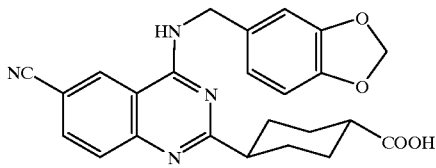

a) 4-(4-methoxycarbonylcyclohexanecarbonyl)aminobenzene-1,3-dicarboxamide 5.1 g of 4-methoxycarbonylcyclohexanecarbonyl chloride was added to a mixture comprising 3.6 g of 4-aminobenzene-1,3-dicarboxamide, 5 ml of N,N-dimethylaniline and 50 ml of tetrahydrofuran at room temperature. The obtained mixture was reacted as such overnight, followed by the addition of water. The crystals thus precipitated were recovered by filtration, washed with water and diethyl ether, and dried to give 5.77 g of the title compound.

b) 2-(4-Methyoxycarbonylcyclohexyl)-6-carbamoylquinazoline-4-one 5.7 g of the compound prepared in the step (a) was suspended in 200 ml of methanol, followed by the addition of 1.84 g of potassium t-butoxide. The obtained mixture was reacted at room temperature overnight, followed by the addition of water. The resulting mixture was acidified with concentrated hydrochloric acid to precipitate crystals. The crystals were recovered by filtration, washed with water and diethyl ether, and dried to give 5.04 g of the title compound.

c) 2-(4-trans-Methoxycarbonylcyclohexyl)-4-chloro-6-cyanoquinazoline

A mixture comprising 2.0 g of the compound prepared in the step (b), 2.0 g of lithium chloride and 40 ml of phosphorus oxychloride was heated under reflux for 6 hours and filtered to remove insolubles. The filtrate was concentrated and the residue was subjected to silica gel column chromatography with 10% ethyl acetate/hexane, whereby the trans isomer was separated from the cis isomer. 180 mg of the title compound was obtained.

NMR δ (CDCl$_3$); 1.57~1.70(2H, m), 1.72~1.84(2H, m), 2.12~2.26(4H, m), 2.43(1H, tt, J=12.3 Hz, 3.2 Hz), 3.03(1H, tt, J=11.9 Hz, 3.0 Hz), 3.71(3H, s), 8.04(1H, dd, J=8.8 Hz, 1.6 Hz), 8.08(1H, dd, J=8.8 Hz, 0.5 Hz), 8.62(1H, dd, J=1.6 Hz, 0.5 Hz).

d) 2-(4-trans-Methoxycarbonylcyclohexyl)-4-(3,4-methylenedioxybenzyl)amino-6-cyanoquinazoline A mixture comprising 180 mg of the compound prepared in the step (c), 100 mg of 3,4-methylenedioxybenzylamine, 200 μl of triethylamine and 5 ml of isopropyl alcohol was maintained at 80° C. for one hour to conduct a reaction. The reaction mixture was concentrated and extracted with ethyl acetate/water. The ethyl acetate layer was washed with a saturated aqueous solution of sodium chloride, dried over anhydrous magnesium sulfate, and concentrated. The residue was subjected to silica gel column chromatography with 10% ethyl acetate/benzene to give 157 mg of the title compound.

NMR δ (CDCl$_3$); 1.55~1.68(2H, m), 1.70~1.82(2H, m), 2.10~2.18(4H, m), 2.42(1H, tt, J=12.3 Hz, 3.2 Hz), 2.81(1H, tt, J=11.9 Hz, 3.0 Hz), 3.70(3H, s), 4.78(2H, d, J=5.5 Hz), 6.96(2H, s), 6.20(1H, t, J=5.5 Hz), 6.80(1H, d, J=7.9 Hz), 6.88(1H, dd, J=7.9 Hz, 1.6 Hz), 6.90(1H, d, J=1.6 Hz), 7.82(2H, s), 8.11(1H, s).

e) 2-(4-trans-Carboxycyclohexyl)-4-(3,4-methylenedioxybenzyl)amino-6-cyanoquinazoline A mixture comprising 157 mg of the compound prepared in the step (d), 1 ml of a 1N aqueous solution of sodium hydroxide, 3 ml of methanol and 6 ml of tetrahydrofuran was reacted at room temperature for 24 hours. 1 ml of 1N hydrochloric acid and 5 ml of water were added to the reaction mixture in this order to precipitate crystals. The crystals were recovered by filtration, washed with water, and dried to give 138 mg of the title compound.

molecular formula; C24H$_{22}$N$_4$O$_4$; yield(%); 91; m.p.(° C.); 269~270; Mass m/e; 431 (M+1); NMR δ (DMSO-d$_6$); 1.38~1.50(2H, m), 1.55~1.68(2H, m), 1.95~2.04(4H, m), 2.24(1H, tt, J=11.9 Hz, 3.1 Hz), 2.63(1H, tt, J=11.9 Hz, 3.1 Hz), 4.68(2H, d, J=5.7 Hz), 5.97(2H, s), 6.86(1H, d, J=7.9 Hz), 6.90(1H, dd, J=7.9 Hz, 1.5 Hz), 6.99(1H, d, J=1.5 Hz), 7.71(1H, d, J=8.8 Hz), 8.01(1H, dd, J=8.8 Hz, 1.6 Hz), 8.82(1H, d, J=1.6 Hz), 8.95(1H, t, J=5.7 Hz).

EXAMPLE 188

2-Carbamoylmethyl-4-(3,4-methylenedioxybenzyl)amino-6-chloroquinazoline

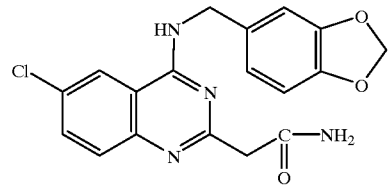

a) 2-Ethoxycarbonylmethyl-4-(3,4-methylenedioxybenzyl)amino-6-chloroquinazoline

The title compound was prepared in a similar manner to that of example 296.

NMR δ (CDCl$_3$); 1.27(3H, t, J=7.1 Hz), 3.93(2H, s), 4.22(2H, q, J=7.1 Hz), 4.71(2H, d, J=5.5 Hz), 5.83(1H, t, J=5.5 Hz), 5.96(2H, s), 6.78(1H, d, J=7.9 Hz), 6.85(1H, dd, J=7.9 Hz, 1.6 Hz), 6.89(1H, d, J=1.6 Hz), 7.60~7.65(2H, m), 7.74(1H, d, J=9.0 Hz).

b) 2-Carbamoylmethyl-4-(3,4-methylenedioxybenzyl)amino-6-chloroquinazoline

A mixture comprising 200 mg of the compound prepared in the step (a) and 20 ml of ethanol was cooled with ice. Ammonium gas was introduced into the resulting mixture to saturate the mixture therewith. The resulting mixture was gradually brought to room temperature and reacted for 3 days. The reaction mixture was concentrated and the residue was subjected to silica gel column chromatography with 0 to 20% ethanol/ethyl acetate to give 24 mg of the title compound.

EXAMPLE 189

2-[4-(1H-tetrazol-5-y)piperidino]-4-(3,4-methylenedioxybenzyl)amino-6-chloroquinazoline hydrochloride

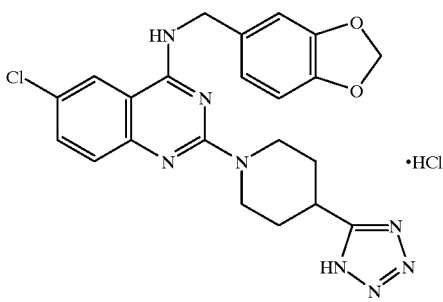

10 ml of toluene was added to a mixture comprising 0.50 g (0.0012 mol) of 2-(4-cyanopiperidino)-4-(3,4-methylenedioxybenzyl)amino-6-chloroquinazoline and 0.50 g (0.0024 mol) of trimethyl stannylazide. The mixture thus obtained was heated under reflux for two days. The reaction mixture was distilled under a reduced pressure to remove the solvent. The residue was suspended in 10 ml of ethanol, followed by the addition of 10 ml of 1N hydrochloric acid. The mixture thus obtained was stirred at room temperature for several hours. The mixture was filtered to recover the crystal. The crystal was washed with water and air-dried to give 0.60 g of the title compound.

molecular formula; $C_{22}H_{21}ClN_8O_2 \cdot HCl$; yield(%); quantitive; m.p.(° C.); 212~214; Mass m/e; 465 (M+1)$^+$; NMR δ (DMSO-d$_6$); 1.80 (2H,m), 2.17 (2H, m), 3.45 (2H, m), 4.62 (2H, m), 4.69 (2H, d, J=5.6 Hz), 5.97 (2H, s), 6.86 (1H, d, J=7.6 Hz), 6.91 ((1H, dd, J=7.6 Hz, 1.6 Hz), 7.01 (1H, d, J=1.6 Hz), 7.84 (1H, dd, J=8.8 Hz, 1.6 Hz), 7.88 (1H, d, J=8.8 Hz), 8.51 (1H, d, J=1.6 Hz), 10.13 (1H, brs), 12.28 (1H, brs).

EXAMPLE 190

2-(1H-tetrazol-5-yl)-4-(3,4-methylenedioxybenzyl) amino-6-chloroquinazoline hydrochloride

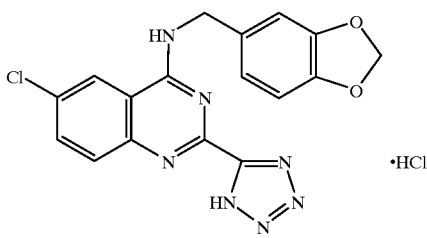

The title compound was prepared in a similar manner to that of Example 189.

molecular formula; $C_{17}H_{12}ClN_7O_2 \cdot HCl$; yield(%); 37; m.p.(° C.); 201~204(dec.); Mass m/e; 382 (MH)$^+$; NMR δ (DMSO-d$_6$); 4.90 (2H, d, J=5.6 Hz), 5.97 (2H, s), 6.87 (1H, d, J=8.0 Hz), 6.98 (1H, dd, J=8.0 Hz, 2.0 Hz), 7.11 (1H, d, J=2.0 Hz), 7.92~7.94 (2H, m), 8.60 (1H, c, J=1.6 Hz), 9.53 (1H, brs).

EXAMPLES 191

The following compound was prepared by any method described above.

EXAMPLE 191

2-Chloro-4-(3,4-methylenedioxybenzyl)amino-6-methoxy-7-cyclopentyloxyquinazoline

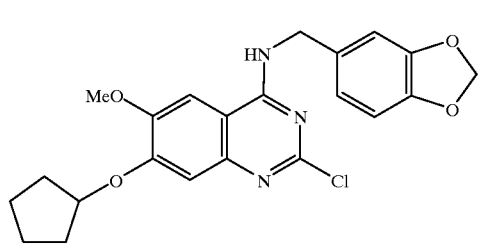

molecular formula; $C_{22}H_{22}ClN_3O_4$; yield(%); 88; m.p.(° C.); 176~177; Mass m/e; 428 (M+1)$^+$; NMR δ (CDCl$_3$); 1.64 (2H, m), 1.82 (2H, m), 1.93 (2H, m), 2.02 (2H, m), 3.90 (3H, s), 4.74 (2H, d, J=5.6 Hz), 4.85 (1H, m), 5.72 (1H, t, J=5.6 Hz), 5.96 (2H, s), 6.79 (1H, d, J=7.6 Hz), 6.79 (1H, s), 6.87 (1H, dd, J=7.6 Hz, 1.6 Hz), 6.90 (1H, d, J=1.6 Hz), 7.11 (1H, s).

It will be understood that various changes and modifications can be made in the details of procedure, formulation and use without departing from the spirit of the invention, especially as defined in the following claims.

We claim:

1. A method of treating a patient having precancerous lesions in the need of treatment, comprising administering to the patient sensitive to such a compound a pharmacologically effective amount of a compound of the formula:

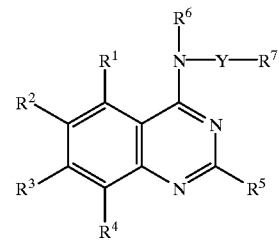

wherein R1, R2, R3 and R4, each of which may be the same or different, are selected from a hydrogen atom, a alkoxy group having 1 to 6 carbon atoms, a hydroxyalkyl group, a cyano group, an acylamino group, a carboxyl group which may be protected or two of R1, R2, R3 or R4 may together form methylenedioxy, ethylenedioxy, or a phenyl ring;

R5 is selected from a hydrogen atom, a halogen atom, a hydroxyl group, a hydrazino group, an alkyl group having 1 to 6 carbon atoms, an alkoxy group having 2 to 8 carbon atoms, an alkenyl group which may be protected having 2 to 8 carbon atoms, a carboxyalkenyl group which may be protected having 3 to 8 carbon atoms, a hydroxyalkyl group having 1 to 6 carbon atoms, or a carboxyl group which may be protected, R6 is selected from a hydrogen atom, a alkyl group having 1 to 6 carbon atoms, an acyl group, a lower alkoxyalkyl group having 2 to 8 carbon atoms, a carboxyalkyl group having 2 to 8 carbon atoms which may be protected or a hydroxyalkyl group having 2 to 8 carbon atoms;

R7 is selected from a hydrogen atom, a hydroxyl group, a carboxyl group which may be protected, a cyano group, an acyl group, or a benzyl group which may be substituted, said substitutions, which may be the same or different, are selected from a hydrogen atom, a halogen atom, a hydroxyl group, an amino group, a nitro group, a alkyl group having 1 to 6 carbon atoms, a alkoxy group having 1 to 6 carbon atoms, a alkoxyalkyl group having 2 to 8 carbon atoms, a alkenyl group having 2 to 8 carbon atoms, an acyl group an acylamino group, an alkylsulfonylamino group, a hydroiminoalkyl group, an alkyloxy-carbonylamino group, or an alkyloxybarbonyloxy group, wherein the alkyls are 2 to 8 carbon atoms; and Y is a group represented by the formula —(CH2)q— wherein q is an integer of 1 to 8, when q is an integer of 1 to 8, each carbon atom may have from 1 to 2 substituents, or Y is a group represented by the formula:

2. The method of claim 1, wherein R1, R2, R3, and R4, each of which may be the same or different from one another, are selected from a hydrogen atom, a cyano group, a halogen atom, or a lower alkoxy group.

3. The method of claim 2, wherein one of R1, R2, R3 and R4 is a cyano group, a chlorine atom or a methoxy atom.

4. The method of claim 3, wherein R2 is a halogen atom.

5. The method of claim 4, wherein R2 is a chlorine atom.

6. The method of claim 5, wherein R1, R3 and R4 are hydrogen atoms.

7. The method of claim 6, wherein Y is a group represented by the formula —(CH2)q—, wherein q is an integer of 1 to 8.

8. The method of claim 7, wherein R7 is a benzyl group which may be substituted, said substitutions, each of which may be the same or different, are each selected from a hydrogen atom, a halogen atom, a hydroxy group, an amino group, a nitro group, a lower alkyl group, a lower alkoxy group, a lower alkoxyalkyl group, a lower alkenyl group, an acyl group, an acylamino group, an alkylsulfonylamino group, a hydroxyiminoalkyl group, an alkyloxycarbonylamino group, or an alkyloxycarbonyloxy group; and q is an integer of 1 to 8.

9. The method of claim 1, wherein Y is a group represented by the formula —(CH2)q—, wherein q is an integer of 1 to 8.

10. The method for inhibiting the growth of neoplastic cells, comprising exposing said cells sensitive to such a compound to an effective amount of a compound of formula:

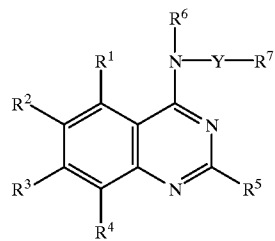

wherein R1, R2, R3 and R4, each of which may be the same or different, are selected from a hydrogen atom, a alkoxy group having 1 to 6 carbon atoms, a hydroxyalkyl group, a cyano group, an acylamino group, a carboxyl group which may be protected or two of R1, R2, R3 or R4 may together form methylenedioxy, ethylenedioxy, or a phenyl ring;

R5 is selected from a hydrogen atom, a halogen atom, a hydroxyl group, a hydrazino group, an alkyl group having 1 to 6 carbon atoms, an alkoxy group having 2 to 8 carbon atoms, an alkenyl group which may be protected having 2 to 8 carbon atoms, a carboxyalkenyl group which may be protected having 3 to 8 carbon atoms, a hydroxyalkyl group having 1 to 6 carbon atoms, or a carboxyl group which may be protected, R6 is selected from a hydrogen atom, a alkyl group having 1 to 6 carbon atoms, an acyl group, a lower alkoxyalkyl group having 2 to 8 carbon atoms, a carboxyalkyl group having 2 to 8 carbon atoms which may be protected or a hydroxyalkyl group having 2 to 8 carbon atoms;

R7 is selected from a hydrogen atom, a hydroxyl group, a carboxyl group which may be protected, a cyano group, an acyl group, or a benzyl group which may be substituted, said substitutions, which may be the same or different, are selected from a hydrogen atom, a halogen atom, a hydroxyl group, an amino group, a nitro group, a alkyl group having 1 to 6 carbon atoms, a alkoxy group having 1 to 6 carbon atoms, a alkoxyalkyl group having 2 to 8 carbon atoms, a alkenyl group having 2 to 8 carbon atoms, an acyl group an acylamino group, an alkylsulfonylamino group, a hydroiminoalkyl group, an alkyloxy-carbonylamino group, or an alkyloxybarbonyloxy group; wherein the alkyls are 2 to 8 carbon atoms; and Y is a group represented by the formula —(CH2)q— (wherein q is an integer of 1 to 8), when q is an integer of 1 to 8, each carbon atom may have from 1 to 2 substituents, or Y is a group represented by the formula:

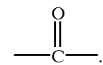

* * * * *